(12) United States Patent
Bailey et al.

(10) Patent No.: US 9,598,420 B2
(45) Date of Patent: Mar. 21, 2017

(54) BENZODIAZEPINE BROMODOMAIN INHIBITOR

(71) Applicant: GlaxoSmithKline LLC, Wilmington, New Castle, DE (US)

(72) Inventors: James Bailey, Stevenage (GB); Romain Luc Marie Gosmini, Les Ulis (FR); Olivier Mirguet, Les Ulis (FR); Jason Witherington, Stevenage (GB)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 0 days.

(21) Appl. No.: 14/753,326

(22) Filed: Jun. 29, 2015

(65) Prior Publication Data
US 2015/0299210 A1    Oct. 22, 2015

Related U.S. Application Data

(63) Continuation of application No. 13/504,971, filed as application No. PCT/EP2010/066697 on Nov. 3, 2010, now Pat. No. 9,102,677.

(30) Foreign Application Priority Data

| Nov. 5, 2009 | (GB) | 0919433.3 |
| Jun. 22, 2010 | (GB) | 1010509.6 |
| Aug. 6, 2010 | (WO) | PCT/EP2010/061518 |
| Aug. 25, 2010 | (GB) | 1014231.3 |

(51) Int. Cl.
*A61K 31/551* (2006.01)
*C07D 487/04* (2006.01)

(52) U.S. Cl.
CPC .................. *C07D 487/04* (2013.01)

(58) Field of Classification Search
CPC .......................... C07D 487/04; A61K 31/551
USPC ......................................... 540/566; 514/220
See application file for complete search history.

(56) References Cited

U.S. PATENT DOCUMENTS

| 4,374,773 A | 2/1983 | Branca et al. |
| 5,116,971 A | 5/1992 | Harreus et al. |
| 8,697,725 B2 | 4/2014 | Demont et al. |
| 2005/0222034 A1 | 10/2005 | Hsu |

FOREIGN PATENT DOCUMENTS

| CA | 2710740 A1 | 7/2009 |
| EP | 0638560 | 2/1995 |
| EP | 0792880 | 9/1997 |
| EP | 0934940 A1 | 8/1999 |
| EP | 0989131 A1 | 3/2000 |
| EP | 1887008 A1 | 2/2008 |
| EP | 2239264 A1 | 10/2010 |
| JP | 6128257 | 5/1994 |
| JP | 2008156311 A | 7/2008 |
| WO | 9514694 | 6/1995 |
| WO | 9747622 | 12/1997 |
| WO | 2006032470 A1 | 3/2006 |
| WO | 2009084693 A1 | 7/2009 |
| WO | 2011054553 | 5/2011 |
| WO | 2011054843 | 5/2011 |

OTHER PUBLICATIONS

Bock M.G, et al; Cholecystokinin Antagonists. Synthesis and Biological Evaluation of 4-substituted 4H-U1,2,4 3/4 Triazolou4, 3-A 3/4 U1,4 3/4 Benzodiazepines; Journal of Medicinal Chemistry, American Chemical Society; vol. 31, No. 1; 176-180, 1988.
CAPLUS printout of JP 06128257, 1994.
Database WPI Week 200137 Thomson Scientific, London, GB; AN 2001-355895 XP002615613 and WO 01/38377 A1 (Bioroad Gene Dev Ltd Shanghai) May 31, 2001 abstract.
Database WPI Week 200167. Thomson Scientific, London, GB; AN 2001-597108XP002615614 and WO 01/72812 A1 (Bode Gene Dev Co Ltd, Shanghai) Oct. 4, 2001 abstract.
Huang, Bo, et al; Brd4 Coactivates Transcriptional Activation of NF-kappa B via Specific Binding to Acetylated RelA; Molecular and Cellular Biology; Mar. 2009; vol. 29, No. 5; 1375-1387.
Wang, F., et al.; Brd2 disruption in mice causes severe obesity without Type 2 diabetes; Biochemical Journal; Nov. 2, 2009; vol. 425, No. Part 1; 71-83 + Suppl p. 81 para 1.
Lima, L.M. et al. Bioisdosterism: a useful strategy for molecular modification and drug design. Current Med. Chem. 2005,12(1), pp. 23-49.

*Primary Examiner* — Brenda Coleman
(74) *Attorney, Agent, or Firm* — Duke M. Fitch; Kathryn A. Lutomski; Edward R. Gimmi

(57) ABSTRACT

Benzodiazepine compounds of formula (I)

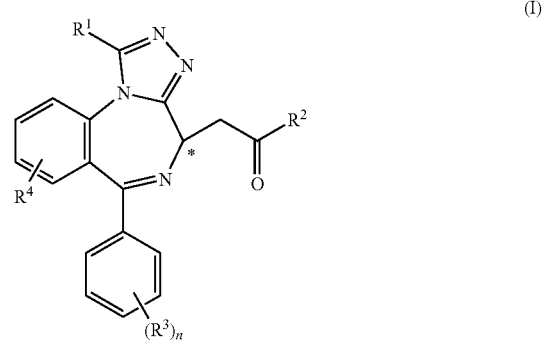

and salts thereof, pharmaceutical compositions containing such compounds and their use in therapy.

12 Claims, No Drawings

BENZODIAZEPINE BROMODOMAIN INHIBITOR

CROSS-REFERENCE TO RELATED APPLICATIONS

This application is as continuation of U.S. Ser. No. 13/504,971 filed on Jun. 18, 2012, which is a National Phase Application of International Patent Application Serial No. PCT/EP2010/066697 filed on Nov. 3, 2010, which claims priority from 0919433.3 filed on Nov. 5, 2009, 1010509.6 filed on Jun. 22, 2010, 1014231.3 filed on Aug. 25, 2010 in the United Kingdom and PCT/EP2010/061518 filed on Aug. 6, 2010 in Europe.

FIELD OF THE INVENTION

The present invention relates to benzodiazepine compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD3-NUT or BRD4-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogensesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009/084693A1 discloses a series of thienotriazolodiazepiene derivatives that are said to inhibit the binding between an acetylated histone and a bromodomain containing protein which are said to be useful as anti-cancer agents.

A novel class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a compound of formula (I) or a pharmaceutically acceptable salt thereof.

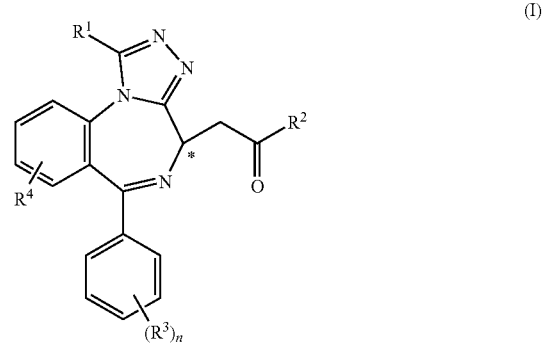

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to compounds of formula (I) or a salt thereof

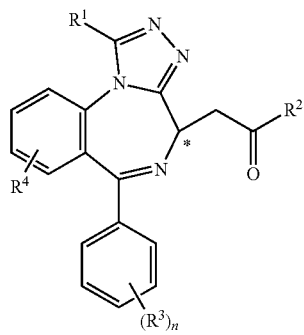

(I)

where
$R^1$ is $C_{1-3}$alkyl;
$R^2$ is —$NR^{2a}R^{2'a}$ or —$OR^{2b}$;
wherein one of $R^{2a}$ or $R^{2'a}$ is hydrogen, and $R^{2b}$ or the other of $R^{2a}$ or $R^{2'a}$ is selected from $C_{1-6}$alkyl, halo$C_{1-6}$alkyl, $R^{2c}R^{2'c}$N—$C_{1-6}$alkyl, carbocyclyl, carbocyclyl$C_{1-4}$alkyl, heterocyclyl and heterocyclyl$C_{1-4}$alkyl,
wherein any of the carbocyclyl or heterocyclyl groups are optionally substituted by one or more groups selected from halogen, $C_{1-6}$alkyl, halo$C_{1-6}$alkyl, $C_{1-6}$alkoxy, halo$C_{1-6}$alkoxy, carbonyl, —CO-carbocyclyl, azido, amino, hydroxyl, nitro and cyano, wherein the —CO-carbocyclyl group may be optionally substituted by one or more groups selected from halogen, $C_{1-6}$alkyl, halo$C_{1-6}$alkyl, $C_{1-6}$alkoxy, halo$C_{1-6}$alkoxy, azido, nitro and cyano;
or two adjacent groups on any of the carbocyclyl or heterocyclyl groups together with the interconnecting atoms form a 5- or 6-membered ring which ring may contain 1 or 2 heteroatoms independently selected from O, S and N;
or $R^{2a}$ and $R^{2'a}$ together with the N-atom to which they are attached form a 4-, 5-, 6- or 7-membered ring which optionally contains 1 or 2 heteroatoms independently selected from O, S and N; wherein the 4-, 5-, 6- or 7-membered ring is optionally substituted by $C_{1-6}$alkyl, hydroxyl or amino;
$R^{2c}$ and $R^{2'c}$ are independently hydrogen or $C_{1-6}$alkyl;
each $R^3$ is independently selected from hydrogen, hydroxyl, halo, $C_{1-6}$alkyl, halo $C_{1-6}$alkyl, $C_{1-6}$alkoxy, halo $C_{1-6}$alkoxy, nitro, cyano, $CF_3$, —$OCF_3$, —$COOR^5$, —$C_{1-4}$ alkylNR$^6$R$^7$ and —$C_{1-4}$alkylOH;
$R^4$ is hydroxyl, halo, $C_{1-6}$alkyl, halo$C_{1-6}$alkyl, $C_{1-6}$alkoxy, halo$C_{1-6}$alkoxy, nitro, cyano, $CF_3$, —$OCF_3$, —$COOR^5$; or —$OS(O)_2C_{1-4}$alkyl;

$R^5$ is $C_{1-3}$alkyl; and
n is an integer 1 to 5.

In one embodiment the present invention relates to compounds of formula (Ic) or a salt thereof

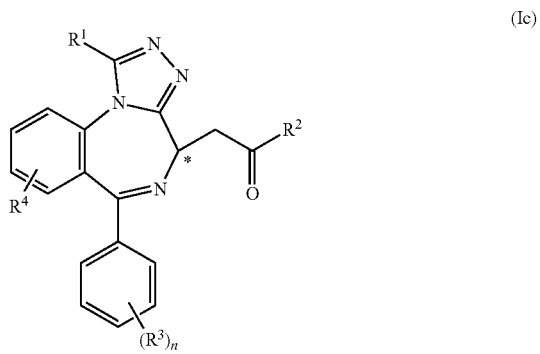

(Ic)

where
$R^1$ is $C_{1-3}$alkyl;
$R^2$ is —$NR^{2a}R^{2'a}$ or —$OR^{2b}$;
wherein one of $R^{2a}$ or $R^{2'a}$ is H, and $R^{2b}$ or the other of $R^{2a}$ or $R^{2'a}$ is selected from $C_{1-6}$alkyl, halo$C_{1-6}$alkyl, $R^{2c}R^{2'c}$N—$C_{1-6}$alkyl, carbocyclyl, carbocyclyl$C_{1-4}$alkyl, heterocyclyl and heterocyclyl$C_{1-4}$alkyl,
wherein any of the carbocyclyl or heterocyclyl groups are optionally substituted by one or more groups selected from halogen, $C_{1-6}$alkyl, halo$C_{1-6}$alkyl, $C_{1-6}$alkoxy, halo$C_{1-6}$alkoxy, carbonyl, —CO-carbocyclyl, azido, nitro and cyano,
wherein the —CO-carbocyclyl group may be further optionally substituted by one or more groups selected from halogen, $C_{1-6}$alkyl, halo$C_{1-6}$alkyl, $C_{1-6}$alkoxy, halo$C_{1-6}$ alkoxy, azido, nitro and cyano;
or two adjacent groups on any of the carbocyclyl or heterocyclyl groups together with the interconnecting atoms form a 5- or 6-membered ring which ring may contain 1 or 2 heteroatoms independently selected from O, S and N;
or $R^{2a}$ and $R^{2'a}$ together with the N-atom to which they are attached form a 5-, 6- or 7-membered ring which may optionally contain 1 or 2 heteroatoms independently selected from O, S and N; wherein the 5-, 6- or 7-membered ring may be further optionally substituted by $C_{1-6}$alkyl;
$R^{2c}$ and $R^{2'c}$ are independently H and $C_{1-6}$alkyl;
each $R^3$ is independently selected from H, hydroxy, halo, $C_{1-6}$alkyl, halo $C_{1-6}$alkyl, $C_{1-6}$alkoxy, halo $C_{1-6}$alkoxy, nitro, cyano, $CF_3$, —$OCF_3$ and —$COOR^5$;
$R^4$ is hydroxy, halo, $C_{1-6}$alkyl, halo $C_{1-6}$alkyl, $C_{1-6}$alkoxy, halo $C_{1-6}$alkoxy, nitro, cyano, $CF_3$, —$OCF_3$; —$COOR^5$ or —$OS(O)_2C_{1-4}$alkyl;
$R^5$ is $C_{1-3}$alkyl; and
n is an integer 1 to 5.

In one embodiment of the invention the S-enantiomers are preferred.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "halogen" or "halo" refers to the elements fluorine, chlorine, bromine and iodine. Examples of suitable halogens are fluorine, chlorine and bromine.

Unless otherwise indicated, any carbocyclyl group contains 3 to 14 ring-atoms for example, 3 to 10 ring-atoms, or in a further example, 3 to 8 ring-atoms, and may be saturated, unsaturated or aromatic. Examples of saturated carbocyclyl groups include cyclopropyl, cyclopentyl or cyclohexyl. Examples of unsaturated carbocyclyl groups include those which contain up to 3 double bonds. An example of a suitable aromatic carbocyclyl group is phenyl. The term carbocylic should be similarly construed. In addition, the term carbocyclyl includes any fused combination of carbocyclyl groups, for example naphthyl, anthryl, phenanthryl, indanyl, indenyl, azulenyl, azulanyl, and fluorenyl.

Unless otherwise indicated, any heterocyclyl group contains 4 to 7 ring-atoms, for example, 5 to 7 ring-atoms up to 4 of which may be hetero-atoms such as nitrogen, oxygen and sulfur, and may be saturated, unsaturated or aromatic. Examples of heterocyclyl groups are azetidinyl, furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, homopiperazinyl, dioxanyl, morpholino, dithianyl, thiomorpholino, thiomorpholino-1,1-dioxide, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

As used herein, the term "substituted" refers to substitution with the named substituent or substituents. With multiple degrees of substitution (e.g. 1 or 2) the groups can be the same or different.

In one embodiment of the invention, $R^1$ represents methyl.

In one embodiment of the invention $R^2$ represents $-OR^{2b}$.

Thus there is provided a compound of formula (Ia)

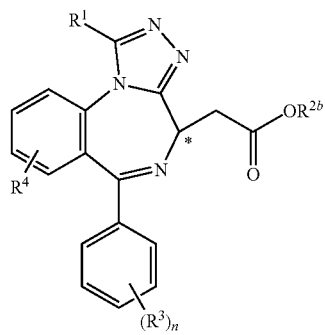

(Ia)

wherein
$R^1$, $R^{2b}$, $R^3$, $R^4$ and n are as defined above for compounds of formula (I).

In one embodiment of the invention $R^2$ is $-NR^{2a}R^{2a'}$.

In one embodiment of the invention one of $R^{2a}$ or $R^{2'a}$ is hydrogen, and the other of $R^{2a}$ or $R^{2'a}$ is selected from $C_{1-6}$alkyl, carbocyclyl, carbocyclyl$C_{1-4}$alkyl, heterocyclyl and heterocyclyl$C_{1-4}$alkyl, wherein any of the carbocyclyl or heterocyclyl groups are optionally substituted by one or more groups selected from halogen, $C_{1-6}$alkyl, halo$C_{1-6}$alkyl, $C_{1-6}$alkoxy, halo$C_{1-6}$alkoxy, carbonyl, $-CO$-carbocyclyl, azido, amino, hydroxyl, nitro and cyano, wherein the $-CO$-carbocyclyl group is optionally substituted by one or more groups selected from halogen, $C_{1-6}$alkyl, halo$C_{1-6}$alkyl, $C_{1-6}$alkoxy, halo$C_{1-6}$alkoxy, azido, nitro and cyano. In another embodiment one of $R^{2a}$ or $R^{2'a}$ is hydrogen, and the other of $R^{2a}$ or $R^{2'a}$ is selected from $C_{1-6}$alkyl, phenyl, benzyl, benzofuranyl, pyridinyl, thiazoyl, furanyl, and morpholinyl, wherein the phenyl, benzyl, benzofuranyl, pyridinyl, thiazoyl, furanyl, or morpholinyl groups are optionally subtituted by one or more substituents selected from halogen, $C_{1-6}$alkyl, halo$C_{1-6}$alkyl, $C_{1-6}$alkoxy, halo$C_{1-6}$alkoxy, carbonyl, azido, nitro and cyano. In another embodiment $R^{2a}$ is hydrogen and $R^{2'a}$ is $C_{1-6}$alkyl. In a further embodiment $R^{2'a}$ is ethyl.

In one embodiment of the invention $R^{2a}$ is hydrogen and $R^{2'a}$ is $R^{2c}R^{2'c}N-C_{1-6}$alkyl. In another embodiment $R^{2'a}$ is selected from $R^{2c}R^{2'c}N-CH_2-$, $R^{2c}R^{2'c}N-CH_2CH_2-$, $R^{2c}R^{2'c}N-CH_2CH_2CH_2-$ and $R^{2c}R^{2'c}N-CH_2CH_2CH_2CH_2-$. In a further embodiment $R^{2c}$ and $R^{2'c}$ are selected from hydrogen and methyl.

In one embodiment of the invention $R^{2a}$ is hydrogen and $R^{2'a}$ is carbocyclyl. In another embodiment $R^{2'a}$ is cyclopentyl or cyclohexyl, wherein each group is optionally substituted once by amino or hydroxyl.

In one embodiment of the invention $R^{2a}$ is hydrogen and $R^{2'a}$ is heterocyclyl. In another embodiment $R^{2'a}$ is selected from pyrrolidinyl, piperidinyl, tetrahydrofuranyl and tetrahydropyran, wherein each group is optionally substituted by $C_{1-6}$alkyl. In another embodiment $R^{2'a}$ is selected from:

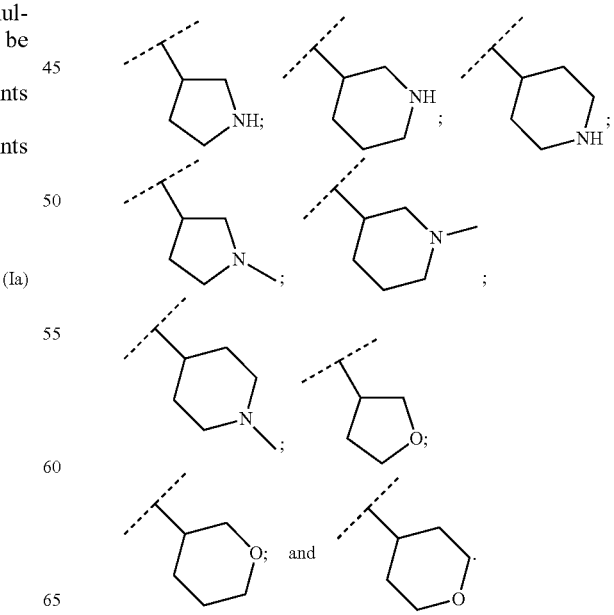

In a further embodiment $R^{2'a}$ is selected from:

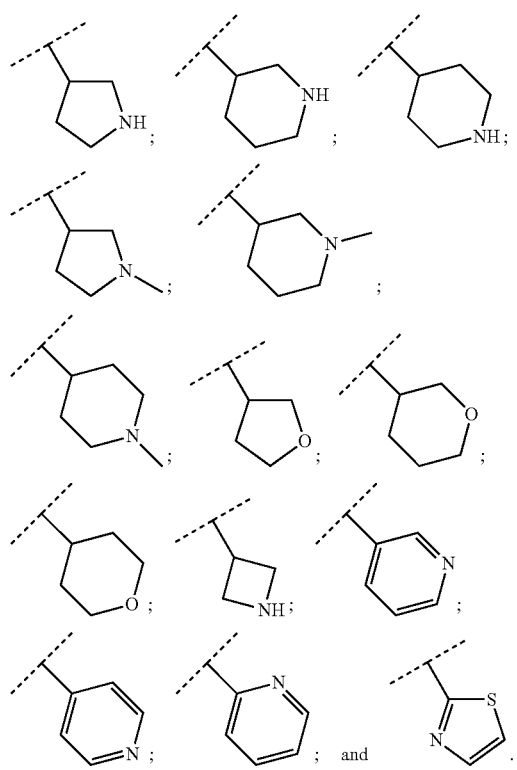

In one embodiment of the invention $R^{2a}$ is hydrogen and $R^{2'a}$ is heterocyclyl$C_{1-4}$alkyl, wherein the heterocyclyl is optionally substituted once by amino, hydroxyl or methyl. In another embodiment $R^{2'a}$ is selected from heterocyclyl-CH$_2$—, heterocyclyl-CH$_2$CH$_2$—, heterocyclyl-CH$_2$CH$_2$CH$_2$— and heterocyclyl-CH$_2$CH$_2$CH$_2$CH$_2$—, wherein the heterocyclyl is optionally substituted once by amino, hydroxyl or methyl. In another embodiment heterocyclyl is selected from pyrrolidinyl, piperidinyl, tetrahydropyranyl, piperazinyl, morpholino and thiomorpholinodioxide, wherein each group is optionally substituted once by amino, hydroxyl or methyl. In another embodiment heterocyclyl is selected from:

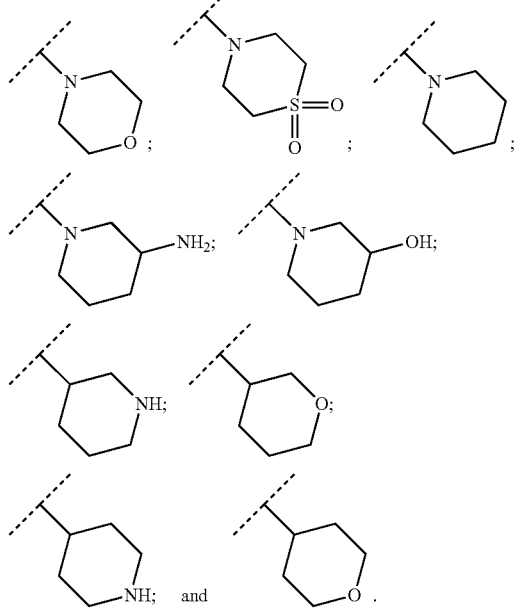

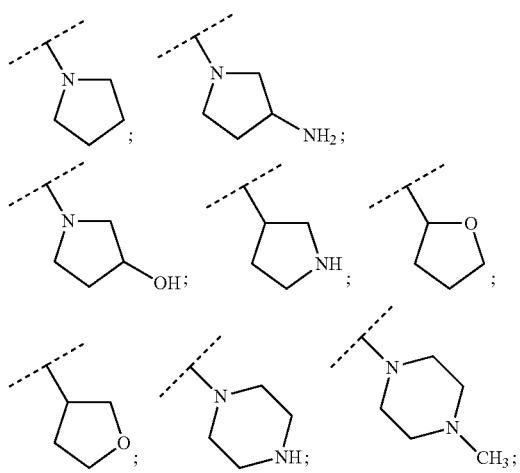

In a further embodiment heterocyclyl is selected from:

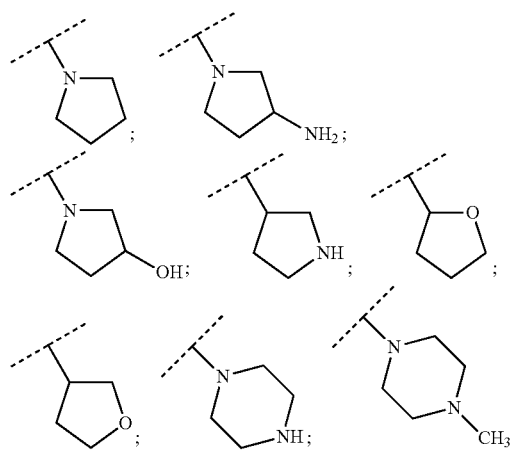

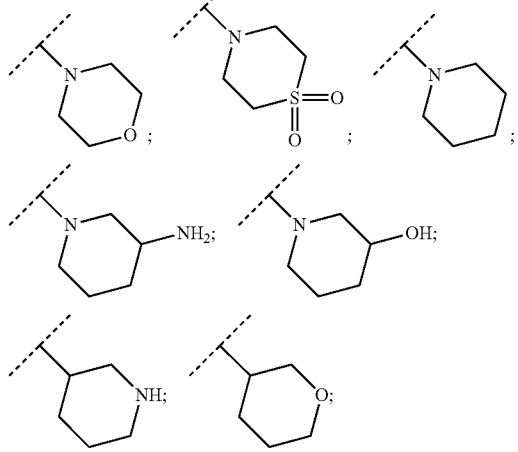

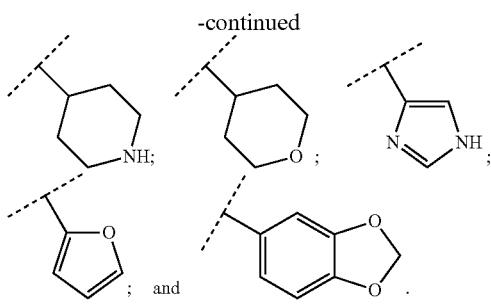

In one embodiment of the invention, $R^{2a}$ and $R^{2'a}$ together with the N-atom to which they are attached form a 5-, 6- or 7-membered ring which optionally contains 1 or 2 heteroatoms independently selected from O, S and N; wherein the 5-, 6- or 7-membered ring is optionally substituted by $C_{1-6}$alkyl.

In another embodiment of the invention, $R^{2a}$ and $R^{2'a}$ together with the N-atom to which they are attached form a 4-, 5-, 6- or 7-membered ring which optionally contains 1 or 2 heteroatoms independently selected from O, S and N; wherein the 4-5-, 6- or 7-membered ring is optionally substituted by $C_{1-6}$alkyl, hydroxyl or amino. In another embodiment the 4-, 5-, 6- or 7-membered ring is selected from:

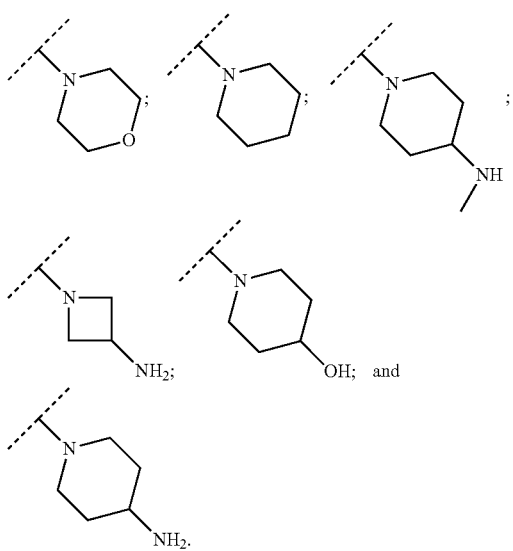

In one embodiment of the invention, $R^{2b}$ represents $C_{1-6}$alkyl, carbocyclyl or carbocyclyl$C_{1-4}$alkyl, wherein the carbocyclyl group is optionally substituted by one or more groups selected from halogen, $C_{1-6}$alkyl, halo$C_{1-6}$alkyl, $C_{1-6}$alkoxy, halo$C_{1-6}$alkoxy, carbonyl, —CO-carbocyclyl, azido, nitro and cyano, and wherein the —CO-carbocyclyl group may be further optionally substituted by one or more groups selected from halogen, $C_{1-6}$alkyl, halo$C_{1-6}$alkyl, $C_{1-6}$alkoxy, halo$C_{1-6}$alkoxy, azido, nitro and cyano. In another embodiment of the invention, $R^{2b}$ represents $C_{1-6}$alkyl, phenyl, or benzyl wherein the phenyl or benzyl group is optionally substituted by one or more groups selected from halogen, $C_{1-6}$alkyl, halo$C_{1-6}$alkyl, $C_{1-6}$alkoxy, halo$C_{1-6}$alkoxy, carbonyl, —CO-carbocyclyl, azido, nitro and cyano, and wherein the —CO-carbocyclyl group may be further optionally substituted by one or more groups selected from halogen, $C_{1-6}$alkyl, halo$C_{1-6}$alkyl, $C_{1-6}$alkoxy, halo$C_{1-6}$alkoxy, azido, nitro and cyano. In another embodiment $R^{2b}$ represents methyl, ethyl, n-butyl, t-butyl, benzyl, iso-propyl, iso-butyl, or phenyl. In a further embodiment, $R^{2b}$ represents ethyl, t-butyl, benzyl, iso-propyl, iso-butyl, or phenyl;

In one embodiment of the invention, $R^3$ represents halo, $C_{1-6}$alkyl, $C_{1-6}$alkoxy or $CF_3$. In another embodiment, $R^3$ represents chloro, fluoro, methoxy or $CF_3$. In another embodiment, $R^3$ represents 3-fluoro, 4-chloro, 4-fluoro, 4-methoxy, or 4-$CF_3$. In a further embodiment $R^3$ represents 4-chloro.

In one embodiment of the invention, $R^4$ represents hydroxyl or $C_{1-6}$alkoxy. In another embodiment, $R^4$ represents MeO.

In one embodiment of the invention, $R^4$ is located in position 8 such as 8-MeO.

Thus in one embodiment the invention provides a compound of formula (Ib)

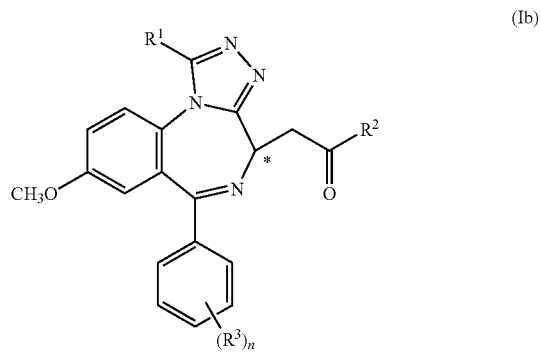

(Ib)

wherein:

$R^1$, $R^2$ and $R^3$ and n are as defined above for compounds of formula (I).

n may for example represent an integer in the range 1 to 3 such as 1.

While the embodiments for each variable have generally been listed above separately for each variable this invention includes those compounds in which several or each embodiment in formula (I) is selected from each of the embodiments listed above. Therefore, this invention is intended to include all combinations of embodiments for each variable described hereinabove including salts thereof.

In one embodiment, examples of compounds of the present invention include:

2-[6-(4-chlorophenyl)-1-methyl-8-(methyloxy)-4H-[1,2,4]triazolo[4,3-a][1,4]benzodiazepin-4-yl]-N-(2-phenylethyl)acetamide;

6-(4-chlorophenyl)-1-methyl-8-(methyloxy)-4-[2-oxo-2-(1-piperidinyl)ethyl]-4H-[1,2,4]triazolo[4,3-a][1,4]benzodiazepine;

2-[6-(4-chlorophenyl)-1-methyl-8-(methyloxy)-4H-[1,2,4]triazolo[4,3-a][1,4]benzodiazepin-4-yl]-N-(2-furanylmethyl)acetamide;

2-[6-(4-chlorophenyl)-1-methyl-8-(methyloxy)-4H-[1,2,4]triazolo[4,3-a][1,4]benzodiazepin-4-yl]-N-cyclohexylacetamide;

2-[6-(4-chlorophenyl)-1-methyl-8-(methyloxy)-4H-[1,2,4]triazolo[4,3-a][1,4]benzodiazepin-4-yl]-N-(2,2,2-trifluoroethyl)acetamide;

2-[(4S)-6-(4-chlorophenyl)-1-methyl-8-(methyloxy)-4H-[1,2,4]triazolo[4,3-a][1,4]benzodiazepin-4-yl]-N-(3-fluorophenyl)acetamide;

2-[(4S)-6-(4-chlorophenyl)-1-methyl-8-(methyloxy)-4H-[1,
2,4]triazolo[4,3-a][1,4]benzodiazepin-4-yl]-N-(4-fluoro-
phenyl)acetamide;
2-[(4S)-6-(4-chlorophenyl)-1-methyl-8-(methyloxy)-4H-[1,
2,4]triazolo[4,3-a][1,4]benzodiazepin-4-yl]-N-(4-fluoro-
phenyl)acetamide;
2-[(4S)-6-(4-chlorophenyl)-1-methyl-8-(methyloxy)-4H-[1,
2,4]triazolo[4,3-a][1,4]benzodiazepin-4-yl]-N-4-pyridi-
nylacetamide;
2-[(4S)-6-(4-chlorophenyl)-1-methyl-8-(methyloxy)-4H-[1,
2,4]triazolo[4,3-a][1,4]benzodiazepin-4-yl]-N-3-pyridi-
nylacetamide;
2-[(4S)-6-(4-chlorophenyl)-1-methyl-8-(methyloxy)-4H-[1,
2,4]triazolo[4,3-a][1,4]benzodiazepin-4-yl]-N-1,3-thi-
azol-2-ylacetamide;
2-[(4S)-6-(4-chlorophenyl)-1-methyl-8-(methyloxy)-4H-[1,
2,4]triazolo[4,3-a][1,4]benzodiazepin-4-yl]-N-2-pyridi-
nylacetamide;
N-(4-azidophenyl)-2-[(4S)-6-(4-chlorophenyl)-1-methyl-8-
(methyloxy)-4H-[1,2,4]triazolo[4,3-a][1,4]benzodiaz-
epin-4-yl]acetamide;
2-[6-(4-chlorophenyl)-1-methyl-8-(methyloxy)-4H-[1,2,4]
triazolo[4,3-a][1,4]benzodiazepin-4-yl]-N-(tetrahydro-2-
furanylmethyl)acetamide;
2-[(4S)-6-(4-chlorophenyl)-1-methyl-8-(methyloxy)-4H-[1,
2,4]triazolo[4,3-a][1,4]benzodiazepin-4-yl]-N-(9-oxo-
9H-fluoren-2-yl)acetamide;
2-[(4S)-6-(4-chlorophenyl)-1-methyl-8-(methyloxy)-4H-[1,
2,4]triazolo[4,3-a][1,4]benzodiazepin-4-yl]-N-[3-(phe-
nylcarbonyl)phenyl]acetamide;
2-[(4S)-6-(4-chlorophenyl)-1-methyl-8-(methyloxy)-4H-[1,
2,4]triazolo[4,3-a][1,4]benzodiazepin-4-yl]-N-{[4-(phe-
nylcarbonyl)phenyl]methyl}acetamide;
2-[(4S)-6-(4-chlorophenyl)-1-methyl-8-(methyloxy)-4H-[1,
2,4]triazolo[4,3-a][1,4]benzodiazepin-4-yl]-N-[4-iodo-2-
(phenylcarbonyl)phenyl]acetamide;
2-[(4S)-6-(4-chlorophenyl)-1-methyl-8-(methyloxy)-4H-[1,
2,4]triazolo[4,3-a][1,4]benzodiazepin-4-yl]-N-(4-{[4-
(methyloxy)phenyl]carbonyl}phenyl)acetamide;
2-[(4S)-6-(4-chlorophenyl)-1-methyl-8-(methyloxy)-4H-
[1,2,4]triazolo[4,3-a][1,4]benzodiazepin-4-yl]-N-(9-oxo-
9H-fluoren-1-yl)acetamide;
2-[(4S)-6-(4-chlorophenyl)-1-methyl-8-(methyloxy)-4H-[1,
2,4]triazolo[4,3-a][1,4]benzodiazepin-4-yl]-N-{4-[(4-io-
dophenyl)carbonyl]phenyl}acetamide;
6-(4-chlorophenyl)-1-methyl-8-(methyloxy)-4-[2-(4-mor-
pholinyl)-2-oxoethyl]-4H-[1,2,4]triazolo[4,3-a][1,4]ben-
zodiazepine;
N-(1,3-benzodioxol-5-ylmethyl)-2-[6-(4-chlorophenyl)-1-
methyl-8-(methyloxy)-4H-[1,2,4]triazolo[4,3-a][1,4]ben-
zodiazepin-4-yl]acetamide;
2-[(4S)-6-(4-chlorophenyl)-1-methyl-8-(methyloxy)-4H-[1,
2,4]triazolo[4,3-a][1,4]benzodiazepin-4-yl]-N-[(1S)-1-
phenylethyl]acetamide;
2-[(4S)-6-(4-chlorophenyl)-1-methyl-8-(methyloxy)-4H-[1,
2,4]triazolo[4,3-a][1,4]benzodiazepin-4-yl]-N-[(1R)-1-
phenylethyl]acetamide;
2-[(4S)-6-(4-chlorophenyl)-1-methyl-8-(methyloxy)-4H-[1,
2,4]triazolo[4,3-a][1,4]benzodiazepin-4-yl]-N-ethylacet-
amide;
2-[(4S)-6-(4-chlorophenyl)-1-methyl-8-(methyloxy)-4H-[1,
2,4]triazolo[4,3-a][1,4]benzodiazepin-4-yl]-N-(cyclopro-
pylmethyl)acetamide;
methyl [(4S)-6-(4-chlorophenyl)-1-methyl-8-(methyloxy)-
4H-[1,2,4]triazolo[4,3-a][1,4]benzodiazepin-4-yl]acetate;
2-[(4S)-6-(3-fluorophenyl)-1-methyl-8-(methyloxy)-4H-[1,
2,4]triazolo[4,3-a][1,4]benzodiazepin-4-yl]-N-(4-fluoro-
phenyl)acetamide;
2-[(4S)-6-(3-fluorophenyl)-1-methyl-8-(methyloxy)-4H-[1,
2,4]triazolo[4,3-a][1,4]benzodiazepin-4-yl]-N-ethylacet-
amide;
2-[6-(4-chlorophenyl)-8-hydroxy-1-methyl-4H-[1,2,4]tri-
azolo[4,3-a][1,4]benzodiazepin-4-yl]-N-(4-fluorophenyl)
acetamide;
ethyl [(4S)-6-(4-chlorophenyl)-1-methyl-8-(methyloxy)-
4H-[1,2,4]triazolo[4,3-a][1,4]benzodiazepin-4-yl]acetate;
1-methylethyl [(4S)-6-(4-chlorophenyl)-1-methyl-8-(meth-
yloxy)-4H-[1,2,4]triazolo[4,3-a][1,4]benzodiazepin-4-yl]
acetate;
butyl [(4S)-6-(4-chlorophenyl)-1-methyl-8-(methyloxy)-
4H-[1,2,4]triazolo[4,3-a][1,4]benzodiazepin-4-yl]acetate;
2-[6-(4-chlorophenyl)-1-methyl-8-(methyloxy)-4H-[1,2,4]
triazolo[4,3-a][1,4]benzodiazepin-4-yl]-N-[2-(methyl-
amino)ethyl]acetamide;
2-[6-(4-chlorophenyl)-1-methyl-8-(methyloxy)-4H-[1,2,4]
triazolo[4,3-a][1,4]benzodiazepin-4-yl]-N-4-piperidiny-
lacetamide;
1-{[(4S)-6-(4-chlorophenyl)-1-methyl-8-(methyloxy)-4H-
[1,2,4]triazolo[4,3-a][1,4]benzodiazepin-4-yl]acetyl}-N-
methyl-4-piperidinamine;
(S)-1-(4-aminopiperidin-1-yl)-2-(6-(4-chlorophenyl)-8-
methoxy-1-methyl-4H-benzo[f][1,2,4]triazolo[4,3-a][1,
4]diazepin-4-yl)ethanone;
(S)—N-(azetidin-3-yl)-2-(6-(4-chlorophenyl)-8-methoxy-1-
methyl-4H-benzo[f][1,2,4]triazolo[4,3-a][1,4]diazepin-4-
yl)acetamide;
(S)-1-(3-aminoazetidin-1-yl)-2-(6-(4-chlorophenyl)-8-
methoxy-1-methyl-4H-benzo[f][1,2,4]triazolo[4,3-a][1,
4]diazepin-4-yl)ethanone;
(S)-2-(6-(4-chlorophenyl)-8-methoxy-1-methyl-4H-benzo
[f][1,2,4]triazolo[4,3-a][1,4]diazepin-4-yl)-1-(4-hy-
droxypiperidin-1-yl)ethanone;
2-[(4S)-6-(4-chlorophenyl)-1-methyl-8-(methyloxy)-4H-[1,
2,4]triazolo[4,3-a][1,4]benzodiazepin-4-yl]-N-[2-(4-mor-
pholinyl)ethyl]acetamide;
2-[(4S)-6-(4-chlorophenyl)-1-methyl-8-(methyloxy)-4H-[1,
2,4]triazolo[4,3-a][1,4]benzodiazepin-4-yl]-N-[2-(1H-
imidazol-4-yl)ethyl]acetamide;
(S)-tert-butyl-2-(6-(4-chlorophenyl)-8-methoxy-1-methyl-
4H-benzo[f][1,2,4]triazolo[4,3-a][1,4]diazepin-4-yl)ac-
etate; and
(S)-piperidin-4-yl-2-(6-(4-chlorophenyl)-8-methoxy-1-
methyl-4H-benzo[f][1,2,4]triazolo[4,3-a][1,4]diazepin-4-
yl)acetate;
or a salt thereof.

In another embodiment, examples of compounds of the present invention include:
2-[6-(4-chlorophenyl)-1-methyl-8-(methyloxy)-4H-[1,2,4]
triazolo[4,3-a][1,4]benzodiazepin-4-yl]-N-(2-phenyl-
ethyl)acetamide;
6-(4-chlorophenyl)-1-methyl-8-(methyloxy)-4-[2-oxo-2-(1-
piperidinyl)ethyl]-4H-[1,2,4]triazolo[4,3-a][1,4]benzodi-
azepine;
2-[6-(4-chlorophenyl)-1-methyl-8-(methyloxy)-4H-[1,2,4]
triazolo[4,3-a][1,4]benzodiazepin-4-yl]-N-(2-furanylm-
ethyl)acetamide;
2-[6-(4-chlorophenyl)-1-methyl-8-(methyloxy)-4H-[1,2,4]
triazolo[4,3-a][1,4]benzodiazepin-4-yl]-N-cyclohexylac-
etamide;
2-[6-(4-chlorophenyl)-1-methyl-8-(methyloxy)-4H-[1,2,4]
triazolo[4,3-a][1,4]benzodiazepin-4-yl]-N-(2,2,2-trifluo-
roethyl)acetamide;

2-[(4S)-6-(4-chlorophenyl)-1-methyl-8-(methyloxy)-4H-[1,2,4]triazolo[4,3-a][1,4]benzodiazepin-4-yl]-N-(3-fluorophenyl)acetamide;

2-[(4S)-6-(4-chlorophenyl)-1-methyl-8-(methyloxy)-4H-[1,2,4]triazolo[4,3-a][1,4]benzodiazepin-4-yl]-N-(4-fluorophenyl)acetamide;

2-[(4S)-6-(4-chlorophenyl)-1-methyl-8-(methyloxy)-4H-[1,2,4]triazolo[4,3-a][1,4]benzodiazepin-4-yl]-N-(4-fluorophenyl)acetamide;

2-[(4S)-6-(4-chlorophenyl)-1-methyl-8-(methyloxy)-4H-[1,2,4]triazolo[4,3-a][1,4]benzodiazepin-4-yl]-N-4-pyridinylacetamide;

2-[(4S)-6-(4-chlorophenyl)-1-methyl-8-(methyloxy)-4H-[1,2,4]triazolo[4,3-a][1,4]benzodiazepin-4-yl]-N-3-pyridinylacetamide;

2-[(4S)-6-(4-chlorophenyl)-1-methyl-8-(methyloxy)-4H-[1,2,4]triazolo[4,3-a][1,4]benzodiazepin-4-yl]-N-1,3-thiazol-2-ylacetamide;

2-[(4S)-6-(4-chlorophenyl)-1-methyl-8-(methyloxy)-4H-[1,2,4]triazolo[4,3-a][1,4]benzodiazepin-4-yl]-N-2-pyridinylacetamide;

N-(4-azidophenyl)-2-[(4S)-6-(4-chlorophenyl)-1-methyl-8-(methyloxy)-4H-[1,2,4]triazolo[4,3-a][1,4]benzodiazepin-4-yl]acetamide;

2-[6-(4-chlorophenyl)-1-methyl-8-(methyloxy)-4H-[1,2,4]thazolo[4,3-a][1,4]benzodiazepin-4-yl]-N-(tetrahydro-2-furanylmethyl)acetamide;

2-[(4S)-6-(4-chlorophenyl)-1-methyl-8-(methyloxy)-4H-[1,2,4]thazolo[4,3-a][1,4]benzodiazepin-4-yl]-N-(9-oxo-9H-fluoren-2-yl)acetamide;

2-[(4S)-6-(4-chlorophenyl)-1-methyl-8-(methyloxy)-4H-[1,2,4]thazolo[4,3-a][1,4]benzodiazepin-4-yl]-N-[3-(phenylcarbonyl)phenyl]acetamide;

2-[(4S)-6-(4-chlorophenyl)-1-methyl-8-(methyloxy)-4H-[1,2,4]thazolo[4,3-a][1,4]benzodiazepin-4-yl]-N-{[4-(phenylcarbonyl)phenyl]methyl}acetamide;

2-[(4S)-6-(4-chlorophenyl)-1-methyl-8-(methyloxy)-4H-[1,2,4]thazolo[4,3-a][1,4]benzodiazepin-4-yl]-N-[4-iodo-2-(phenylcarbonyl)phenyl]acetamide;

2-[(4S)-6-(4-chlorophenyl)-1-methyl-8-(methyloxy)-4H-[1,2,4]triazolo[4,3-a][1,4]benzodiazepin-4-yl]-N-(4-{[4-(methyloxy)phenyl]carbonyl}phenyl)acetamide;

2-[(4S)-6-(4-chlorophenyl)-1-methyl-8-(methyloxy)-4H-[1,2,4]triazolo[4,3-a][1,4]benzodiazepin-4-yl]-N-(9-oxo-9H-fluoren-1-yl)acetamide;

2-[(4S)-6-(4-chlorophenyl)-1-methyl-8-(methyloxy)-4H-[1,2,4]triazolo[4,3-a][1,4]benzodiazepin-4-yl]-N-{4-[(4-iodophenyl)carbonyl]phenyl}acetamide;

6-(4-chlorophenyl)-1-methyl-8-(methyloxy)-4-[2-(4-morpholinyl)-2-oxoethyl]-4H-[1,2,4]thazolo[4,3-a][1,4]benzodiazepine;

N-(1,3-benzodioxol-5-ylmethyl)-2-[6-(4-chlorophenyl)-1-methyl-8-(methyloxy)-4H-[1,2,4]triazolo[4,3-a][1,4]benzodiazepin-4-yl]acetamide;

2-[(4S)-6-(4-chlorophenyl)-1-methyl-8-(methyloxy)-4H-[1,2,4]triazolo[4,3-a][1,4]benzodiazepin-4-yl]-N-[(1S)-1-phenylethyl]acetamide;

2-[(4S)-6-(4-chlorophenyl)-1-methyl-8-(methyloxy)-4H-[1,2,4]thazolo[4,3-a][1,4]benzodiazepin-4-yl]-N-[(1R)-1-phenylethyl]acetamide;

2-[(4S)-6-(4-chlorophenyl)-1-methyl-8-(methyloxy)-4H-[1,2,4]thazolo[4,3-a][1,4]benzodiazepin-4-yl]-N-ethylacetamide;

2-[(4S)-6-(4-chlorophenyl)-1-methyl-8-(methyloxy)-4H-[1,2,4]triazolo[4,3-a][1,4]benzodiazepin-4-yl]N-(cyclopropylmethyl)acetamide;

methyl [(4S)-6-(4-chlorophenyl)-1-methyl-8-(methyloxy)-4H-[1,2,4]triazolo[4,3-a][1,4]benzodiazepin-4-yl]acetate;

2-[(4S)-6-(3-fluorophenyl)-1-methyl-8-(methyloxy)-4H-[1,2,4]triazolo[4,3-a][1,4]benzodiazepin-4-yl]-N-(4-fluorophenyl)acetamide;

2-[(4S)-6-(3-fluorophenyl)-1-methyl-8-(methyloxy)-4H-[1,2,4]triazolo[4,3-a][1,4]benzodiazepin-4-yl]-N-ethylacetamide;

2-[6-(4-chlorophenyl)-8-hydroxy-1-methyl-4H-[1,2,4]triazolo[4,3-a][1,4]benzodiazepin-4-yl]-N-(4-fluorophenyl)acetamide;

ethyl [(4S)-6-(4-chlorophenyl)-1-methyl-8-(methyloxy)-4H-[1,2,4]triazolo[4,3-a][1,4]benzodiazepin-4-yl]acetate;

1-methylethyl [(4S)-6-(4-chlorophenyl)-1-methyl-8-(methyloxy)-4H-[1,2,4]triazolo[4,3-a][1,4]benzodiazepin-4-yl]acetate;

butyl [(4S)-6-(4-chlorophenyl)-1-methyl-8-(methyloxy)-4H-[1,2,4]triazolo[4,3-a][1,4]benzodiazepin-4-yl]acetate;

2-[6-(4-chlorophenyl)-1-methyl-8-(methyloxy)-4H-[1,2,4]triazolo[4,3-a][1,4]benzodiazepin-4-yl]-N-[2-(methylamino)ethyl]acetamide; and 2-[6-(4-chlorophenyl)-1-methyl-8-(methyloxy)-4H-[1,2,4]triazolo[4,3-a][1,4]benzodiazepin-4-yl]-N-4-piperidinylacetamide;

or a salt thereof.

In a further embodiment, examples of compounds of the present invention include:

2-[(4S)-6-(4-chlorophenyl)-1-methyl-8-(methyloxy)-4H-[1,2,4]triazolo[4,3-a][1,4]benzodiazepin-4-yl]-N-ethylacetamide;

2-[6-(4-chlorophenyl)-1-methyl-8-(methyloxy)-4H-[1,2,4]triazolo[4,3-a][1,4]benzodiazepin-4-yl]-N-(2-phenylethyl)acetamide;

2-[6-(4-chlorophenyl)-1-methyl-8-(methyloxy)-4H-[1,2,4]triazolo[4,3-a][1,4]benzodiazepin-4-yl]-N-(2-furanylmethyl)acetamide;

2-[(4S)-6-(4-chlorophenyl)-1-methyl-8-(methyloxy)-4H-[1,2,4]triazolo[4,3-a][1,4]benzodiazepin-4-yl]-N-(2-fluorophenyl)acetamide;

2-[(4S)-6-(4-chlorophenyl)-1-methyl-8-(methyloxy)-4H-[1,2,4]triazolo[4,3-a][1,4]benzodiazepin-4-yl]-N-(3-fluorophenyl)acetamide;

2-[(4S)-6-(4-chlorophenyl)-1-methyl-8-(methyloxy)-4H-[1,2,4]triazolo[4,3-a][1,4]benzodiazepin-4-yl]-N-(4-fluorophenyl)acetamide;

2-[(4S)-6-(4-chlorophenyl)-1-methyl-8-(methyloxy)-4H-[1,2,4]triazolo[4,3-a][1,4]benzodiazepin-4-yl]-N-2-pyridinylacetamide;

2-[(4S)-6-(4-chlorophenyl)-1-methyl-8-(methyloxy)-4H-[1,2,4]triazolo[4,3-a][1,4]benzodiazepin-4-yl]-N-3-pyridinylacetamide;

2-[(4S)-6-(4-chlorophenyl)-1-methyl-8-(methyloxy)-4H-[1,2,4]triazolo[4,3-a][1,4]benzodiazepin-4-yl]-N-4-pyridinylacetamide;

2-[(4S)-6-(4-chlorophenyl)-1-methyl-8-(methyloxy)-4H-[1,2,4]triazolo[4,3-a][1,4]benzodiazepin-4-yl]-N-1,3-thiazol-2-ylacetamide;

2-[(4S)-6-(4-chlorophenyl)-1-methyl-8-(methyloxy)-4H-[1,2,4]triazolo[4,3-a][1,4]benzodiazepin-4-yl]-N-(cyclopropylmethyl)acetamide;

2-[(4S)-6-(4-chlorophenyl)-1-methyl-8-(methyloxy)-4H-[1,2,4]triazolo[4,3-a][1,4]benzodiazepin-4-yl]-N-[(1S)-1-phenylethyl]acetamide;

2-[(4S)-6-(4-chlorophenyl)-1-methyl-8-(methyloxy)-4H-[1,2,4]triazolo[4,3-a][1,4]benzodiazepin-4-yl]-N-{[4-(phenylcarbonyl)phenyl]methyl}acetamide;

N-ethyl-2-[(4S)-6-(3-fluorophenyl)-1-methyl-8-(methyloxy)-4H-[1,2,4]triazolo[4,3-a][1,4]benzodiazepin-4-yl]acetamide;

N-(4-fluorophenyl)-2-[(4S)-6-(3-fluorophenyl)-1-methyl-8-(methyloxy)-4H-[1,2,4]triazolo[4,3-a][1,4]benzodiazepin-4-yl]acetamide;

2-[6-(4-chlorophenyl)-1-methyl-8-(methyloxy)-4H-[1,2,4]triazolo[4,3-a][1,4]benzodiazepin-4-yl]-N-[2-(dimethylamino)ethyl]acetamide;

methyl-[(4S)-6-(4-chlorophenyl)-1-methyl-8-(methyloxy)-4H-[1,2,4]triazolo[4,3-a][1,4]benzodiazepin-4-yl]acetate;

1-methylethyl [(4S)-6-(4-chlorophenyl)-1-methyl-8-(methyloxy)-4H-[1,2,4]triazolo[4,3-a][1,4]benzodiazepin-4-yl]acetate;

butyl-[(4S)-6-(4-chlorophenyl)-1-methyl-8-(methyloxy)-4H-[1,2,4]triazolo[4,3-a][1,4]benzodiazepin-4-yl]acetate;

2-[(4S)-6-(4-chlorophenyl)-1-methyl-8-(methyloxy)-4H-[1,2,4]triazolo[4,3-a][1,4]benzodiazepin-4-yl]N-[2-(methylamino)ethyl]acetamide;

2-[(4S)-6-(4-chlorophenyl)-1-methyl-8-(methyloxy)-4H-[1,2,4]triazolo[4,3-a][1,4]benzodiazepin-4-yl]-N-4-piperidinylacetamide;

1-{[(4S)-6-(4-chlorophenyl)-1-methyl-8-(methyloxy)-4H-[1,2,4]triazolo[4,3-a][1,4]benzodiazepin-4-yl]acetyl}-N-methyl-4-piperidinamine;

1-{[(4S)-6-(4-chlorophenyl)-1-methyl-8-(methyloxy)-4H-[1,2,4]triazolo[4,3-a][1,4]benzodiazepin-4-yl]acetyl}-4-piperidinamine;

N-3-azetidinyl-2-[(4S)-6-(4-chlorophenyl)-1-methyl-8-(methyloxy)-4H-[1,2,4]triazolo[4,3-a][1,4]benzodiazepin-4-yl]acetamide;

1-{[(4S)-6-(4-chlorophenyl)-1-methyl-8-(methyloxy)-4H-[1,2,4]triazolo[4,3-a][1,4]benzodiazepin-4-yl]acetyl}-3-azetidinamine;

(S)-2-(6-(4-chlorophenyl)-8-methoxy-1-methyl-4H-benzo[f][1,2,4]triazolo[4,3-a][1,4]diazepin-4-yl)-1-(4-hydroxypiperidin-1-yl)ethanone;

2-[(4S)-6-(4-chlorophenyl)-1-methyl-8-(methyloxy)-4H-[1,2,4]triazolo[4,3-a][1,4]benzodiazepin-4-yl]-N-[2-(4-morpholinyl)ethyl]acetamide;

2-[(4S)-6-(4-chlorophenyl)-1-methyl-8-(methyloxy)-4H-[1,2,4]triazolo[4,3-a][1,4]benzodiazepin-4-yl]-N-[2-(1H-imidazol-4-yl)ethyl]acetamide;

(S)-tert-butyl-2-(6-(4-chlorophenyl)-8-methoxy-1-methyl-4H-benzo[f][1,2,4]triazolo[4,3-a][1,4]diazepin-4-yl)acetate;

(S)-piperidin-4-yl-2-(6-(4-chlorophenyl)-8-methoxy-1-methyl-4H-benzo[f][1,2,4]triazolo[4,3-a][1,4]diazepin-4-yl)acetate;

2-[(4S)-6-(4-chlorophenyl)-1-methyl-8-(methyloxy)-4H-[1,2,4]triazolo[4,3-a][1,4]benzodiazepin-4-yl]-N-[2-(dimethylamino)ethyl]acetamide;

2-[(4S)-6-(4-chlorophenyl)-1-methyl-8-(methyloxy)-4H-[1,2,4]triazolo[4,3-a][1,4]benzodiazepin-4-yl]-N-[3-(dimethylamino)propyl]acetamide;

2-[(4S)-6-(4-chlorophenyl)-1-methyl-8-(methyloxy)-4H-[1,2,4]triazolo[4,3-a][1,4]benzodiazepin-4-yl]-N-4-pyrimidinylacetamide;

2-[(4S)-6-(4-chlorophenyl)-1-methyl-8-(methyloxy)-4H-[1,2,4]triazolo[4,3-a][1,4]benzodiazepin-4-yl]-N-(5-methyl-3-isoxazolyl)acetamide;

2-[(4S)-6-(4-chlorophenyl)-1-methyl-8-(methyloxy)-4H-[1,2,4]triazolo[4,3-a][1,4]benzodiazepin-4-yl]-N-(tetrahydro-2H-pyran-4-yl)acetamide;

[4-(methyloxy)phenyl]methyl-[(4S)-6-(4-chlorophenyl)-1-methyl-8-(methyloxy)-4H-[1,2,4]triazolo[4,3-a][1,4]benzodiazepin-4-yl]acetate;

2-methylpropyl-[(4S)-6-(4-chlorophenyl)-1-methyl-8-(methyloxy)-4H-[1,2,4]triazolo[4,3-a][1,4]benzodiazepin-4-yl]acetate;

tetrahydro-2H-pyran-4-yl-[(4S)-6-(4-chlorophenyl)-1-methyl-8-(methyloxy)-4H-[1,2,4]triazolo[4,3-a][1,4]benzodiazepin-4-yl]acetate;

2-[6-(4-chlorophenyl)-1-methyl-8-(methyloxy)-4H-[1,2,4]triazolo[4,3-a][1,4]benzodiazepin-4-yl]-N-4-pyridinylacetamide;

2-[6-(4-chlorophenyl)-1-methyl-8-(methyloxy)-4H-[1,2,4]triazolo[4,3-a][1,4]benzodiazepin-4-yl]-N-(cyclopropylmethyl)acetamide;

2-[6-(4-chlorophenyl)-1-methyl-4H-[1,2,4]triazolo[4,3-a][1,4]benzodiazepin-4-yl]-N-4-pyridinylacetamide;

2-[6-(4-chlorophenyl)-1-methyl-8-(methyloxy)-4H-[1,2,4]triazolo[4,3-a][1,4]benzodiazepin-4-yl]-N-1,3-thiazol-2-ylacetamide; and methyl-[6-(4-chlorophenyl)-1-methyl-4H-[1,2,4]triazolo[4,3-a][1,4]benzodiazepin-4-yl]acetate; or a salt thereof.

In one embodiment of the invention, there is provided a compound which is 2-[(4S)-6-(4-chlorophenyl)-1-methyl-8-(methyloxy)-4H-[1,2,4]triazolo[4,3-a][1,4]benzodiazepin-4-yl]-N-ethylacetamide or a salt thereof. In another embodiment there is provided a compound which is 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof. In a further embodiment there is provided a compound which is 2-[(4S)-6-(4-chlorophenyl)-1-methyl-8-(methyloxy)-4H-[1,2,4]triazolo[4,3-a][1,4]benzodiazepin-4-yl]-N-ethylacetamide.

It will be appreciated that the present invention covers compounds of formula (I) as the free base and as salts thereof, for example as a pharmaceutically acceptable salt thereof. In one embodiment the invention relates relates to compounds of formula (I) as the free base. In another embodiment the invention to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of formula (I) can comprise or be, for example, a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example, in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compounds of formula (I) and pharmaceutically acceptable salts thereof, which upon administration to the recipient are capable of providing (directly or indirectly) a compound of formula (I) or a pharmaceutically acceptable salt thereof, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain of the compounds described herein may contain one or more chiral atoms so that optical isomers, e.g.— enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures).

Similarly the invention also extends to conformational isomers of compounds of formula (I) and any geometric (cis and/or trans) isomers of said compounds.

An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula (I) and pharmaceutically acceptable salts thereof may be made by a variety of methods, including standard chemistry. Any previously defined variable will continue to have the previously defined meaning unless otherwise indicated. Illustrative general synthetic methods are set out below and then specific compounds of formula (I) and pharmaceutically acceptable salts thereof are prepared in the working Examples. These processes form further aspects of the present invention.

Throughout the specification, general formulae are designated by Roman numerals (I), (II), (III), (IV) etc. Subsets of these general formulae are defined as (Ia), (Ib), (Ic) etc.

Compounds of formula (Ic), i.e. compounds of general formula (I) where $R^2$ is $OR^{2b}$, may be prepared according to reaction scheme 1 by reacting compounds of formula (Id), i.e.

compounds of general formula (I) where $R^2$ is OH, with $R^{2b}$OH in the presence of DIC and DMAP at room temperature. Alternatively compounds of formula (Ic) may be prepared by reacting compounds of formula (Id) with oxalyl chloride followed by addition of $R^{2b}$OH.

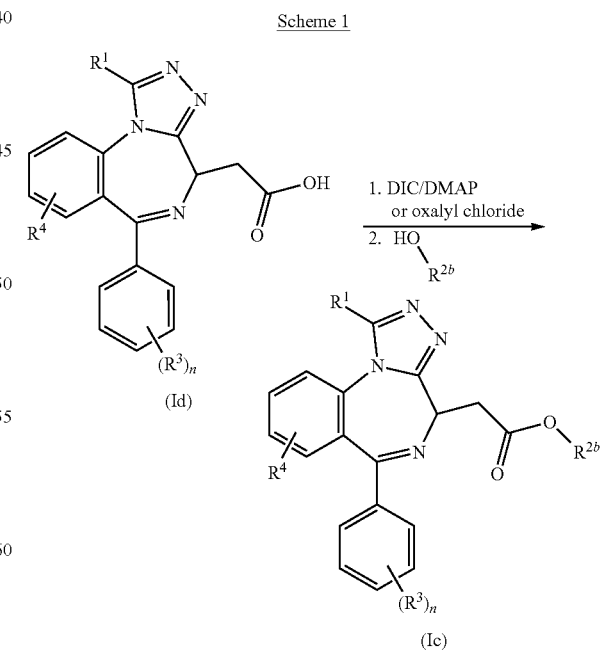

Scheme 1

Compounds of formula (Ie), i.e. compounds of general formula (I) where $R^2$ is $NR^{2a}R^{2'a}$, may be prepared according to reaction scheme 2 by reacting compounds of formula (Id), i.e. compounds of general formula (I) where $R^2$ is OH, with $R^{2a}R^{2'a}NH$, in the presence of HATU or HBTU and DIEA at room temperature. Alternatively compounds of formula (Ie) may be prepared by reacting compounds of formula (Id) with oxalyl chloride followed by addition of $R^{2a}R^{2'a}NH$ in the presence of triethylamine.

Scheme 2

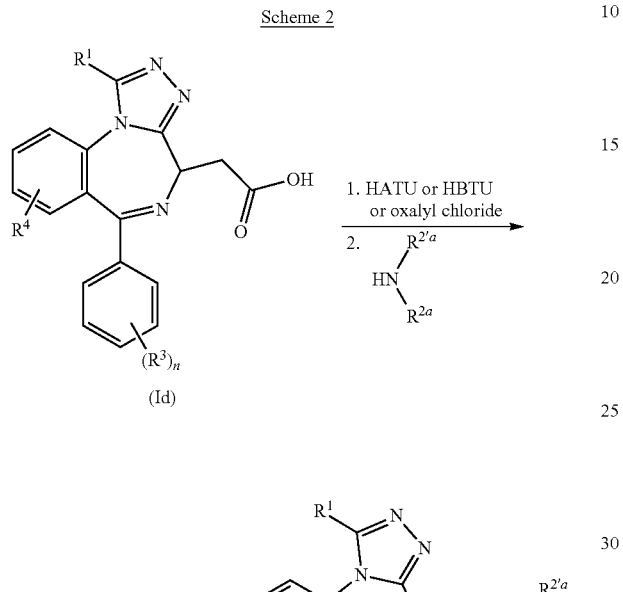

(Id)

(Ie)

Alternatively compounds of formula (Ie), i.e. compounds of general formula (I) where $R^2$ is $NR^{2a}R^{2'a}$, may be prepared according to reaction scheme 3 by reacting compounds of formula (III) with hydrazine followed by reaction of the resulting hydrazone (II) with $R^1C(OR)_3$. Preferably hydrazone (II) is used without further purification and is reacted with $R^1C(OR)_3$.

Scheme 3

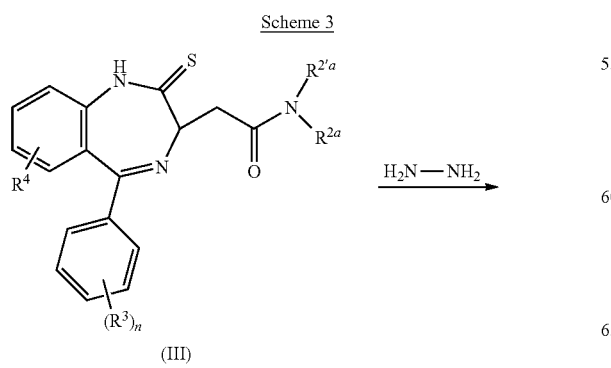

(III)

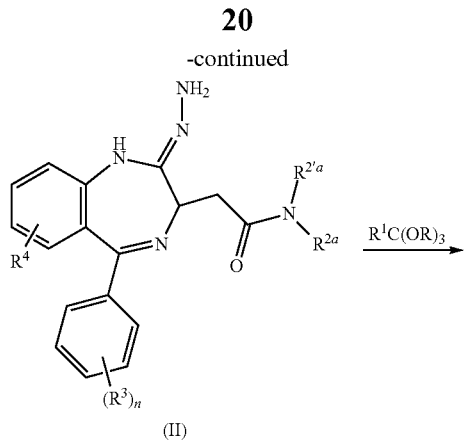

(II)

(Ie)

wherein R represents $C_{1-4}$alkyl such as methyl.

Compounds of formula (Id), i.e. compounds of general formula (I) where $R^2$ is OH, may be prepared according to reaction scheme 4. Suitable reaction conditions comprise reacting compounds of formula (Ic), i.e. compounds of general formula (I) where $R^2$ is $OR^{2b}$, with alkaline hydroxide preferably sodium hydroxide or lithium hydroxide.

Scheme 4

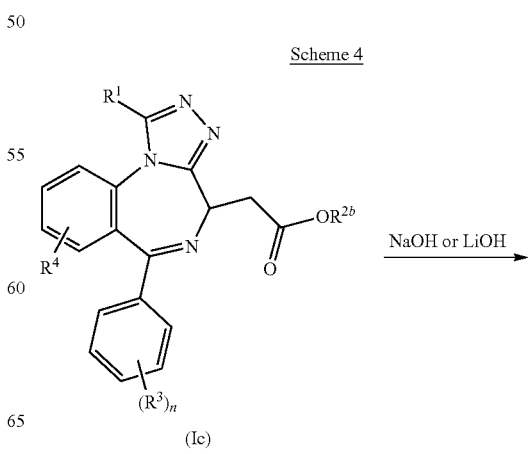

(Ic)

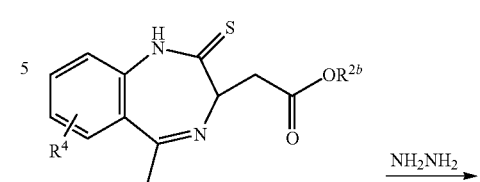

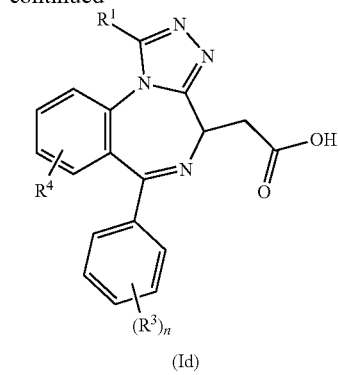

(Id)

Compounds of formula (Ic), i.e. compounds of general formula (I) where $R^2$ is $OR^{2b}$ may be prepared according to reaction scheme 5 by reacting compounds of formula (IV) with AcOH.

Scheme 5

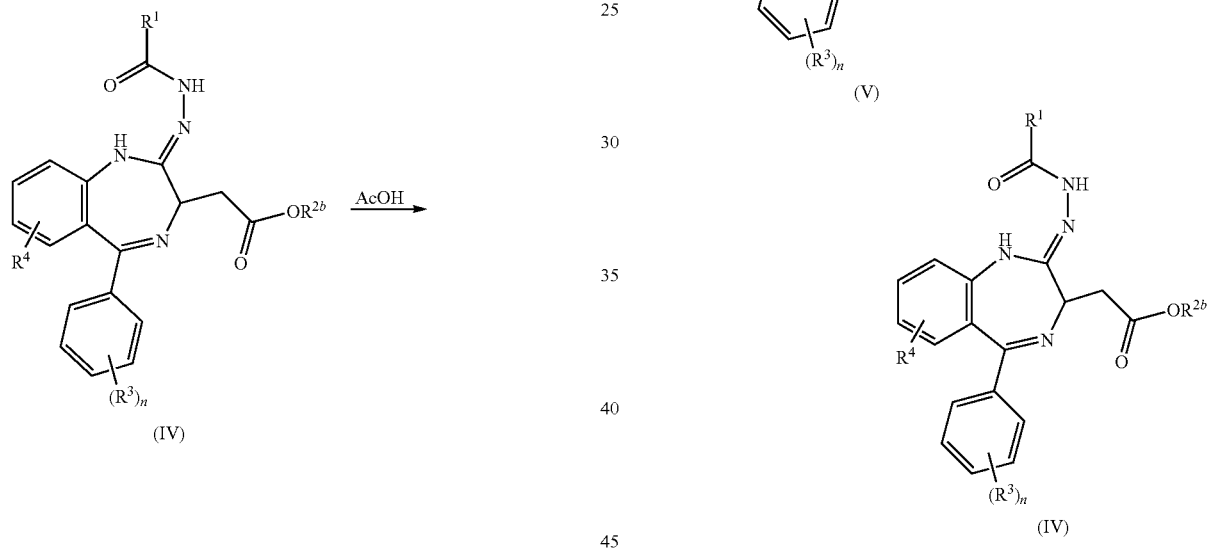

Compounds of formula (IV) may be prepared according to reaction scheme 6 by reacting compounds of formula (VI) with hydrazine below 15 °C. followed by reaction of the resulting hydrazone (V) with $R^1COCl$ at 0° C. Generally hydrazone (V) is used without further purification and is reacted with $R^1COCl$ at, for example 0° C.

Scheme 6

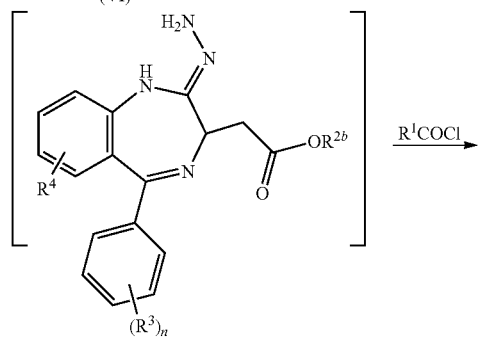

Compounds of formula (III) may be prepared according to reaction scheme 7 by reacting compounds of formula (VII) with $R^{2a}R^{2'a}NH$ in the presence of HATU and DIEA at, for example room temperature.

Scheme 7

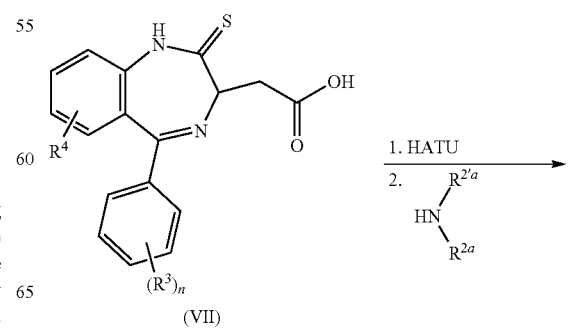

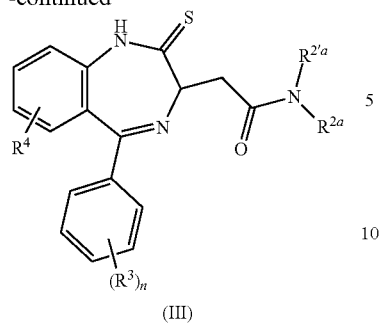

(III)

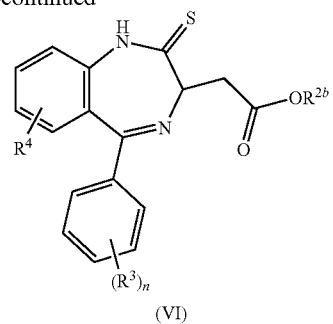

(VI)

Compounds of formula (VII) may be prepared according to reaction scheme 8. Suitable reaction conditions comprise reacting compounds of formula (VI) with alkaline hydroxide such as sodium hydroxide.

Compounds of formula (VIII) may be prepared according to reaction scheme 10, by reacting compounds of formula (X) with an organic base such as triethylamine followed by reaction of the resulting amine (IX) with acetic acid. Generally, amine (IX) is used without further purification and is reacted with AcOH at, for example 60° C.

Scheme 8

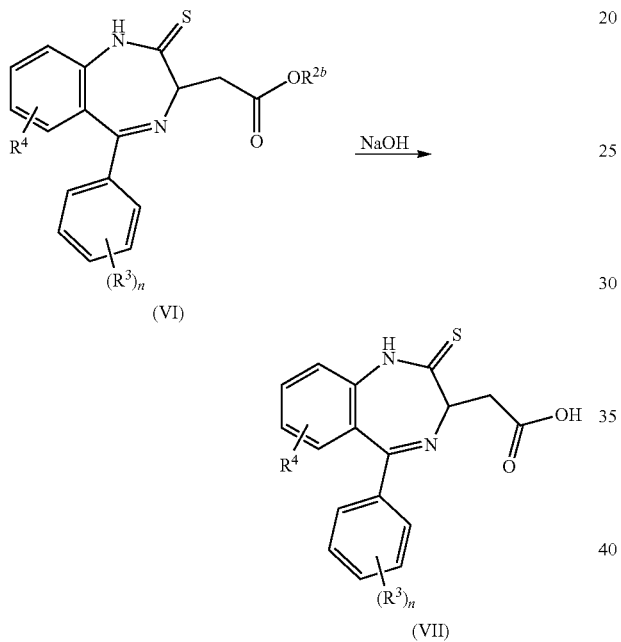

Scheme 10

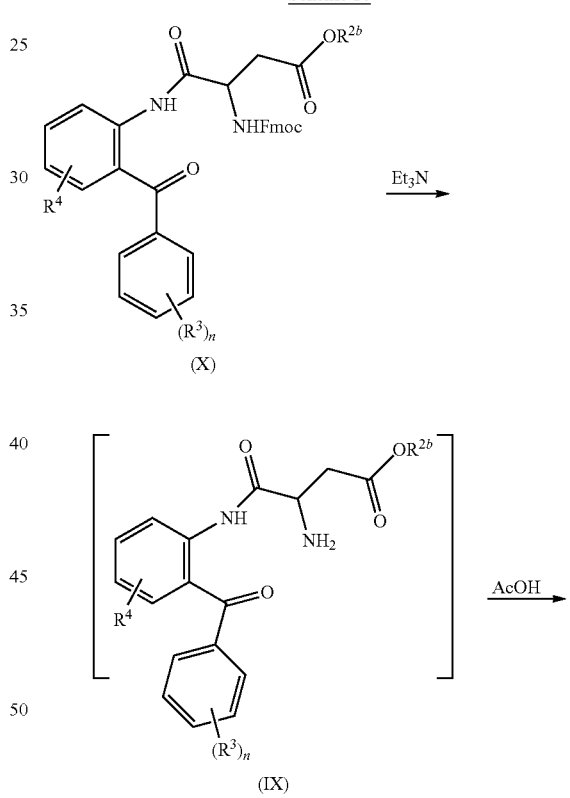

Compounds of formula (VI) may be prepared according to reaction scheme 9 from compounds of formula (VIII) by treatment with Lawesson's reagent or $P_4S_{10}$. Suitable reaction conditions comprise reacting compounds of formula (VIII) with $P_4S_{10}$ in 1,2-dichloroethane at, for example 70° C.

Scheme 9

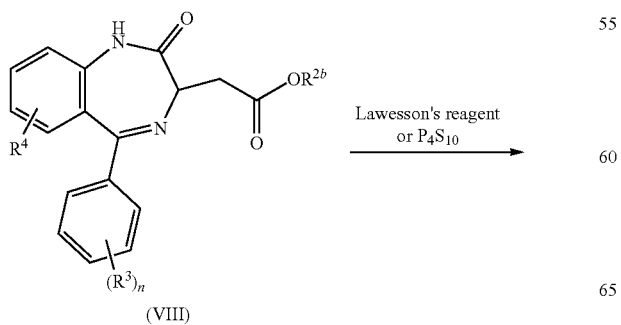

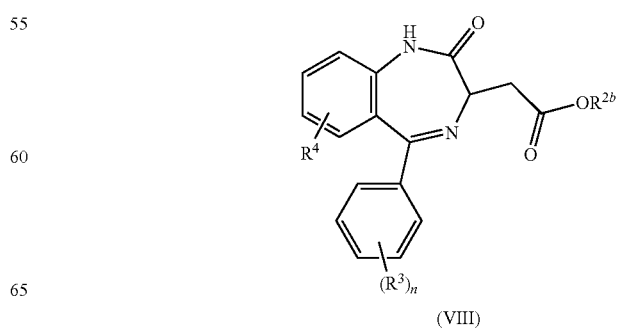

Compounds of formula (X) may be prepared according to reaction scheme 11, by reacting compounds of formula (XI) with the acylchloride (XII) derived from protected aspartic acid.

Scheme 11

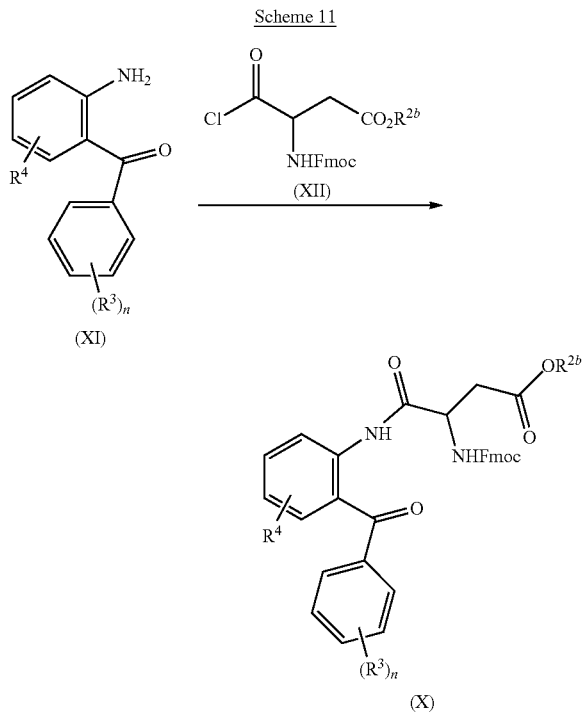

Compounds of formula (XI) may be prepared according to procedures described in *Synthesis* 1980, 677-688.

Acyl chlorides (XII) may be prepared according to procedures described in J. Org. Chem., 1990, 55, 3068-3074 and J. Chem. Soc. Perkin Trans. 1, 2001, 1673-1695

It will be appreciated by those skilled in the art that it may be advantageous to protect one or more functional groups of the compounds described in the above processes. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above are believed to be novel and therefore form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. In one embodiment there is provided 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof for use in therapy. The compounds of formula (I) or pharmaceutically salts thereof can be for use in the treatment of diseases or conditions for which a bromodomain inhibitor indicated.

In one embodiment there is provided a compound of formula (I) or a pharmaceutically acceptable salt thereof for use in the treatment of diseases or conditions for which a bromodomain inhibitor is indicated. In another embodiment, there is provided a compound or a pharmaceutically acceptable salt thereof for use in the treatment of a chronic autoimmune and/or inflammatory condition. In a further embodiment, there is provided a compound or a pharmaceutically acceptable salt thereof for use in the treatment of cancer, such as midline carcinoma.

In one embodiment there is provided 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof for use in the treatment of diseases or conditions for which a bromodomain inhibitor is indicated. In another embodiment, there is provided 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof for use in the treatment of a chronic autoimmune and/or inflammatory condition. In a further embodiment, there is provided 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof for use in the treatment of cancer, such as midline carcinoma.

In one embodiment there is provided the use of a compound of formula (I) or a pharmaceutically acceptable salt thereof in the manufacture of a medicament for the treatment of diseases or conditions for which a bromodomain inhibitor is indicated. In another embodiment, there is provided the use of a compound of formula (I) or a pharmaceutically acceptable salt thereof in the manufacture of a medicament for the treatment of a chronic autoimmune and/or inflammatory condition. In a further embodiment, there is provided the use of a compound of formula (I) or a pharmaceutically acceptable salt thereof in the manufacture of a medicament for the treatment of cancer, such as midline carcinoma.

In one embodiment there is provided the use of 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof in the manufacture of a medicament for the treatment of diseases or conditions for which a bromodomain inhibitor is indicated. In another embodiment, there is provided the use of 2-[(4S)-6-(4-chlorophenyl)-1-methyl-8-(methyloxy)-4H-[1,2,4]triazolo [4,3-a][1,4]benzodiazepin-4-yl]-N-ethylacetamide or a pharmaceutically acceptable salt thereof in the manufacture of a medicament for the treatment of a chronic autoimmune and/or inflammatory condition. In a further embodiment, there is provided the use of 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof in the manufacture of a medicament for the treatment of cancer, such as midline carcinoma.

In one embodiment there is provided a method for the treatment of a disease or condition, for which a bromodomain inhibitor is indicated, in a subject in need thereof which comprises administering a therapeutically effective amount of compound of formula (I) or a pharmaceutically acceptable salt thereof. In another embodiment there is provided a method for treatment of a chronic autoimmune and/or inflammatory condition, in a subject in need thereof which comprises administering a therapeutically effective amount of compound of formula (I) or a pharmaceutically acceptable salt thereof. In a further embodiment there is provided a method for treatment of cancer, such as midline carcinoma, in a subject in need thereof which comprises administering a therapeutically effective amount of compound of formula (I) or a pharmaceutically acceptable salt thereof.

In one embodiment there is provided a method for treatment of a disease or condition, for which a bromodomain inhibitor is indicated, in a subject in need thereof which comprises administering a therapeutically effective amount of 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof. In another embodiment there is provided a method for treatment of a chronic autoimmune and/or inflammatory condition, in a subject in need thereof which comprises administering a therapeutically effective amount of 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof. In a further embodiment there is provided a method for treatment of cancer, such as midline carcinoma, in a subject in need thereof which comprises administering a therapeutically effective amount of 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof.

In one embodiment the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or acute on chronic pancreatitis. In another embodiment the bromodomain inhibitor is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include any of or all of the above disease states.

In one embodiment, there is provided a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt thereof and one or more pharmaceutically acceptable carriers, diluents or excipients. The compounds of the formula (I) and pharmaceutically acceptable salts thereof, are as described above. In one embodiment there is provided a pharmaceutical composition comprising 2-[(4S)-6-(4-chlorophenyl)-1-methyl-8-(methyloxy)-4H-[1,2,4]triazolo[4,3-a][1,4]benzodiazepin-4-yl]-N-ethylacetamide or a pharmaceutically acceptable salt thereof and one or more pharmaceutically acceptable carriers, diluents or excipients. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein.

Since the compounds of formula (I) and pharmaceutically acceptable salts thereof are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment there is provided a pharmaceutical composition comprising a compound of formula (I) or a pharmaceutically acceptable salt thereof adapted for oral administration.

In one embodiment the pharmaceutical composition is adapted for parenteral administration, particularly intravenous administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Dosage forms for nasal or inhaled administration may conveniently be formulated as aerosols, solutions, suspensions, gels or dry powders.

For compositions suitable and/or adapted for inhaled administration, it is preferred that the compound of formula (I) or pharmaceutically acceptable salt thereof is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or a pharmaceutically acceptable salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO2005/044354 A1.

A therapeutically effective amount of a compound of formula (I) or a pharmaceutically acceptable salt thereof will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The compounds of formula (I) and pharmaceutically acceptable salts thereof can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a pharmaceutically acceptable salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of formula (I) and pharmaceutically acceptable salts thereof, and the other pharmaceutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other pharmaceutically active agent(s) and the relative timings of administration will be selected in order to achieve the desired combined therapeutic effect. Thus in a further aspect, there is provided a combination comprising a compound of formula (I) or pharmaceutically acceptable salt thereof and at least one other pharmaceutically active agent. In one embodiment there is provided a combination pharmaceutical product comprising a compound of formula (I) or a pharmaceutically acceptable salt thereof together with one or more other therapeutically active agents.

Thus in one aspect, the compounds and pharmaceutical compositions according to the invention may be used in combination with or include one or more other therapeutic agents, for example selected from antibiotics, anti-virals, glucocorticosteroids, muscarinic antagonists and beta-2 agonists.

It will be appreciated that when the compounds of the present invention are administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and salts thereof may be prepared by the methods described below or by similar methods. Thus the following Intermediates and Examples serve to illustrate the preparation of the compounds of formula (I) and salts thereof, and are not to be considered as limiting the scope of the invention in any way.

General Experimental Details

All temperatures referred to are in ° C.
Abbreviations
TLC—thin layer chromatography
AcOH—acetic acid
AcCl—acetyl chloride
PPTS—pyridinium p-toluenesulfonate
DCM—dichloromethane
1,2-DCE—1,2-dichloroethane
DIC—Diisopropylcarbodiimide
DIEA—N,N-diisopropylethylamine
DMF—N,N-dimethylformamide
DMAP—4-dimethylaminopyridine
Fmoc—9H-fluoren-9-ylmethyl)oxy]carbonyl
HATU—O-(7-Azabenzotriazol-1-yl)-N,N,N',N'-tetramethyluronium hexafluorophosphate
HBTU—O-(Benzotriazol-1-yl)-N,N,N',N'-tetramethyluronium hexafluorophosphate
$Et_2O$—diethyl ether
EtOAc—ethyl acetate
i-$Pr_2O$—di-isopropyl ether
Config.—absolute configuration
Lawesson's—2,4-bis(4-methoxyphenyl)-1,3-dithia-2,4-diphosphetane-2,4-disulphide Reagent
MeCN—acetonitrile
MeOH—methanol
Rt—retention time
THF—tetrahydrofuran
RT—room temperature
Pd/C—palladium on carbon
COMU—1-cyano-2-ethoxy-2-oxoethylidenaminooxy)dimethylamino-morpholino-carbenium hexafluorophosphate
LC/MS refers to analyses by analytical HPLC which were conducted on three kinds of apparatus:
a) On a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give [M+H]$^+$ and [M+NH$_4$]$^+$ molecular ions] or electrospray negative ionisation [(ES−ve to give [M−H]− molecular ion] modes. Analytical data from this apparatus are given with the following format : [M+H]$^+$ or [M−H]$^−$.

b) On a Chromolith Performance RP 18 column (100×4.6 mm id) eluting with 0.01M ammonium acetate in water (solvent A) and 100% acetonitrile (solvent B), using the following elution gradient 0-4 minutes 0→100% B, 4-5 minutes 100% B at a flow rate of 5 mL/minute. The mass spectra (MS) were recorded on a micromass Platform-LC mass spectrometer using atmospheric pressure chemical positive ionisation [AP+ve to give MH$^+$ molecular ions] or atmospheric pressure chemical negative ionisation [AP−ve to give (M−H)$^−$ molecular ions] modes. Analytical data from this apparatus are given with the following format: [M+H]+ or [M−H]− preceded by the acronym APCI to specify between both mass spectrometry analyses sources.

c) On an Acquity UPLC BEH C18 column (2.1 mm×50 mm id, 1.7 μm packing diameter) at 40° C., eluting with 0.1% v/v solution of formic acid in water (solvent system A) and 0.1% v/v solution of formic acid in acetonitrile (solvent system B). The gradient employed was:

| Time (min) | Flow Rate (ml/min) | Solvent System % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection system was an averaged signal from wavelength of 210 nm to 350 nm and mass spectra were recorded on a mass spectrometer using alternate-scan positive and negative mode electrospray ionization.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 mL/minute. The mass spectra (MS) were recorded on a micromass LCT mass spectrometer using electrospray positive ionisation [ES+ve to give MH$^+$ molecular ions] or electrospray negative ionisation [ES−ve to give (M−H)− molecular ions] modes.

Mass directed auto-prep HPLC refers to the method where the material was purified by high performance liquid chromatography on a HPLCABZ+5 μm column (5 cm×10 mm i.d.) with 0.1% HCO$_2$H in water and 95% MeCN, 5% water (0.5% HCO$_2$H) utilising the following gradient elution conditions: 0-1.0 minutes 5% B, 1.0-8.0 minutes 5→30% B, 8.0-8.9 minutes 30% B, 8.9-9.0 minutes 30→95% B, 9.0-9.9 minutes 95% B, 9.9-10 minutes 95→0% B at a flow rate of 8 mL/minute. The Gilson 202-fraction collector was triggered by a VG Platform Mass Spectrometer on detecting the mass of interest.

Proton NMR ($^1$H NMR) spectra were recorded at ambient temperature on a Bruker Avance 300 DPX spectrometer using solvant as internal standard and proton chemical shifts are expressed in ppm in the indicated solvent. The following abbreviations are used for multiplicity of NMR signals: s=singlet, d=doublet, t=triplet, q=quadruplet, dd=double doublet, m=multiplet.

TLC (thin layer chromatography) refers to the use of TLC plates sold by Merck coated with silica gel 60 F254.

INTERMEDIATE 1

Methyl [(4S)-6-(3-fluorophenyl)-1-methyl-8-(methyloxy)-4H-[1,2,4]triazolo[4,3-a][1,4]benzodiazepin-4-yl]acetate

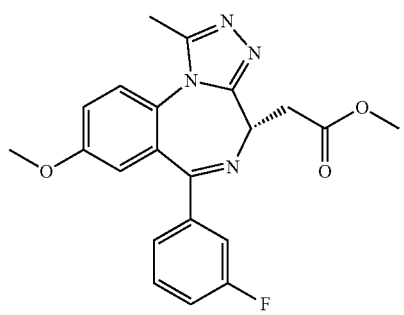

The crude Intermediate 5 (assumed 9.3 mmol) was suspended in a mixture of THF and AcOH (1/1) and stirred overnight before being concentrated under reduced pressure. The crude mixture was suspended in DCM and washed with sat. NaHCO$_3$ solution. The organic layer was dried over Na$_2$SO$_4$, filtered and concentrated in vacuo and the resulting solid was triturated in i-Pr$_2$O and filtered. The crude product was purified by flash-chromatography on silica gel (DCM/MeOH: 95/5) to give the title compound which will be used in the next step without further purification. LC/MS: m/z 395 [M+H]$^+$, Rt 2.71 min.

INTERMEDIATE 2

[(4S)-6-(4-Chlorophenyl)-1-methyl-8-(methyloxy)-4H-[1,2,4]triazolo[4,3-a][1,4]benzodiazepin-4-yl] acetic acid

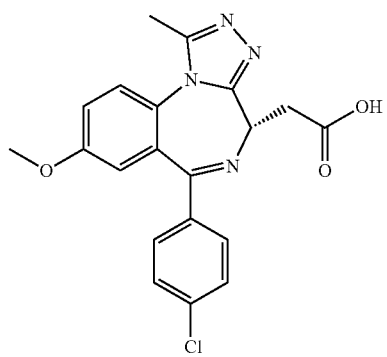 [SMILES: COc1ccc2c(c1)C(c1ccc(Cl)cc1)=N[C@@H](CC(=O)O)c1nnc(C)n1-2]

To a solution of Example 34 (28 g, 68 mmol) in THF (450 mL) at RT was added 1N NaOH (136 mL, 136 mmol). The reaction mixture was stirred at this temperature for 5 h before being cooled down and quenched with 1N HCl (136 mL). THF was removed under reduced pressure and the aqueous layer was extracted with DCM. The combined organic layers were dried over Na$_2$SO$_4$, filtered and concentrated under reduced pressure. The crude solid was recrystallised in CH$_3$CN to give the title compound (23.9 g, 89% yield) as a pale yellow powder. $^1$H NMR (300 MHz, CDCl$_3$) δ7.55-7.48 (m, 2H), 7.41 (d, J=8.9 Hz, 1H), 7.38-7.31 (m, 2H), 7.22 (dd, J=2.9 and 8.9 Hz, 1H), 6.90 (d, J=2.9 Hz, 1H), 4.59 (dd, J=6.9 and 6.9 Hz, 1H), 3.81 (s, 3H), 3.70 (dd, J=6.9 and 25.7 Hz, 1H), 3.61 (dd, J=6.9 and 25.7 Hz, 1H), 2.63 (s, 3H). LC/MS: m/z 397 [M($^{35}$Cl)+H]$^+$, Rt 2.11 min.

Intermediate 3 of formula (Ib), i.e. compounds of general formula (I) where R$^2$ is OH was prepared by methods analogous to that described for Intermediate 2 starting from Intermediate 1 and using dioxane instead of THF as solvant.

INTERMEDIATE 3

[(4S)-6-(3-Fluorophenyl)-1-methyl-8-(methyloxy)-4H-[1,2,4]triazolo[4,3-a][1,4]benzodiazepin-4-yl]acetic acid

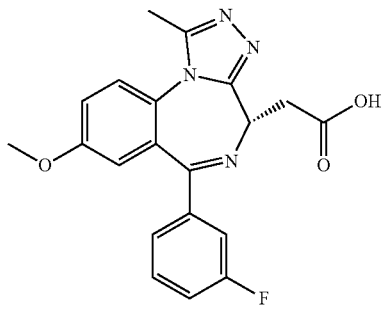 [SMILES: COc1ccc2c(c1)C(c1cccc(F)c1)=N[C@@H](CC(=O)O)c1nnc(C)n1-2]

LC/MS: m/z 381 [M+H]$^+$, Rt 2.08 min.

INTERMEDIATE 4

Methyl [(3S)-2-[(1Z)-2-acetylhydrazino]-5-(4-chlorophenyl)-7-(methvloxy)-3H-1,4-benzodiazepin-3-yl]acetate

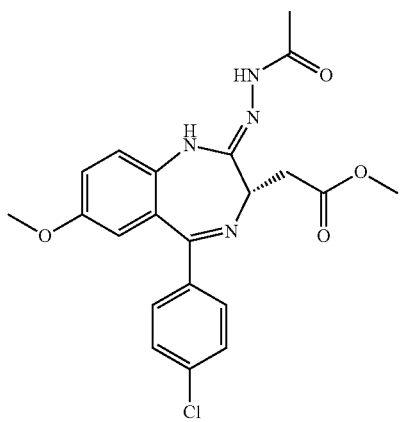

To a suspension of Intermediate 6 (30.2 g, 77.7 mmol) in THF (800 mL) at 0° C. was added hydrazine monohydrate (11.3 mL, 233 mmol) dropwise. The reaction mixture was stirred for 4 h between 0° C. and 15° C. before being cooled at 0° C. Et$_3$N (32.4 mL, 230 mmol) was then added slowly and AcCl (16.3 mL, 230 mmol) was added dropwise. The mixture was allowed to warm to RT and stir for 1 h then quenched with water and concentrated under reduced pressure. The resulting aqueous layer was then extracted with DCM and the organic layer was dried over Na$_2$SO$_4$, filtered and concentrated in vacuo to give the crude title compound (34 g, 100% yield) which was used without further purification. LC/MS: m/z 429 [M($^{35}$Cl)+H]$^+$, Rt 2.83 min.

The method described above could equally be applied to the racemic form of Intermediate 6 to give the product in racemic form.

Intermediate 5 was prepared by methods analogous to that described for Intermediate 4 starting from Intermediate 7.

INTERMEDIATE 5

Methyl [(3S)-2-[(1Z)-2-acetylhydrazino]-5-(3-fluorophenyl)-7-(methvloxy)-3H-1,4-benzodiazepin-3-yl]acetate

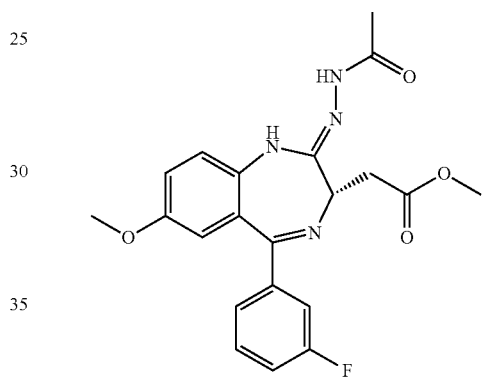

LC/MS: m/z 413 [M+H]$^+$, Rt 2.66 min.

INTERMEDIATE 6

Methyl [(3S)-5-(4-chlorophenyl)-7-(methyloxy)-2-thioxo-2,3-dihydro-1H-1,4-benzodiazepin-3-yl]acetate

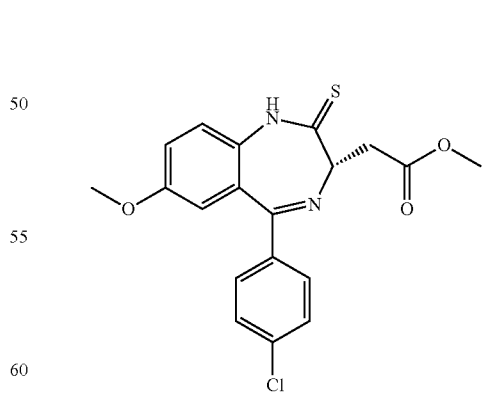

A suspension of P$_4$S$_{10}$ (85.8 g, 190 mmol) and Na$_2$CO$_3$ (20.5 g, 190 mmol) in 1,2-DCE (1.5 L) at RT was stirred for 1 h before Intermediate 9 (40 g, 107 mmol) was added. The resulting mixture was stirred at 65° C. for 4 h before being cooled and filtered. The solid was washed with DCM and the filtrate washed with sat. NaHCO₃. The organic layer was dried over Na₂SO₄, filtered and concentrated under reduced pressure. The title compound was precipitated from a DCM/i-Pr₂O mixture and filtered. The filtrate was then concentrated and purified by flash chromatography (DCM/MeOH: 98/2) to afford another batch of product. The title compound was obtained combining the two fractions (30.2 g, 73%) as a yellow powder. LC/MS: m/z 389 [M($^{35}$Cl)+H]$^+$, Rt 3.29 min.

Alternatively, Intermediate 9 could be reacted with Lawesson's reagent (0.6 equiv.) in refluxing toluene to give the title compound as a racemic mixture.

Intermediate 7 was prepared by methods analogous to that described for Intermediate 6 starting from Intermediate 10.

INTERMEDIATE 7

Methyl [(3S)-5-(3-fluorophenyl)-7-(methyloxy)-2-thioxo-2,3-dihydro-1H-1,4-benzodiazepin-3-yl]acetate

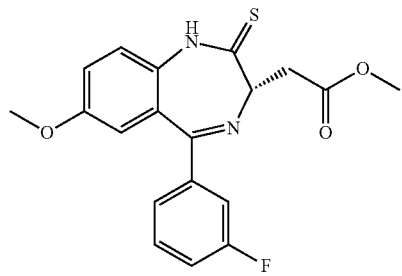

LC/MS: m/z 373 [M+H]$^+$, Rt 3.11 min.

INTERMEDIATE 8

2-[5-(4-Chlorophenol)-7-(methyloxy)-2-thioxo-2,3-dihydro-1H-1,4-benzodiazepin-3-yl]-N-cyclohexylacetamide

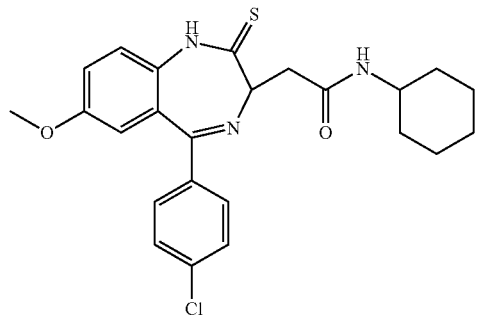 [SMILES: COc1ccc2c(c1)C(c1ccc(Cl)cc1)=NC(CC(=O)NC1CCCCC1)C(=S)N2]

To a solution of Intermediate 11 (500 mg, 1.3 mmol) in THF (50 mL) at RT was added DIEA (0.35 mL, 2.0 mmol) followed by HATU (760 mg, 2.0 mmol). The reaction mixture was stirred for 5 min before cyclohexylamine (0.23 mL, 2.0 mmol) was added. The mixture was stirred for 30 h and a further 0.5 equiv. of HATU, DIEA and cyclohexylamine were added with stirring. The organic layer was washed with 1N NaOH. The aqueous layer was extracted with DCM and the organics were dried over Na₂SO₄, filtered and concentrated in vacuo. The crude solid was then purified by flash chromatography on silica gel to give the title compound (420 mg, 62%) as a yellow foam. R$_f$=0.68 (DCM/MeOH: 90/10). LC/MS: m/z 456 [M($^{35}$Cl)+H]$^+$, Rt 3.11 min.

INTERMEDIATE 9

Methyl [(3S)-5-(4-chlorophenol)-7-(methyloxy)-2-oxo-2,3-dihydro-1H-1,4-benzodiazepin-3-yl]acetate

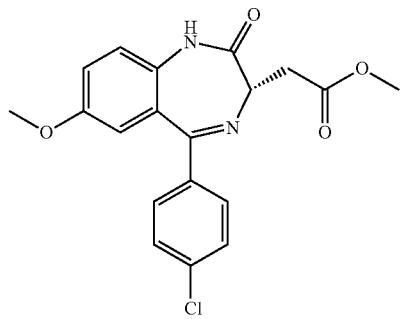

To a solution of the crude Intermediate 12 (assumed 0.2 mol) in DCM (500 mL) was added Et₃N (500 mL, 3.65 mol) and the resulting mixture was refluxed for 24 h before being concentrated. The resulting crude amine was dissolved in 1,2-DCE (1.5 L) and AcOH (104 mL, 1.8 mol) was added carefully. The reaction mixture was then stirred at 60° C. for 2h before being concentrated in vacuo and dissolved in DCM. The organic layer was washed with 1N HCl and the aqueous layer was extracted with DCM (×3). The combined organic layers were washed twice with water, and brine, dried over Na₂SO₄, filtered and concentrated under reduced pressure. The crude solid was recrystallised in MeCN leading to the title compound (51 g) as a pale yellow solid. The filtrate could be concentrated and recrystallised in MeCN to give another 10 g of Intermediate 9 (total: 61 g, 69% yield based on recovered Intermediate 12). R$_f$=0.34 (DCM/MeOH: 95/5). LC/MS m/z 373 [M($^{35}$Cl)+H]$^+$, Rt 2.76 min.

Intermediate 10 was prepared by methods analogous to that described for Intermediate 9 starting from Intermediate 13.

INTERMEDIATE 10

Methyl [(3S)-5-(3-fluorophenyl)-7-(methyloxy)-2-oxo-2,3-dihydro-1H-1,4-benzodiazepin-3-yl]acetate

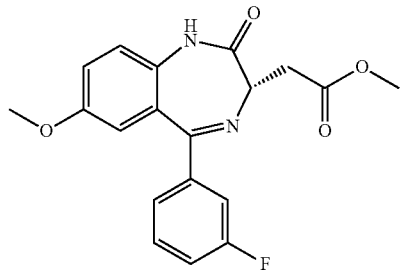

LC/MS: m/z 357 [M+H]$^+$, Rt 2.83 min.

INTERMEDIATE 11

[5-(4-Chlorophenol)-7-(methyloxy)-2-thioxo-2,3-dihydro-1H-1,4-benzodiazepin-3-yl]acetic acid

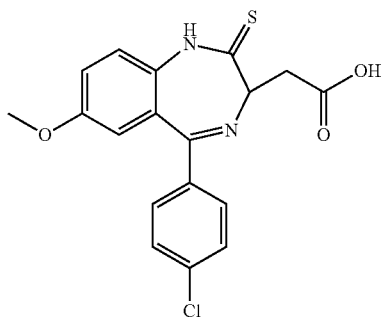 [SMILES: COc1ccc2c(c1)C(c1ccc(Cl)cc1)=NC(CC(=O)O)C(=S)N2]

To a solution of racemic Intermediate 6 (2.6 g, 6.7 mmol) in 1,4-dioxane (70 mL) at RT was added slowly 1N NaOH (13.5 mL) and the reaction mixture was stirred overnight before adding another 1N NaOH (13.5 mL). The mixture was then further stirred for 2h before 1,4-dioxane was removed in vacuo. The aqueous layer was acidified with 1N HCl to ca pH 6 and extracted with DCM. The organics were dried over $Na_2SO_4$, filtered and concentrated under reduced pressure to give the title compound (1.9 g, 76% yield) as a yellow solid. LC/MS: m/z 375 [M($^{35}$Cl)+H]$^+$, Rt=1.6 min.

INTERMEDIATE 12

Methyl $N^1$-[2-[(4-chlorophenyl)carbonyl]-4-(methyloxy)phenyl]-$N^2$-{[(9H-fluoren-9-ylmethyl)oxy]carbonyl}-L-α-asparaginate

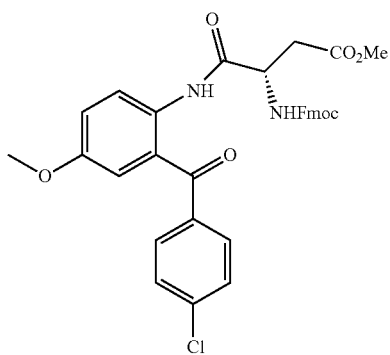

A mixture of Methyl N-{[(9H-fluoren-9-ylmethyl)oxy]carbonyl}-L-α-aspartyl chloride (prepared from *J. Org. Chem.* 1990, 55, 3068-3074 and *J. Chem. Soc. Perkin Trans.* 1 2001, 1673-1695) (221 g, 0.57 mol) and Intermediate 14 (133 g, 0.5 mol) in CHCl$_3$ (410 mL) was stirred at 60° C. for 1.5 h before being cooled and concentrated under reduced pressure and used without further purification. LC/MS: m/z 613 [M($^{35}$Cl)+H]$^+$, Rt=3.89 min.

Intermediate 13 was prepared by methods analogous to that described for Intermediate 12 starting from methyl N-{[(9H-fluoren-9-ylmethyl)oxy]carbonyl}-L-α-aspartyl chloride (prepared from *J. Org. Chem.* 1990, 55, 3068-3074 and *J. Chem. Soc. Perkin Trans.* 1 2001, 1673-1695) and (2-Amino-5-methoxy-phenyl)-(3-fluoro-phenyl)-methanone (*Synthesis* 1980, 677-688).

INTERMEDIATE 13

Methyl $N^1$-[2-[(3-fluorophenyl)carbonyl]-4-(methyloxy)phenyl]-$N^2$-{[(9H-fluoren-9-ylmethyl)oxy]carbonyl}-L-α-asparaqinate

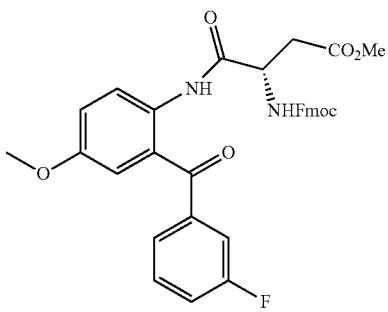

LC/MS: m/z 597 [M+H]$^+$, Rt 3.75 min.

INTERMEDIATE 14

[2-amino-5-(methyloxy)phenyl](4-chlorophenyl)methanone

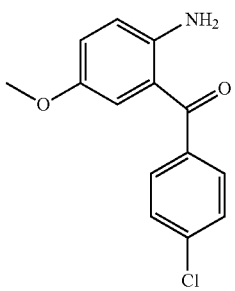 [SMILES: COc1ccc(N)c(C(=O)c2ccc(Cl)cc2)c1]

To a solution of Intermediate 15 (40.0 g, 0.21 mol) in a toluene (560 mL)/ether (200 mL) mixture at 0° C. was added dropwise a solution of 4-chlorophenylmagnesium bromide (170 mL, 1M in Et$_2$O, 0.17 mol). The reaction mixture was allowed to warm to RT and stirred for 1 h before being quenched with 1N HCl. The aqueous layer was extracted with EtOAc (3×) and the combined organics were washed with brine, dried over Na$_2$SO$_4$, filtered and concentrated under reduced pressure. The crude compound was then dissolved in EtOH (400 mL) and 6N HCl (160 mL) was added. The reaction mixture was refluxed for 2 h before being concentrated under reduced pressure. The resulting solid was filtered and washed twice with ether before being suspended in EtOAc and neutralised with 1N NaOH. The aqueous layer was extracted with EtOAc (3×) and the combined organics were washed with brine, dried over Na$_2$SO$_4$, filtered and concentrated under reduced pressure. The title compound was obtained as a yellow solid (39 g, 88% yield) which was used without further purification.

43

INTERMEDIATE 15

2-methyl-6-(methyloxy)-4H-3,1-benzoxazin-4-one

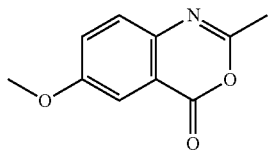

A solution of 5-methoxyanthranilic acid (7.8 g, 46.5 mmol) was refluxed in acetic anhydride (60 mL) for 2 h15 before being cooled and concentrated under reduced pressure. The crude residue was then concentrated twice in the presence of toluene before being filtered and washed with ether to yield to the title compound (6.8 g, 77% yield) as a beige solid; LC/MS: m/z 192 [M+H]$^+$, Rt 1.69 min.

INTERMEDIATE 16

1,1-Dimethylethyl [2-({[(4S)-6-(4-chlorophenyl)-1-methyl-8-(methyloxy)-4H-[1,2,4]triazolo[4,3-a][1,4]benzodiazepin-4-yl]acetyl}amino)ethyl]methylcarbamate

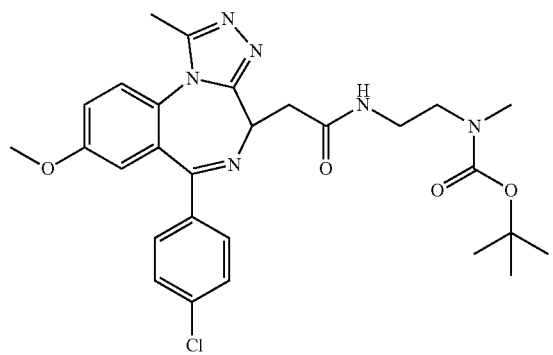 [SMILES: COc1ccc2c(c1)C(c1ccc(Cl)cc1)=NC(CC(=O)NCCN(C)C(=O)OC(C)(C)C)c1nnc(C)n1-2]

Intermediate 2 (104 mg, 0.262 mmol), 1,1-dimethylethyl (2-aminoethyl)methylcarbamate (0.049 mL, 0.275 mmol), HATU (120 mg, 0.314 mmol) and DIPEA (0.110 mL, 0.629 mmol) were dissolved in DMF (2.5 mL) and stirred at 50° C. under N$_2$ overnight. The reaction was allowed to cool next morning, then the DMF evaporated under vacuum and the crude oil partitioned between EtOAc and saturated aqueous sodium bicarbonate solution. The organic phase was washed with saturated aqueous brine, dried over anhydrous magnesium sulfate and evaporated under vacuum to give a colourless oil. Purification of the residue by flash chromatography on silica gel (DCM-methanol 0.5 to 10% gradient) gave the title compound as a yellow oil (189 mg, 0.342 mmol, 130% yield). LC/MS (M($^{35}$Cl)+H)$^+$ 553, (M($^{37}$Cl)+H)$^+$ 555; RT 1.07 min.

44

INTERMEDIATE 17

1,1-Dimethylethyl 4-({[(4S)-6-(4-chlorophenyl)-1-methyl-8-(methyloxy)-4H-[1,2,4]benzodiazepin-4-yl]acetyl}amino)-1-piperidinecarboxylate

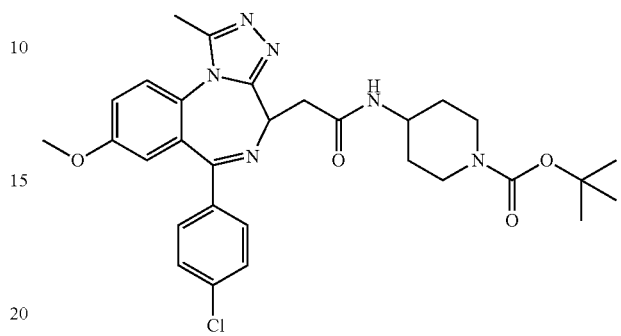

Intermediate 2 (100 mg, 0.252 mmol), 1,1-dimethylethyl 4-amino-1-piperidinecarboxylate (0.054 mL, 0.265 mmol), HATU (115 mg, 0.302 mmol) and DIPEA (0.106 mL, 0.605 mmol) were dissolved in (DMF) (2.5 mL) and stirred at 50° C. under N$_2$ overnight. The reaction was allowed to cool next morning, then the DMF evaporated under vacuum and the crude oil partitioned between EtOAc and saturated aqueous sodium bicarbonate solution. The organic phase was washed with saturated aqueous brine, dried over anhydrous magnesium sulfate and evaporated under vacuum to give a colourless oil. Purification of the residue by flash chromatography on silica gel (DCM-methanol 0.5 to 10% gradient) gave the title compound as a yellow oil (165 mg, 0.285 mmol, 113% yield). LC/MS (M($^{35}$Cl)+H)$^+$ 579, (M($^{37}$Cl)+H)$^+$ 581; RT 1.11 min.

Intermediates 18-21 were prepared from Intermediate 2 and the appropriate amine using the procedure described in Intermediate 17.

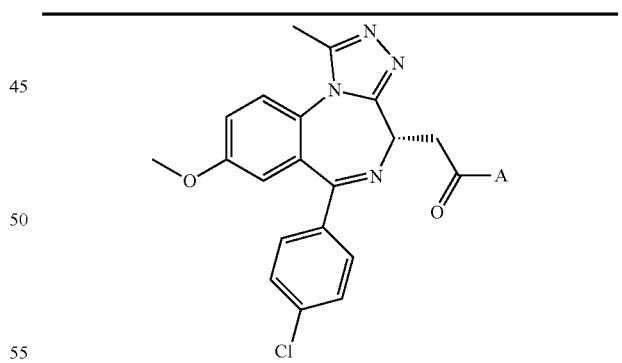

| Intermediate | A | Mass Spec (M($^{35}$Cl) + H)$^+$, (M($^{37}$Cl) + H)$^+$ | RT (mins) |
|---|---|---|---|
| 18 | | 593, 595 | 1.18 |

-continued

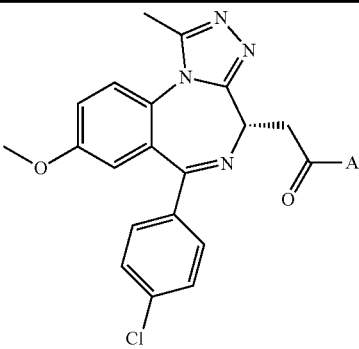

LC/MS was carried out using apparatus c).

| Intermediate | A | Mass Spec $(M(^{35}Cl) + H)^+$, $(M(^{37}Cl) + H)^+$ | RT (mins) |
|---|---|---|---|
| 19 | 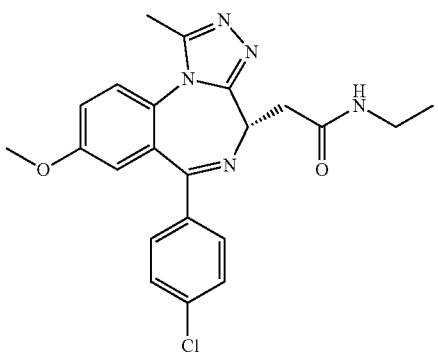 | 579, 581 | 1.09 |
| 20 | | 551, 553 | 1.07 |
| 21 | | 551, 553 | 1.04 |

INTERMEDIATE 22

[(4S)-6-(4-chlorophenyl)-8-hydroxy-1-methyl-4H-[1,2,4]triazolo[4,3-a][1,4]benzodiazepin-4-yl]acetic acid

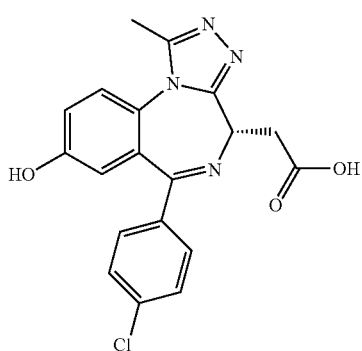 [SMILES: Cc1nnc2n1-c1ccc(O)cc1C(c1ccc(Cl)cc1)=N[C@H]2CC(=O)O]

A solution of Intermediate 2 (400 mg, 1 mmol) in DCM (8 mL) was cooled to −78° C. A solution of boron tribromide (1.26 g, 476 μl, 5 mmol) in dichloromethane (2 mL) was added slowly. The reaction mixture was a stirred at −78° C. for 30 minutes under nitrogen then allowed to warm to RT and stirred for 4 hours. The reaction mixture was poured onto ice/water (~100 mL) and the organic phase was separated. The aqueous phase was extracted with DCM (2×10 mL). The aqueous phase was evaporated to dryness. The residue was extracted with MeOH (3×10 mL) and the combined organic phase was evaporated and the residue re-evaporated from toluene (×2) to give the title compound as a yellow solid (383 mg, 1.0 mmol, 99% yield). LC/MS $(M(^{35}Cl)+H)^+$ 383, $(M(^{37}Cl)+H)^+$ 385; RT 0.73 min. (using LC/MS apparatus c)).

EXAMPLES

Example 1

2-[(4S)-6-(4-Chlorophenyl)-1-methyl-8-(methyloxy)-4H-[1,2,4]triazolo[4,3-a][1,4]benzodiazepin-4-yl]-N-ethylacetamide

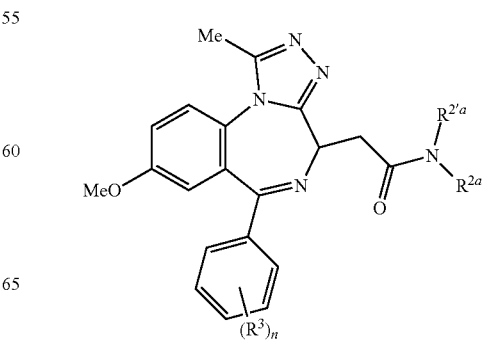

To a solution of Intermediate 2 (16.0 g, 40 mmol) in THF at RT was added DIEA (14 mL, 80 mmol) followed by HATU (30.4 g, 80 mmol). The reaction mixture was stirred for 3 h at this temperature and ethylamine (40 mL, 2M in THF, 80 mmol) was added. The mixture was stirred for 48 h before being concentrated under reduced pressure. The crude material was suspended in water and extracted with DCM. The organic layer was dried over $Na_2SO_4$, filtered and concentrated in vacuo. The crude solid was purified by chromatography on $SiO_2$ (DCM/MeOH 95/5) and the resulting solid recrystallised in MeCN. The solid was then dissolved in DCM and precipitated with i-$Pr_2O$ to give the title compound (8 g, 47% yield) as a white solid.

$R_f$=0.48 (DCM/MeOH: 90/10). Mp>140° C. (becomes gummy). $^1$H RMN (300 MHz, $CDCl_3$) δ7.53-7.47 (m, 2H), 7.39 (d, J=8.9 Hz, 1H), 7.37-7.31 (m, 2H), 7.20 (dd, J=2.9 and 8.9 Hz, 1H), 6.86 (d, J=2.9 Hz, 1H), 6.40 (m, 1H), 4.62 (m, 1H), 3.80 (s, 3H), 3.51 (dd, J=7.3 and 14.1 Hz, 1H), 3.46-3.21 (m, 3H), 2.62 (s, 3H), 1.19 (t, J=7.3 Hz, 3H). LC/MS: m/z 424 $[M(^{35}Cl)+H]^+$, Rt 2.33 min.

Examples 2 to 24 i.e. compounds of general formula (I) where $R^2$ is $NR^{2a}R^{2'a}$, (see Table 1) were prepared by methods analogous to that described for Example 1 from Intermediate 2 using the appropriate amine. Intermediate 3 was used in place of Intermediate 1 for Examples 23 and 24.

TABLE 1

| Ex | R³ | Config. | R²ᵃ | R²ᵃ | Physical data |
|---|---|---|---|---|---|
| 2 | 4-Cl | (R, S) | -CH₂-phenyl | H | LC/MS: m/z 500 [M($^{35}$Cl) + H]⁺, Rt 2.78 min. |
| 3 | 4-Cl | (R, S) | —(CH₂)5— | | LC/HRMS (M + H)⁺ calc for $C_{25}H_{26}^{35}ClN_5O_2$ 464.1853; found 464.1846. Rt 2.68 min. |
| 4 | 4-Cl | (R, S) | -CH₂-furan-2-yl | H | LC/HRMS (M + H)⁺ calc for $C_{25}H_{22}^{35}ClN_5O_3$ 476.1489; found 476.1471. Rt 2.56 min. |
| 5 | 4-Cl | (R, S) | -CH₂-CF₃ | H | LC/HRMS (M + H)⁺ calc for $C_{22}H_{18}^{35}ClF_3N_5O_2$ 478.1258; found 478.1256. Rt 2.60 min. |
| 6 | 4-Cl | (R, S) | -CH₂-tetrahydrofuran-2-yl | H | LC/HRMS (M + H)⁺ calc for $C_{25}H_{26}^{35}ClN_5O_3$ 480.1845; found 480.1830. Rt 2.37 min. |
| 7 | 4-Cl | (R, S) | —(CH₂)₂—O—(CH₂)₂— | | LC/MS: m/z 466 [M($^{35}$Cl) + H]⁺, Rt 2.66 min |
| 8 | 4-Cl | (R, S) | -CH₂-benzo[1,3]dioxol-5-yl | H | LC/HRMS (M + H)⁺ calc for $C_{28}H_{24}^{35}ClN_5O_4$ 530.1595; found 530.1578. Rt 2.67 min. Mp 255° C. |
| 9 | 4-Cl | (S) | 2-F-phenyl | H | LC/MS: m/z 490 [M($^{35}$Cl) + H]⁺, Rt 3.15 min. Mp 264° C. |
| 10 | 4-Cl | (S) | 3-F-phenyl | H | LC/MS: m/z 490 [M($^{35}$Cl) + H]⁺, Rt 3.25 min. Mp 248° C. |
| 11 | 4-Cl | (S) | 4-F-phenyl | H | LC/HRMS (M + H)⁺ calc for $C_{26}H_{21}^{35}ClFN_5O_2$ 490.1446; found 490.1399. Rt 2.81 min. Mp 246° C. |
| 12 | 4-Cl | (S) | pyridin-2-yl | H | LC/MS: m/z 473 [M($^{35}$Cl) + H]⁺, Rt 2.96 min. |
| 13 | 4-Cl | (S) | pyridin-3-yl | H | LC/MS: m/z 473 [M($^{35}$Cl) + H]⁺, Rt 2.75 min. Mp >160° C. |
| 14 | 4-Cl | (S) | pyridin-4-yl | H | LC/HRMS (M + H)⁺ calc for $C_{25}H_{21}^{35}ClN_6O_2$ 473.1493; found 473.1419. Rt 2.41 min. Mp 223° C. |
| 15 | 4-Cl | (S) | thiazol-2-yl | H | LC/HRMS (M + H)⁺ calc for $C_{23}H_{19}^{35}ClN_6O_2S$ 479.1057; found 479.1050. Rt 2.58 min. Mp 249° C. |

TABLE 1-continued

| Ex | R³ | Config. | R²ᵃ | R²ᵃ | Physical data |
|---|---|---|---|---|---|
| 16 | 4-Cl | (S) | (cyclopropylmethyl) | H | LC/HRMS (M + H)⁺ calc for $C_{24}H_{24}{}^{35}ClN_5O_2$ 450.1697; found 450.1613. Rt 2.50 min. Mp 128° C. |
| 17 | 4-Cl | (S) | (1-phenylethyl, dashed) | H | LC/MS: m/z 500 [M($^{35}$Cl) + H]⁺, Rt 2.73 min. |
| 18 | 4-Cl | (S) | (1-phenylethyl, wedge) | H | LC/MS: m/z 500 [M($^{35}$Cl) + H]⁺, Rt 4.23 min. |
| 19 | 4-Cl | (S) | (4-azidophenyl) | H | LC/MS: m/z 513 [M($^{35}$Cl) + H]⁺, Rt 3.33 min. |
| 20 | 4-Cl | (S) | (fluoren-9-on-2-yl) | H | LC/HRMS (M + H)⁺ calc for $C_{33}H_{24}{}^{35}ClN_5O_3$ 574.1646; found 574.1616. Rt 3.05 min. |
| 21 | 4-Cl | (S) | (3-benzoylphenyl) | H | LC/MS: m/z 576 [M($^{35}$Cl) + H]⁺, Rt 3.42 min |
| 22 | 4-Cl | (S) | (4-benzoylbenzyl) | H | LC/MS: m/z 590 [M($^{35}$Cl) + H]⁺, Rt 3.20 min. |
| 23 | 3-F | (S) | (ethyl) | H | LC/MS: m/z 408 [M($^{35}$Cl) + H]⁺, Rt 2.50 min. |
| 24 | 3-F | (S) | (4-fluorophenyl) | H | LC/MS: m/z 474 [M($^{35}$Cl) + H]⁺, Rt 3.01 min. |

Example 25

2-[(4S)-6-(4-Chlorophenyl)-1-methyl-8-(methyloxy)-4H-[1,2,4]triazolo[4,3-a][1,4]benzodiazepin-4-yl]-N-[4-(4-methoxybenzoyl)phenyl]acetamide

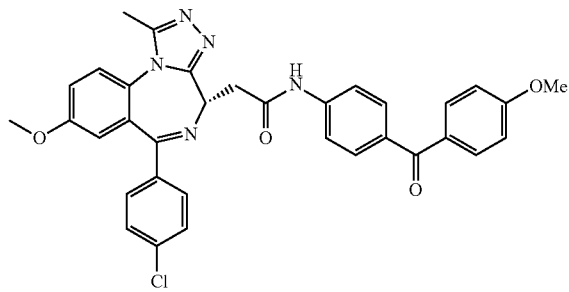 [SMILES: COc1ccc(C(=O)c2ccc(NC(=O)C[C@@H]3N=C(c4ccc(Cl)cc4)c4cc(OC)ccc4-n4c(C)nnc43)cc2)cc1]

To a solution of Intermediate 2 (1 g, 2.5 mmol) in THF at 0° C. was added dropwise oxalyl chloride (1.26 mL, 2.0 M in DCM, 2.5 mmol). DMF (1 mL) was then added dropwise and the reaction mixture was stirred for 1 h before a further 1 equiv of oxalylchloride was added. The reaction mixture was stirred another 1 h. One tenth of the latter solution was then added to a solution of (4-aminophenyl)[4-(methyloxy)phenyl]methanone (50 mg, 0.22 mmol) and $Et_3N$ in THF. The mixture was stirred overnight before being quenched with 1N NaOH. The aqueous layer was extracted with EtOAc and organics were washed with brine, dried over $Na_2SO_4$, filtered and concentrated in vacuo. The crude product was purified by flash chromatography on silica gel (DCM then DCM/MeOH: 95/5) and the solid was triturated in i-$Pr_2O$ to give the title compound (38 mg, 26% yield) as a ochre powder. LC/MS: m/z 606 [M($^{35}$Cl)+H]$^+$, Rt 3.41 min.

Examples 26 to 29 i.e. compounds of general formula (I) where $R^2$ is $NR^{2a}R^{2'a}$, (see Table 2) were prepared by methods analogous to that described for Example 25 using the appropriate amine.

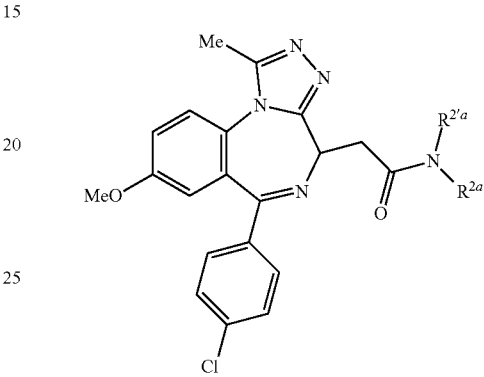

TABLE 2

| Ex | Config. | $R^{2a}$ | $R^{2'a}$ | Physical data |
|----|---------|----------|-----------|---------------|
| 26 | (R, S) | ...CH₂CH₂N(CH₃)₂ | H | LC/HRMS (M + H)$^+$ calc for $C_{24}H_{28}{}^{35}ClN_6O_2$ 467.1962; found 467.1964. Rt 2.60 min. |
| 27 | (S) | fluorenone | H | LC/MS: m/z 574 [M($^{35}$Cl) + H]$^+$, Rt 3.66 min |
| 28 | (S) | 4-(4-iodobenzoyl)phenyl | H | LC/MS: m/z 702 [M($^{35}$Cl) + H]$^+$, Rt = 3.78 min |
| 29 | (S) | 2-benzoyl-4-iodophenyl | H | LC/MS: m/z 702 [M($^{35}$Cl) + H]$^+$, Rt = 3.79 min |

Example 30

2-[6-(4-Chlorophenyl)-1-methyl-8-(methyloxy)-4H-[1,2,4]triazolo[4,3-a][1,4]benzodiazepin-4-yl]-N-cyclohexylacetamide

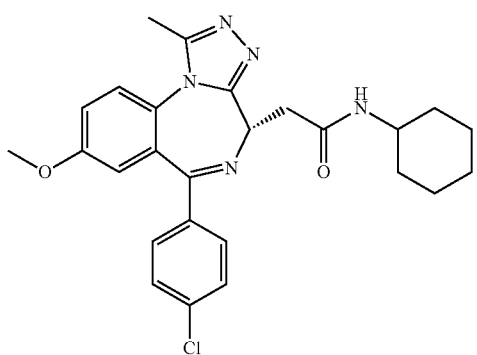 [SMILES: COc1ccc2c(c1)C(c1ccc(Cl)cc1)=N[C@@H](CC(=O)NC1CCCCC1)c1nnc(C)n1-2]

To a solution of Intermediate 8 (420 mg, 0.9 mmol) in MeOH (40 mL) at 0° C. was added hydrazine monohydrate (0.22 mL, 4.6 mmol). After 15 min at 0° C., the reaction mixture was allowed to warm RT for 1 h and a further 2.5 equiv. of hydrazine hydrate before being heated to 40° C. for 15 min. The mixture was then concentrated to half volume and water was added. The aqueous layer was extracted with DCM (×2) and the organics were dried over $Na_2SO_4$, filtered and concentrated in vacuo. The crude product was then dissolved in MeOH (30 mL) and trimethylorthoacetate (0.17 mL, 1.3 mmol) and PPTS (45 mg, 0.18 mmol) were added. The reaction mixture was refluxed for 45 min before being concentrated under reduced pressure. The crude mixture was dissolved in DCM and washed with water, dried over $Na_2SO_4$, filtered and concentrated in vacuo. The crude solid was then purified by flash chromatography on silica gel to give the title compound (70 mg, 16% yield over two steps) as a white solid. $R_f$=0.5 (DCM/MeOH: 90/10). Mp>260° C. LC/HRMS (M+H)$^+$ calculated for $C_{26}H_{28}^{35}ClN_5O_2$ 478.2010; found 478.1968. Rt 2.76 min.

Example 31

(4S)-6-(4-Chlorophenyl)-4-{2-[(4-fluorophenyl)amino]-2-oxoethyl}-1-methyl-4H-[1,2,4]triazolo[4,3-a][1,4]benzodiazepin-8-yl methanesulfonate

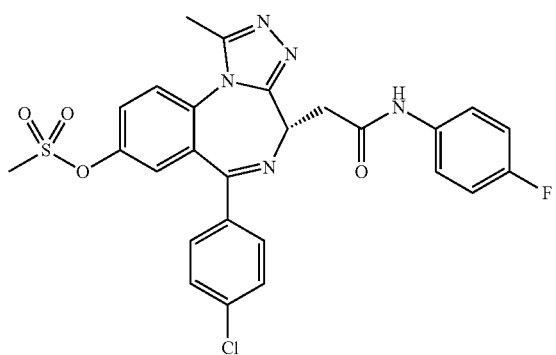 [SMILES: Cc1nnc2n1-c1ccc(OS(C)(=O)=O)cc1C(c1ccc(Cl)cc1)=N[C@H]2CC(=O)Nc1ccc(F)cc1]

To a solution of Example 32 (20 mg, 42 μmol) and $Et_3N$ (9 μL, 63 μmol) in THF (1 mL) at RT was added methanesulfonyl chloride (5 μL, 63 μmol). The reaction mixture was stirred for 5 h before another $Et_3N$ (63 μmol) and methanesulfonyl chloride (63 μmol) were added twice. After concentration, the crude mixture was dissolved in DCM and washed successively with 1N HCl, 1N NaOH and brine, dried over $Na_2SO_4$, filtered and concentrated in vacuo. The crude solid was triturated in a DCM/i-Pr$_2$O mixture to give the title compound (9 mg, 39% yield) as a white solid. LC/MS: m/z 554 [M($^{35}$Cl)+H]$^+$, Rt 3.04 min.

Example 32

2-[(4S)-6-(4-Chlorophenyl)-8-hydroxy-1-methyl-4H-[1,2,4]triazolo[4,3-a][1,4]benzodiazepin-4-yl]-N-(4-fluorophenyl)acetamide

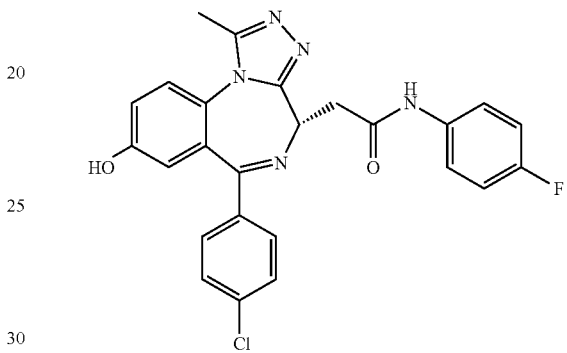

A mixture of a solution of Example 11 (50 mg, 0.1 mmol) in DCM (1 mL) and $BBr_3$ (0.51 mL, 1M in DCM, 0.51 mmol) at 0° C. was allowed to stir and warm to RT for 5 h before being quenched with water. The organic layer was then washed with a saturated hydrosulfite solution and brine before being dried over $Na_2SO_4$, filtered and concentrated in vacuo. The crude solid was triturated in a DCM/i-Pr$_2$O mixture to give the title compound (47 mg, 99% yield) as a pale yellow solid. Mp=222° C. (decomposition). LC/MS: m/z 476 [M($^{35}$Cl)+H]$^+$, Rt 2.82 min.

Example 33 was prepared by a method analogous to that described for Example 32 starting from Example 1.

Example 33

2-[(4S)-6-(4-Chlorophenyl)-8-hydroxy-1-methyl-4H-[1,2,4]triazolo[4,3-a][1,4]benzodiazepin-4-yl]-N-ethylacetamide

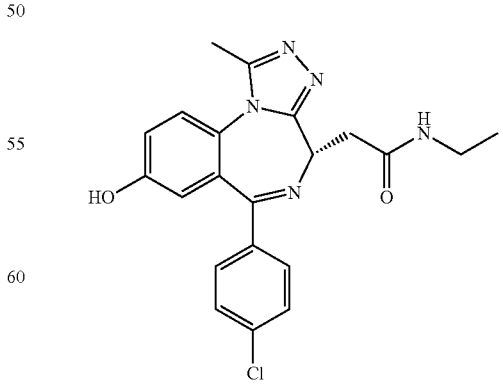

LC/HRMS (M+H)$^+$ calc for $C_{21}H_{20}^{35}ClN_5O_2$ 410.1384; found 410.1324. Rt 2.05 min.

Example 34

Methyl [(4S)-6-(4-chlorophenyl)-1-methyl-8-(methyloxy)-4H-[1,2,4]triazolo[4,3-a][1,4]benzodiazepin-4-yl]acetate

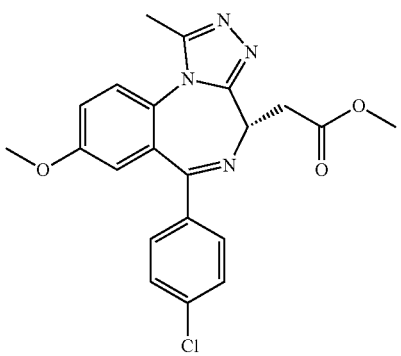

The crude Intermediate 4 (34 g, 79 mmol) was suspended in THF (200 mL) and AcOH (200 mL) was added at RT. The reaction mixture was stirred at this temperature overnight before being concentrated to dryness. The residue was suspended in saturated NaHCO$_3$ and extracted with DCM. The organic layer was dried over Na$_2$SO$_4$, filtered and concentrated in vacuo. The crude solid was purified by chromatography on SiO$_2$ (DCM/MeOH: 90/10) to give the title compound (28 g, 86% yield) as a yellow powder.

$^1$H NMR (300 MHz, CDCl$_3$) δ 7.54-7.47 (m, 2H), 7.40 (d, J=8.8 Hz, 1H), 7.37-7.31 (m, 2H), 7.22 (dd, J=2.8 and 8.8 Hz, 1H), 6.89 (d, J=2.8 Hz, 1H), 4.61 (dd, J=6.4 and 7.8 Hz, 1H), 3.82 (s, 3H), 3.78 (s, 3H), 3.66 (dd, J=7.8 and 16.9 Hz, 1H), 3.60 (dd, J=6.4 and 16.9 Hz, 1H), 2.62 (s, 3H). LC/MS m/z 411 [M($^{35}$Cl)+H]$^+$, Rt 2.88 min.

The method described above could equally be applied to the racemic form of Intermediate 4 to give the product in racemic form.

Example 35

Ethyl [(4S)-6-(4-chlorophenyl)-1-methyl-8-(methyloxy)-4H-[1,2,4]triazolo[4,3-a][1,4]benzodiazepin-4-yl]acetate

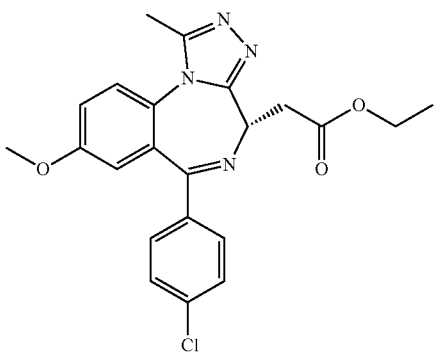 [SMILES: CCOC(=O)C[C@@H]1N=C(c2ccc(Cl)cc2)c2cc(OC)ccc2-n2c(C)nnc21]

To a solution of Intermediate 2 (200 mg, 0.5 mmol) in THF (10 mL) at 0° C. was added oxalylchloride (0.37 mL, 2M in DCM, 0.75 mmol). After stirring 3 hours, excess ethanol was added and the reaction was allowed to warm to room temperature and stir an additional 24 hours. The mixture was concentrated to dryness and the residue taken up in water and extracted with DCM to afford a crude mixture which was purified by Mass Directed Auto Prep to give the title compound as a white powder (30 mg, 15%).

$^1$H NMR (300 MHz, CDCl$_3$) δ 7.54-7.47 (m, 2H), 7.39 (d, J=9.1 Hz, 1H), 7.37-7.32 (m, 2H), 7.22 (dd, J=2.8 and 9.1 Hz, 1H), 6.89 (d, J=2.8 Hz, 1H), 4.61 (dd, J=6.2 and 7.9 Hz, 1H), 4.23 (q, J=7.2 Hz, 2H), 3.82 (s, 3H), 3.64 (dd, J=7.9 and 17.0 Hz, 1H), 3.58 (dd, J=6.3 and 17.0 Hz, 1H), 2.63 (s, 3H), 1.33 (t, J=7.2 Hz, 3H). LC/HRMS (M+H)$^+$ calc for C$_{22}$H$_{21}$$^{35}$ClN$_4$O$_3$ 425.1333; found 425.1328. Rt 2.80 min.

Example 36

1-Methylethyl [(4S)-6-(4-chlorophenyl)-1-methyl-8-(methyloxy)-4H-[1,2,4]triazolo[4,3-a][1,4]benzodiazepin-4-yl]acetate

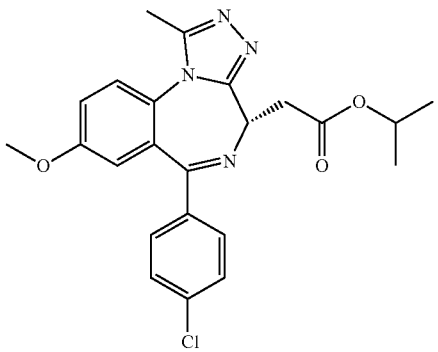 [SMILES: COc1ccc2c(c1)C(c1ccc(Cl)cc1)=N[C@@H](CC(=O)OC(C)C)c1nnc(C)n1-2]

To a solution of Intermediate 2 (200mg, 0.5 mmol) in isopropanol were added at room temperature DIC (80 μL, 0.55 mmol) and DMAP (67 mg, 0.55 mmol). After stirring 48 hours at RT, the crude mixture was concentrated under reduced pressure. Water was added and the compound was extracted with DCM and the organic layer dried over Na$_2$SO$_4$. Purification of the compound by Mass Directed Auto Prep afforded the title compound as white foam (40 mg, 19%).

$^1$H RMN (300 MHz, CDCl$_3$) δ7.49 (d, J=8.3 Hz, 2H), 7.39 (d, J=8.9 Hz, 1H), 7.34 (d, J=8.3 Hz, 2H), 7.21 (dd, J=2.6 and 8.9 Hz, 1H), 6.88 (d, J=2.6 Hz, 1H), 5.08 (m, 1H), 4.59 (m, 1H), 3.81 (s, 3H), 3.70-3.48 (m, 2H), 2.61 (s, 3H), 1.31 (d, J=6.4 Hz, 3H), 1.28 (d, J=6.4 Hz, 3H). LC/HRMS (M+H)$^+$ calc for C$_{23}$H$_{23}$$^{35}$ClN$_4$O$_3$ 439.1537; found 439.1527; Rt 2.89 min.

Example 37

Butyl [(4S)-6-(4-chlorophenyl)-1-methyl-8-(methyloxy)-4H-[1,2,4]triazolo[4,3-a][1,4]benzodiazepin-4-yl]acetate

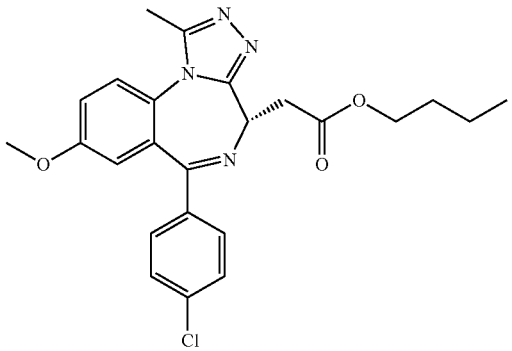 [SMILES: CCCCOC(=O)C[C@@H]1N=C(c2ccc(Cl)cc2)c2cc(OC)ccc2-n2c(C)nnc21]

To a solution of Intermediate 2 (200 mg, 0.5 mmol) in butanol were added at room temperature DIC (80 μL, 0.55 mmol) and DMAP (67 mg, 0.55 mmol). After stirring 48 hours at room temperature the crude mixture is concentrated under reduced pressure. Water was added and the compound was extracted with DCM and the organic layer dried over Na$_2$SO$_4$. Purification of the compound by Mass Directed Auto Prep afforded the title compound as white foam (70 mg, 31%).

$^1$H RMN (300 MHz, CDCl$_3$) δ7.51 (d, J=8.4 Hz, 2H), 7.39 (d, J=8.9 Hz, 1H), 7.34 (d, J=8.4 Hz, 2H), 7.22 (dd, J=2.6 and 8.8 Hz, 1H), 6.88 (d, J=2.6 Hz, 1H), 4.60 (dd, J=5.7 and 8.5 Hz, 1H), 4.18 (t, J=6.5 Hz, 2H), 3.82 (s, 3H), 3.66 (dd, J=8.5 and 16.8 Hz, 1H), 3.56 (dd, J=5.7 and 16.8 Hz, 1H), 2.62 (s, 3H), 1.66 (m, 2H), 1.42 (m, 2H), 0.95 (t, J=7.3 Hz, 3H). LC/HRMS (M+H)$^+$ calc for C$_{24}$H$_{25}$$^{35}$ClN$_4$O$_3$ 453.1693; found 453.1704; Rt 3.06 min.

Example 38

2-[(4S)-6-(4-Chlorophenyl)-1-methyl-8-(methyloxy)-4H-[1,2,4]triazolo[4,3-a][1,4]benzodiazepin-4-yl]-N-[2-(methylamino)ethyl]acetamide trifluoroacetic acid salt

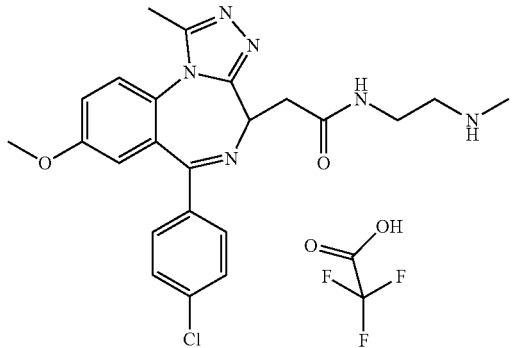

Intermediate 16 (189 mg, 0.342 mmol) and trifluoroacetic acid (0.022 mL, 0.285 mmol) were dissolved in DCM (3 mL) and stirred at 25° C. under N$_2$ for 2 h. The solvent was evaporated under vacuum and the residue obtained dissolved in DCM and re-evaporated under vacuum to give a yellow oil which was dried under high vacuum to afford the title compound as a yellow solid (153 mg, 0.270 mmol, 95% yield). LC/MS (M($^{35}$Cl)+H)$^+$ 453, (M($^{37}$Cl)+H)$^+$ 455; RT 0.74 min.

Example 39

2-[(4S)-6-(4-Chlorophenyl)-1-methyl-8-(methyloxy)-4H-[1,2,4]triazolo[4,3-a][1,4]benzodiazepin-4-yl]-N-4-piperidinylacetamide trifluoroacetic acid salt

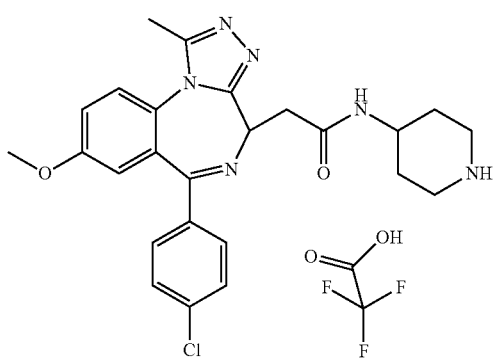 [SMILES: COc1ccc2c(c1)C(c1ccc(Cl)cc1)=NC(CC(=O)NC1CCNCC1)c1nnc(C)n1-2 ; O=C(O)C(F)(F)F]

Intermediate 17 (165 mg, 0.285 mmol) and trifluoroacetic acid (0.022 mL, 0.285 mmol) were dissolved in DCM (3 mL) and stirred at 25° C. under N$_2$ for 2 h. The solvent was evaporated under vacuum and the residue obtained dissolved in DCM and re-evaporated under vacuum to give a yellow oil which was dried under high vacuum to afford the title compound as a yellow solid (161 mg, 0.272 mmol, 95% yield). LC/MS (M($^{35}$Cl)+H)$^+$ 479, (M($^{37}$Cl)+H)$^+$ 481; RT 0.73 min.

Example 40

1-{[(4S)-6-(4-chlorophenyl)-1-methyl-8-(methyloxy)-4H-[1,2,4]triazolo[4,3-a][1,4]benzodiazepin-4-yl]acetyl}-N-methyl-4-piperidinamine formic acid salt

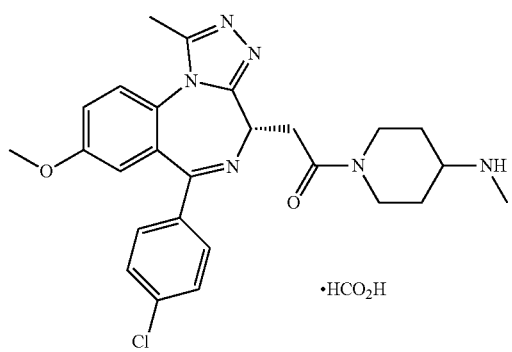

TFA (0.5 mL, 6.49 mmol) was added to a solution of Intermediate 18 (142 mg, 0.239 mmol) in DCM (2 mL) at 25° C. under N$_2$ and the mixture stirred for 2 hours. The solvent was evaporated under vacuum to give a yellow residue which was dissolved in MeOH (1 ml) and purified by Mass Directed AutoPrep to give the title compound as a cream solid (81 mg, 0.150 mmol, 62.8% yield) LC/MS (M($^{35}$Cl)+H)$^+$ 493, (M($^{37}$Cl)+H)$^+$ 495; RT 0.76 min (using LC/MS apparatus c)).

Examples 41 to 43

Examples 41 to 43 were prepared by a method analogous to that described for Example 40 starting from the appropriately protected Intermediate.

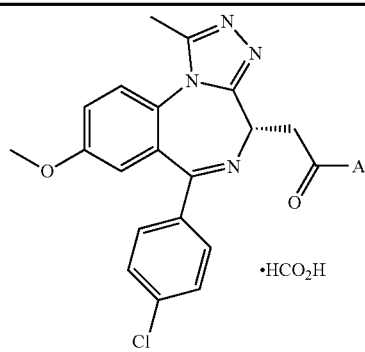

·HCO₂H

| Example | Name | From Intermediate | A | Mass Spectrum (M($^{35}$Cl) + H)$^+$, (M($^{37}$Cl) + H)$^+$ | RT (mins) |
|---|---|---|---|---|---|
| 41 | (S)-1-(4-aminopiperidin-1-yl)-2-(6-(4-chlorophenyl)-8-methoxy-1-methyl-4H-benzo[f][1,2,4]triazolo[4,3-a][1,4]diazepin-4-yl)ethanone | 19 | 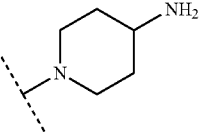 | 479, 481 | 0.75 |
| 42 | (S)-N-(azetidin-3-yl)-2-(6-(4-chlorophenyl)-8-methoxy-1-methyl-4H-benzo[f][1,2,4]triazolo[4,3-a][1,4]diazepin-4-yl)acetamide | 20 | 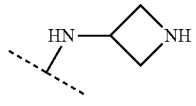 | 451, 453 | 0.73 |
| 43 | (S)-1-(3-aminoazetidin-1-yl)-2-(6-(4-chlorophenyl)-8-methoxy-1-methyl-4H-benzo[f][1,2,4]triazolo[4,3-a][1,4]diazepin-4-yl)ethanone | 21 | 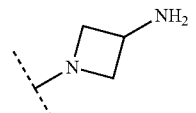 | 451, 453 | 0.73 |

LC/MS was carried out using apparatus c).

Example 44

(S)-2-(6-(4-chlorophenyl)-8-methoxy-1-methyl-4H-benzo[f][1,2,4]triazolo[4,3-a][1,4]diazepin-4-yl)-1-(4-hydroxypiperidin-1-yl)ethanone

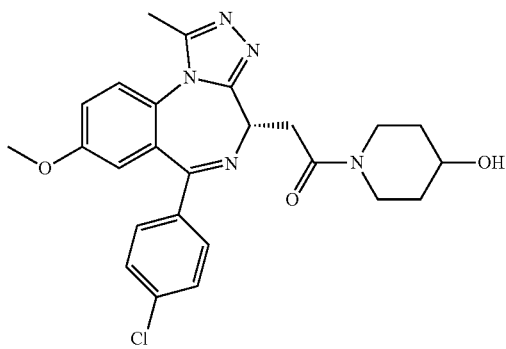 [SMILES: COc1ccc2c(c1)C(c1ccc(Cl)cc1)=N[C@@H](CC(=O)N1CCC(O)CC1)c1nnc(C)n1-2]

Example 44 was prepared by a method analogous to that described for Intermediate 17 starting from Intermediate 2 and the appropriate amine.

LC/HRMS (M($^{35}$Cl)+H)$^+$, (M($^{37}$Cl)+H)$^+$; found 480, 482. Rt 0.86 min (using LC/MS apparatus c)).

Example 45

2-[(4S)-6-(4-chlorophenyl)-1-methyl-8-(methyloxy)-4H-[1,2,4]triazolo[4,3-a][1,4]benzodiazepin-4-yl]-N-[2-(4-morpholinyl)ethyl]acetamide

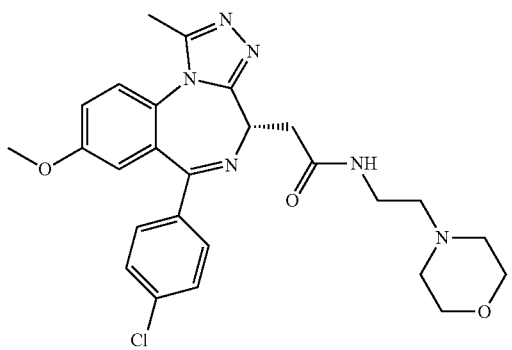 [SMILES: COc1ccc2c(c1)C(c1ccc(Cl)cc1)=N[C@@H](CC(=O)NCCN1CCOCC1)c1nnc(C)n1-2]

Intermediate 2 (104 mg, 0.262 mmol), [2-(4-morpholinyl)ethyl]amine (0.036 mL, 0.275 mmol), COMU (135 mg, 0.314 mmol) and DIPEA (0.055 mL, 0.314 mmol) were dissolved in DMF (3 mL) and stirred at 25° C. overnight. The solvent was evaporated to give an orange oil which was partitioned between DCM and saturated aqueous sodium bicarbonate solution. The mixture was separated on a hydrophobic frit and the chlorinated phase evaporated under vacuum to give an orange oil which was purified by flash chromatography on silica gel (DCM-MeOH 5-20% gradient) to give the title compound as a an orange solid (64 mg, 0.126 mmol, 48.0% yield). LC/MS (M($^{35}$Cl)+H)$^+$ 509, (M($^{37}$Cl)+H)$^+$ 511; RT 0.77 min (using LC/MS apparatus c)).

Example 46

2-[(4S)-6-(4-chlorophenyl)-1-methyl-8-(methyloxy)-4H-[1,2,4]triazolo[4,3-a][1,4]benzodiazepin-4-yl]-N-[2-(1H-imidazol-4-yl)ethyl]acetamide

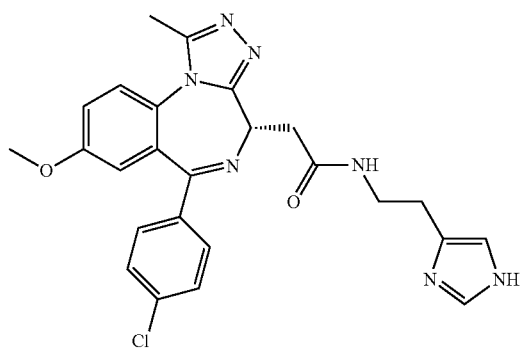 [SMILES: COc1ccc2c(c1)C(c1ccc(Cl)cc1)=N[C@@H](CC(=O)NCCc1c[nH]cn1)c1nnc(C)n1-2]

Intermediate 2 (104 mg, 0.262 mmol), histamine (30.6 mg, 0.275 mmol), COMU (135 mg, 0.314 mmol) and DIPEA (0.055 mL, 0.314 mmol) were dissolved in DMF (3 mL) and stirred at 25° C. overnight. More histamine (30.6 mg, 0.275 mmol) and COMU (135 mg, 0.314 mmol) and DIPEA (0.055 mL, 0.314 mmol) were added and the reaction stirred for a further 6 hours then allowed to sit at RT over 56 hours. The solvent was evaporated to give an orange oil which was partitioned between DCM and saturated aqueous sodium bicarbonate solution. The mixture was separated on a hydrophobic frit and the chlorinated phase evaporated under vacuum to give a yellow oil which was purified by flash chromatography on silica gel (DCM-MeOH 5-20% gradient) to give the title compound as a white solid (66 mg, 0.135 mmol, 51.4% yield). LC/MS (M($^{35}$Cl)+H)$^+$ 490; RT 0.74 min (using LC/MS apparatus c)).

Example 47

(S)-tert-butyl-2-(6-(4-chlorophenyl)-8-methoxy-1-methyl-4H-benzo[f][1,2,4]triazolo[4,3-a][1,4]diazepin-4-yl)acetate

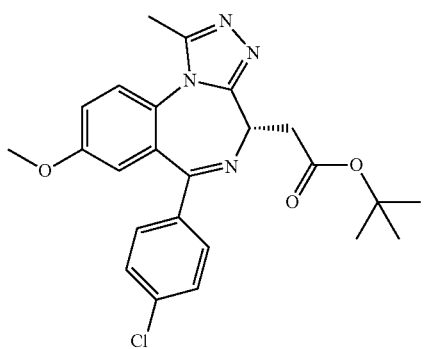 [SMILES: COc1ccc2c(c1)C(c1ccc(Cl)cc1)=N[C@@H](CC(=O)OC(C)(C)C)c1nnc(C)n1-2]

Oxalyl chloride (0.114 mL, 1.298 mmol) was added to a cold (0° C.) solution of Intermediate 2 (103 mg, 0.260 mmol) in DCM (2 mL) under $N_2$. DMF (0.020 mL, 0.260 mmol) was then added and the reaction allowed to warm to RT over 1 h. The crude acid chloride mixture was poured into a solution of tert-butanol (0.124 mL, 1.298 mmol) in DCM (2 mL) and Hunig's base (0.045 mL, 0.260 mmol) was added and stirred for 10 mins. Then more tert-butanol (1 mL) was added and the solution stirred for 1 h. The reaction mixture was evaporated and re-dissolved in tert-butanol (1 mL) twice more, then the solvent was evaporated a final time to give a yellow solid. Purification of the solid by flash chromatography on silica gel (cyclohexane-ethyl acetate 10 to 50% gradient) gave the title compound as a colourless oil (25 mg, 0.055 mmol, 21.27% yield). $^1$H NMR (400 MHz, CDCl$_3$) δ 7.50 (d, J=9 Hz, 2 H), 7.39 (d, J=9 Hz, 1 H), 7.20 (dd, J=9, 3 Hz, 1 H) 7.33 (s, 2 H), 6.89 (d, J=3 Hz, 1 H), 4.56 (dd, J=8, 6 Hz, 1 H), 3.81 (s, 3 H), 3.24-3.71 (m, 2 H), 2.62 (s, 3 H), 1.50 (s, 9 H). LC/MS (M($^{35}$Cl)+H)$^+$ 453, (M($^{37}$Cl)+H)$^+$ 455; RT 1.19 min (using LC/MS apparatus c)).

Example 48

(S)-piperidin-4-yl-2-(6-(4-chlorophenyl)-8-methoxy-1-methyl-4H-benzo[f][1,2,4]triazolo[4,3-a][1,4]diazepin-4-yl)acetate

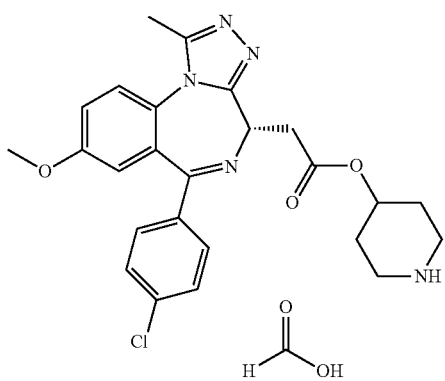 [SMILES: COc1ccc2c(c1)C(c1ccc(Cl)cc1)=N[C@@H](CC(=O)OC1CCNCC1)c1nnc(C)n1-2 ; O=CO]

Intermediate 2 (103 mg, 0.260 mmol), 1,1-dimethylethyl 4-hydroxy-1-piperidinecarboxylate (0.101 mL, 0.389 mmol), EDC (74.6 mg, 0.389 mmol) and DMAP (6.34 mg, 0.052 mmol) were dissolved in DCM (2 mL) at RT under $N_2$ and the reaction mixture allowed to stir overnight. The reaction mixture was quenched with saturated aqueous sodium bicarbonate solution and the mixture was filtered through a hydrophobic frit, and the chlorinated phase evaporated under vacuum to give a yellow residue. Purification of the solid by flash chromatography on silica gel (DCM-MeOH 5-20% gradient) gave the title compound as a colourless oil which was used immediately in the next reaction.

The colourless oil (157 mg, 0.271 mmol) and trifluoroacetic acid (0.5 mL, 6.49 mmol) were dissolved in DCM (2 mL) at 0° C. under $N_2$ and the mixture allowed to warm to RT over 1 h. The solvent was evaporated under vacuum and the residue obtained dissolved in DCM and re-evaporated under vacuum to give a yellow oil which was dried under high vacuum to afford the title compound as a yellow solid (50 mg, 0.095 mmol, 35% yield). $^1$H NMR (400 MHz, MeOH-d$_4$) δ 8.49 (s, 1 H), 7.66 (d, J=9 Hz, 1 H), 7.47 (d, J=9 Hz, 2 H), 7.23-7.41 (m, 3 H), 6.85 (s, 1 H), 5.04 (br. s., 1 H), 4.57 (t, J=7 Hz, 1 H), 3.77 (s, 3 H), 3.51 (d, J=7 Hz, 2 H), 3.28 (br. s., 2 H), 3.17 (br. s., 2 H), 2.59 (s, 3 H), 2.07 (br. s., 2 H), 1.93 (br. s., 2 H). LC/MS (M($^{35}$Cl)+H)$^+$ 480; RT 0.78 min (using LC/MS apparatus c)).

Example 49

2-[(4S)-6-(4-chlorophenyl)-8-hydroxy-1-methyl-4H-[1,2,4]triazolo[4,3-a][1,4]benzodiazepin-4-yl]-N-ethylacetamide

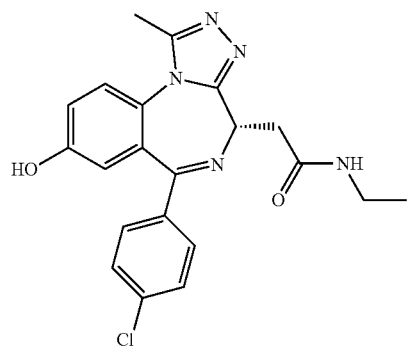 [SMILES: CCNC(=O)C[C@@H]1N=C(c2ccc(Cl)cc2)c2cc(O)ccc2-n2c(C)nnc21]

Intermediate 22 (383 mg, 1.00 mmol), ethylamine hydrochloride (163 mg, 2.0 mmol), HATU (457 mg, 1.20 mmol) and DIPEA (0.349 mL, 2.0 mmol) were dissolved in DMF (2 mL) and stirred at RT overnight. More ethylamine hydrochloride (163 mg, 2.0 mmol) and DIPEA (0.349 mL, 2.0 mmol) were added and the reaction stirred for a further 2 h. The reaction mixture was diluted with EtOAc (20 mL) and washed with saturated aqueous sodium bicarbonate solution (10 mL), water and brine. The organic phase was dried and evaporated under vacuum. Purification of the residue by flash chromatography on silica gel (DCM-methanol 10 to 20% gradient) gave the title compound as an off-white solid (200 mg, 0.488 mmol, 49% yield). LC/MS (M($^{35}$Cl)+H)$^+$ 410, (M($^{37}$Cl)+H)$^+$ 412; RT 0.76 min (using LC/MS apparatus c)).

Example 50

2-[(4S)-6-(4-chlorophenyl)-1-methyl-8-(methyloxy)-4H-[1,2,4]triazolo[4,3-a][1,4]benzodiazepin-4-yl]-N-[2-(dimethylamino)ethyl]acetamide formic acid salt

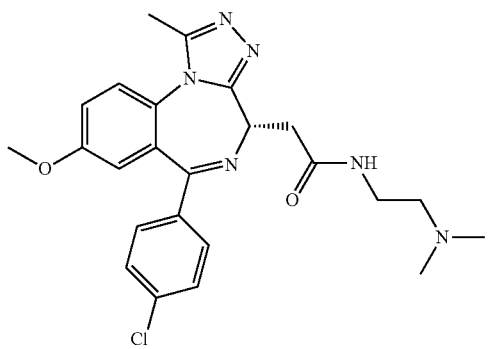

Intermediate 2 (105 mg, 0.265 mmol), N,N-dimethyl-1,2-ethanediamine (0.071 mL, 0.278 mmol), COMU (136 mg, 0.318 mmol) and DIPEA (0.116 mL, 0.661 mmol) were dissolved in DMF (3 mL) and stirred at 25° C. On addition of amine turned orange and allowed to stir at RT overnight. The solvent was evaporated to give a yellow oil which was partitioned between DCM and saturated aqueous sodium bicarbonate solution. The mixture was separated on a hydrophobic frit and the chlorinated phase evaporated under vacuum to give a yellow oil which was dissolved in MeOH (1 ml) and purified by Mass Directed AutoPrep to give the title compound as a white solid (48 mg, 0.094 mmol, 35.4% yield). $^1$H NMR (400 MHz, Methanol-$d_4$) δ 8.40 (br. s., 1 H), 7.70 (d, J=9 Hz, 1 H), 7.52 (d, J=9 Hz, 2 H), 7.26-7.45 (m, 3 H), 6.87 (s, 1 H), 4.62 (t, J=7 Hz, 1 H), 3.65 (s, 3 H), 3.65-3.92 (m, 3 H), 3.32-3.55 (m, 3 H), 3.24 (br. s., 1 H), 2.90 (s, 6 H), 2.62 (s, 3 H). LC/MS (M($^{35}$Cl)+H$^+$ 467, (M($^{37}$Cl)+H)$^+$ 469; RT 0.76 min (using LC/MS apparatus c)).

Example 51

2-[(4S)-6-(4-chlorophenyl)-1-methyl-8-(methyloxy)-4H-[1,2,4]triazolo[4,3-a][1,4]benzodiazepin-4-yl]-N-[3-(dimethylamino)propyl]acetamide formic acid salt

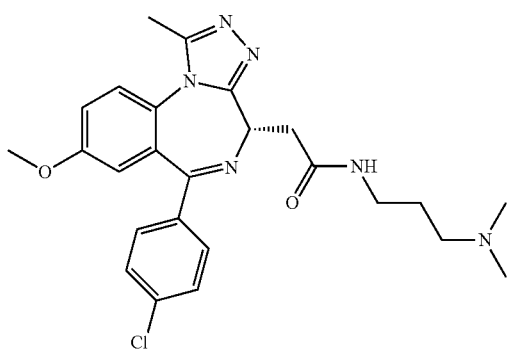

Intermediate 2 (100 mg, 0.252 mmol), N,N-dimethyl-1,3-propanediamine (0.033 mL, 0.265 mmol), HATU (115 mg, 0.302 mmol) and DIPEA (0.106 mL, 0.605 mmol) were dissolved in DMF (3 mL) and stirred at 25° C. overnight. The solvent was evaporated to give a yellow oil which was partitioned between DCM and saturated aqueous sodium bicarbonate solution. The mixture was separated on a hydrophobic frit and the chlorinated phase evaporated under vacuum to give a yellow oil which was dissolved in MeOH (1 ml) and purified by Mass Directed AutoPrep to give the title compound as a white solid (95 mg, 0.180 mmol, 71.5% yield). $^1$H NMR (400 MHz, Methanol-$d_4$) δ 8.41 (br. s., 1 H), 7.74 (d, J=9 Hz, 1 H), 7.56 (d, J=9 Hz, 2 H), 7.37-7.46 (m, 3 H), 6.91 (d, J=3 Hz, 1 H), 4.66 (t, J=7 Hz, 1 H), 3.83 (s, 3 H), 3.35-3.57 (m, 3 H), 3.28-3.18 (m, 4 H), 2.87 (s, 6 H), 2.66 (s, 3 H), 1.89-2.09 (m, 2 H). LC/MS (M($^{35}$Cl)+H$^+$ 481, (M($^{37}$Cl)+H$^+$ 483; RT 0.79 min (using LC/MS apparatus c)).

Example 52

2-[(4S)-6-(4-chlorophenyl)-1-methyl-8-(methyloxy)-4H-[1,2,4]triazolo[4,3-a][1,4]benzodiazepin-4-yl]-N-[3-(4-morpholinyl)propyl]acetamide

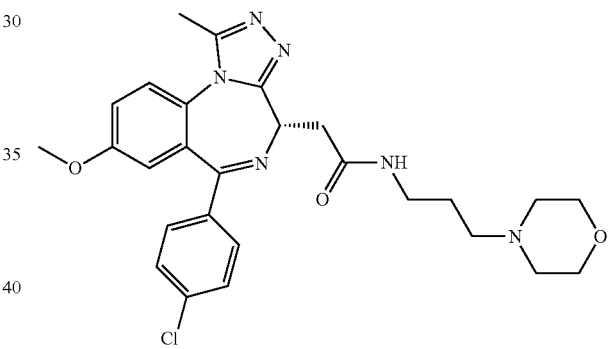

Intermediate 2 (150 mg, 0.378 mmol), [3-(4-morpholinyl)propyl]amine (57.2 mg, 0.397 mmol), HATU (172 mg, 0.454 mmol) and DIPEA (0.158 mL, 0.907 mmol) were dissolved in DMF (3 mL) and stirred at 25° C. overnight. The solvent was evaporated to give a yellow oil which was partitioned between DCM and saturated aqueous sodium bicarbonate solution. The mixture was separated on a hydrophobic frit and the chlorinated phase evaporated under vacuum to give a yellow oil. Purification by flash chromatography on silica gel (DCM-methanol 5 to 20% gradient) gave the title compound as a pale cream solid (77 mg, 0.147 mmol, 38.9% yield). $^1$H NMR (400 MHz, CDCl$_3$) δ 7.54 (t, J=5 Hz, 1 H), 7.42 (d, J=9 Hz, 2 H), 7.19-7.37 (m, 3 H), 7.13 (dd, J=9, 3 Hz, 1 H), 6.78 (d, J=3 Hz, 1 H), 4.58 (t, J=7 Hz, 1 H), 3.73 (s, 3 H), 3.66 (t, J=5 Hz, 3 H), 3.36-3.48 (m, 2 H), 3.22-3.36 (m, 3 H), 2.46-2.76 (m, 4 H), 2.17-2.46 (m, 5 H), 1.56-1.85 (m, 2 H). LC/MS (M($^{35}$Cl)+H$^+$ 523, (M($^{37}$Cl)+H)$^+$ 525; RT 0.74 min (using LC/MS apparatus c)).

Example 53

2[(4S)-6-(4-chlorophenyl)-1-methyl-8-(methyloxy)-4H-[1,2,4]triazolo[4,3-a][1,4]benzodiazepin-4-yl]-N-[2-(1,1-dioxido-4-thiomorpholinyl)ethyl]acetamide

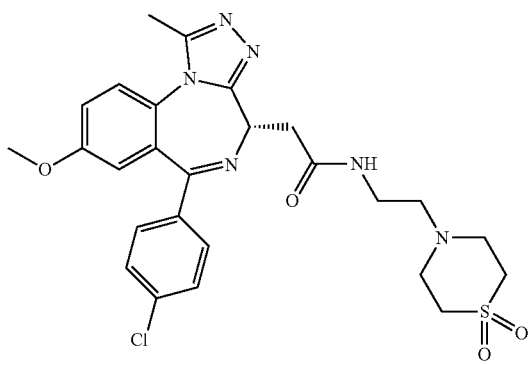 [SMILES: COc1ccc2c(c1)C(c1ccc(Cl)cc1)=N[C@@H](CC(=O)NCCN1CCS(=O)(=O)CC1)c1nnc(C)n1-2]

Intermediate 2 (150 mg, 0.378 mmol), [2-(1,1-dioxido-4-thiomorpholinyl)ethyl]amine (70.7 mg, 0.397 mmol), HATU (172 mg, 0.454 mmol) and DIPEA (0.158 mL, 0.907 mmol) were dissolved in DMF (3 mL) and stirred at 25° C. overnight. The solvent was evaporated to give a yellow oil which was partitioned between DCM and saturated aqueous sodium bicarbonate solution. The mixture was separated on a hydrophobic frit and the chlorinated phase evaporated under vacuum to give an orange oil. Purification by flash chromatography on silica gel (DCM-methanol 5 to 20% gradient) gave the title compound as a pale cream solid (84 mg, 0.151 mmol, 39.9% yield). $^1$H NMR (400 MHz, CDCl$_3$) δ 7.41-7.70 (m, 4 H), 7.30-7.41 (m, 2 H), 7.25 (dd, J=9, 3 Hz, 1 H), 6.87 (d, J=3 Hz, 1 H), 4.64 (dd, J=8, 6 Hz, 1 H), 3.82 (s, 3 H), 3.65-3.78 (m, 1 H), 3.56 (dd, J=15, 8 Hz, 1 H), 3.26-3.50 (m, 2 H), 3.19 (q, J=7 Hz, 1 H), 2.86-3.11 (m, 5 H), 2.63 (s, 3 H), 1.23-1.53 (m, 4 H). LC/MS (M($^{35}$Cl)+H)$^+$ 557, (M($^{37}$Cl)+H)$^+$ 559; RT 0.84 min (using LC/MS apparatus c)).

Examples 54 to 57

Examples 54 to 57 were prepared from Intermediate 2 and the appropriate amine using the procedure described in Example 1.

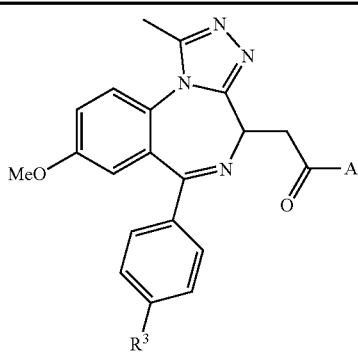

| Example | R$^3$ | Config. | A | Physical Data |
|---|---|---|---|---|
| 54 | Cl | (S) | 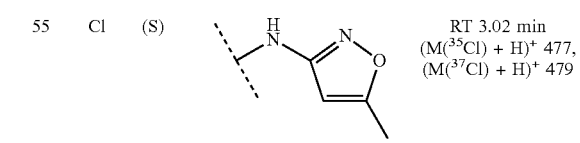 | RT 2.85 min (M($^{35}$Cl) + H)$^+$ 474, (M($^{37}$Cl) + H)$^+$ 476 |
| 55 | Cl | (S) | 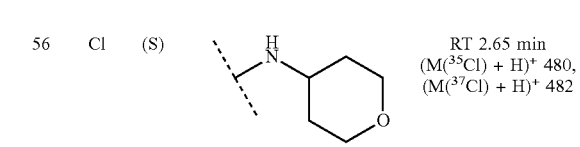 | RT 3.02 min (M($^{35}$Cl) + H)$^+$ 477, (M($^{37}$Cl) + H)$^+$ 479 |
| 56 | Cl | (S) | 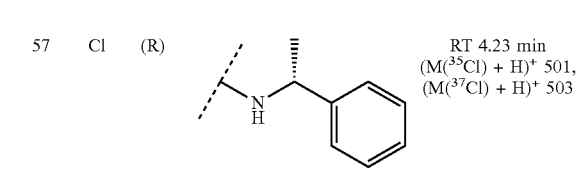 | RT 2.65 min (M($^{35}$Cl) + H)$^+$ 480, (M($^{37}$Cl) + H)$^+$ 482 |
| 57 | Cl | (R) | 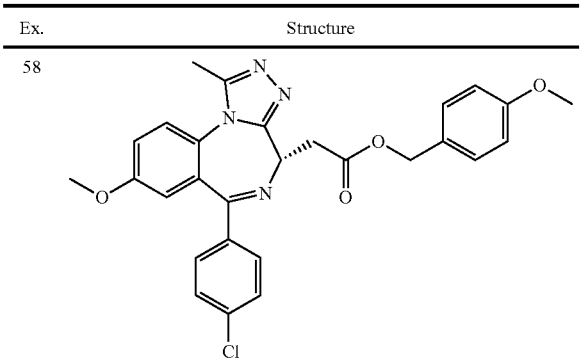 | RT 4.23 min (M($^{35}$Cl) + H)$^+$ 501, (M($^{37}$Cl) + H)$^+$ 503 |

LC/MS was carried out using apparatus c).

Further Example compounds of the invention include:

| Ex. | Structure |
|---|---|
| 58 | 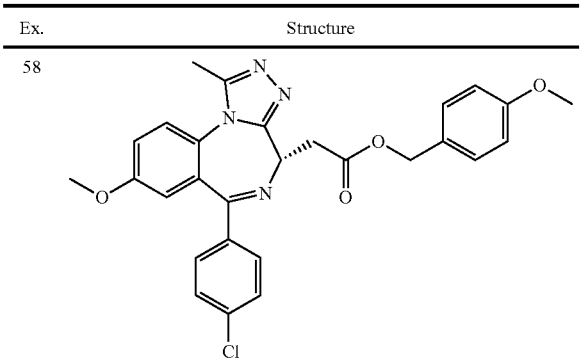 |

-continued
| Ex. | Structure |
|---|---|
| 59 | 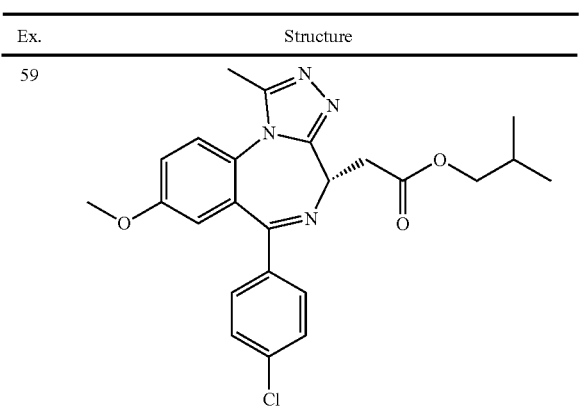 |
| 60 | 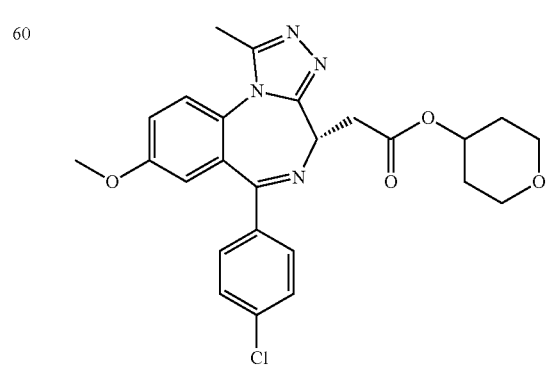 |
| 61 | 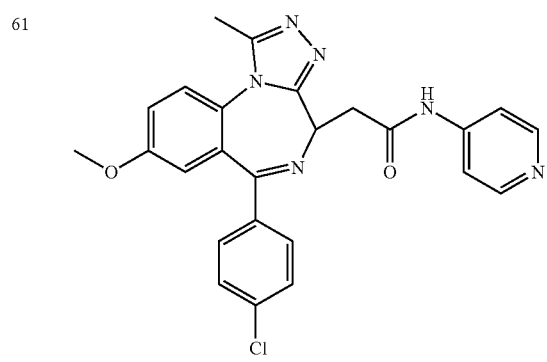 |
| 62 | 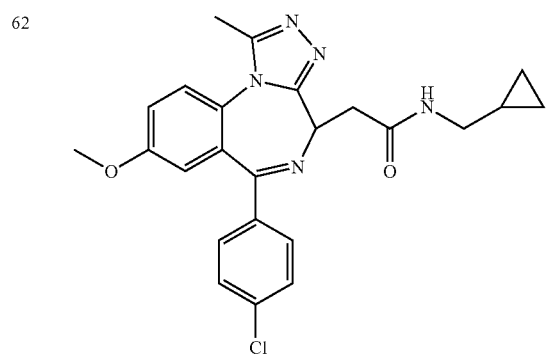 |加
-continued
| Ex. | Structure |
|---|---|
| 63 | 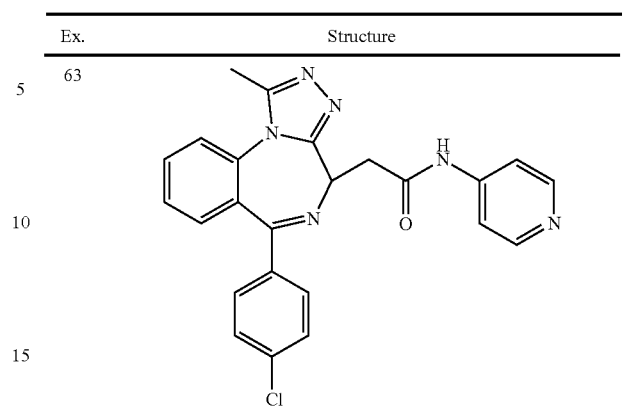 |
| 64 | 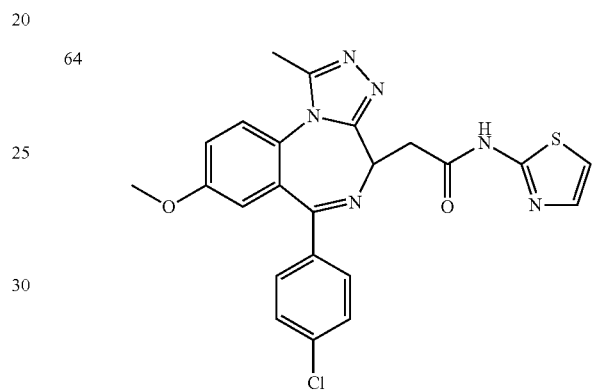 |
| 65 | 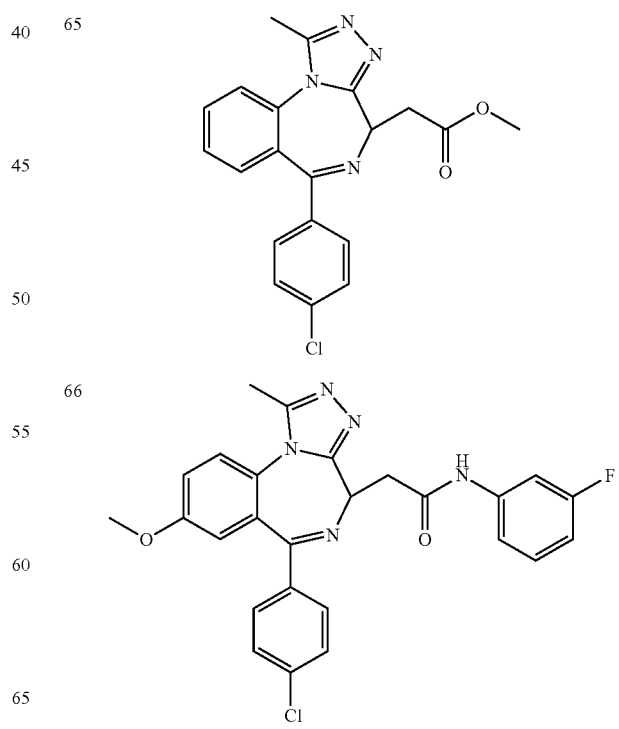 |

| Ex. | Structure |
|---|---|
| 67 | 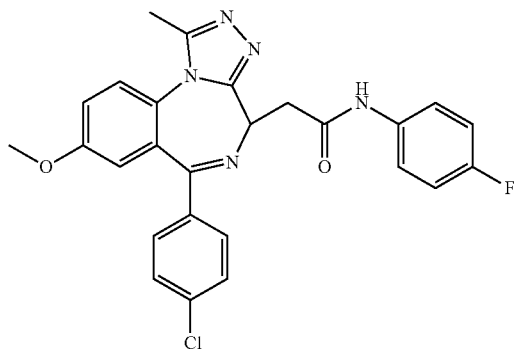 [SMILES: COc1ccc2c(c1)C(c1ccc(Cl)cc1)=NC(CC(=O)Nc1ccc(F)cc1)c1nnc(C)n1-2] |
| 68 | 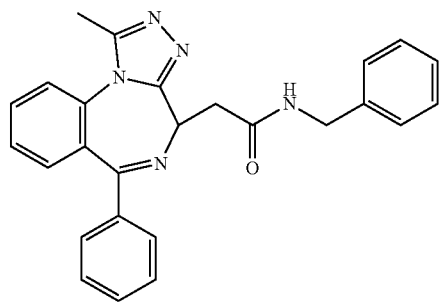 [SMILES: Cc1nnc2n1-c1ccccc1C(c1ccccc1)=NC2CC(=O)NCc1ccccc1] |
| 69 | 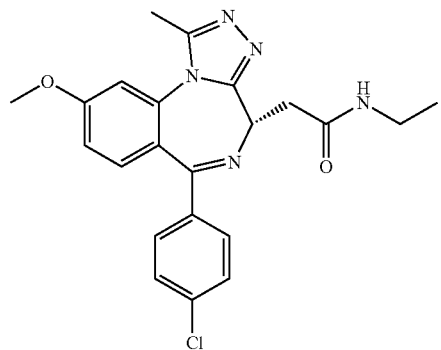 [SMILES: CCNC(=O)C[C@@H]1N=C(c2ccc(Cl)cc2)c2ccc(OC)cc2-n2c(C)nnc21] |
| 70 | 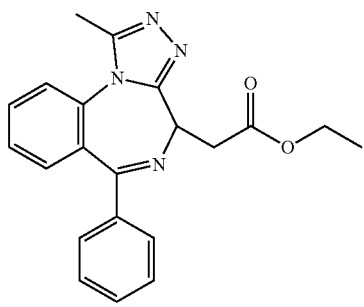 [SMILES: CCOC(=O)CC1N=C(c2ccccc2)c2ccccc2-n2c(C)nnc21] |
| Ex. | Structure |
|---|---|
| 71 | 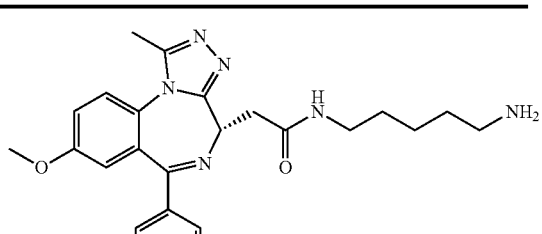  |
| 72 | 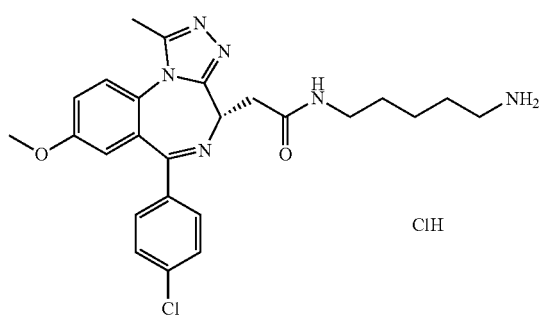 [SMILES: COc1ccc2c(c1)C(c1ccc(Cl)cc1)=N[C@@H](CC(=O)NCCCCCN)c1nnc(C)n1-2 ; Cl]  |
| 73 | 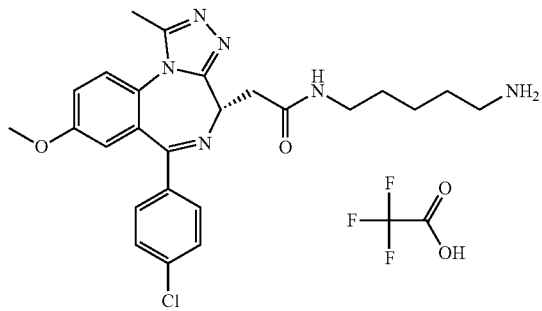 [SMILES: COc1ccc2c(c1)C(c1ccc(Cl)cc1)=N[C@@H](CC(=O)NCCCCCN)c1nnc(C)n1-2 ; O=C(O)C(F)(F)F] 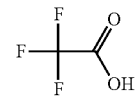 |
| 74 | 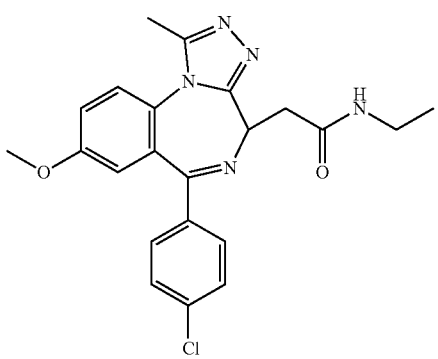 [SMILES: CCNC(=O)CC1N=C(c2ccc(Cl)cc2)c2cc(OC)ccc2-n2c(C)nnc21] |

| Ex. | Structure |
|---|---|
| 75 | 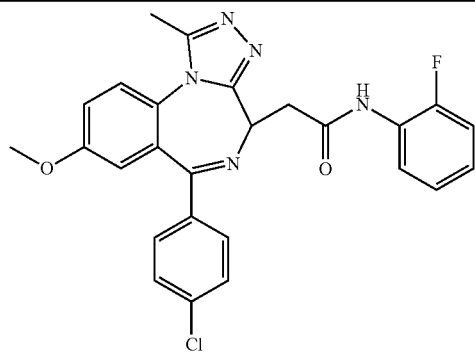 |
| 76 | 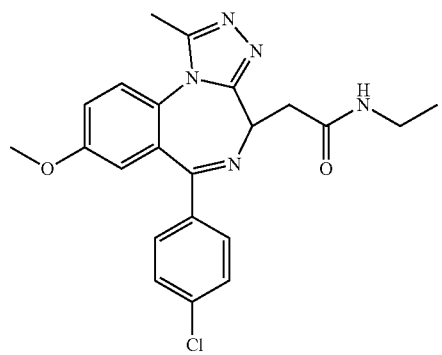 [SMILES: CCNC(=O)CC1N=C(c2ccc(Cl)cc2)c2cc(OC)ccc2-n2c(C)nnc21] |
| 77 | 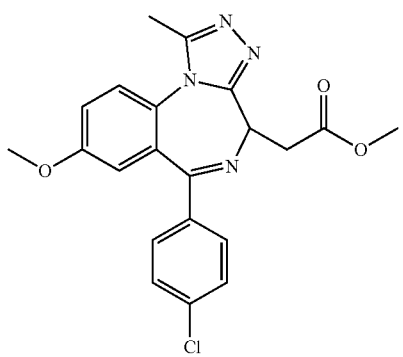 |
| 78 | 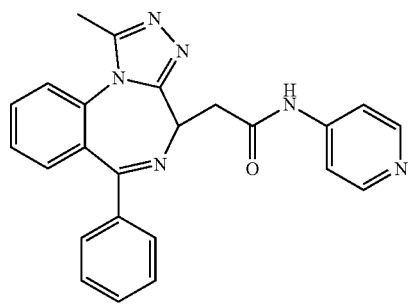 [SMILES: Cc1nnc2n1-c1ccccc1C(c1ccccc1)=NC2CC(=O)Nc1ccncc1] |

| Ex. | Structure |
|---|---|
| 79 | 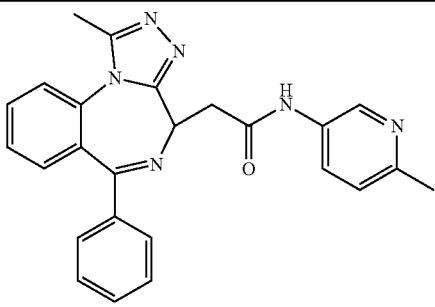 |
| 80 | 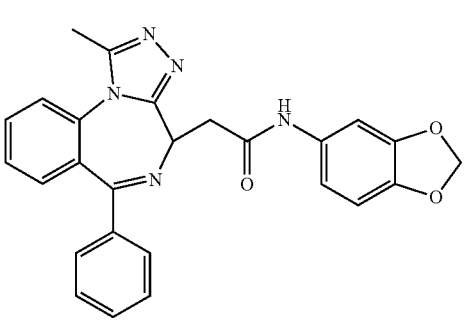 [SMILES: Cc1nnc2n1-c1ccccc1C(c1ccccc1)=NC2CC(=O)Nc1ccc2c(c1)OCO2] |
| 81 | 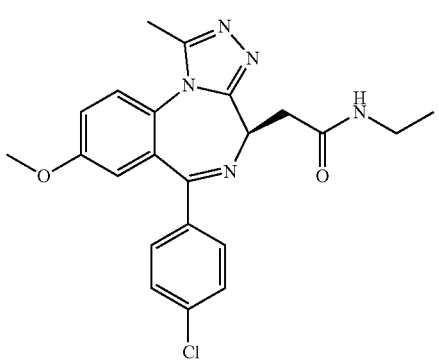 [SMILES: CCNC(=O)C[C@H]1N=C(c2ccc(Cl)cc2)c2cc(OC)ccc2-n2c(C)nnc21] |
| 82 | 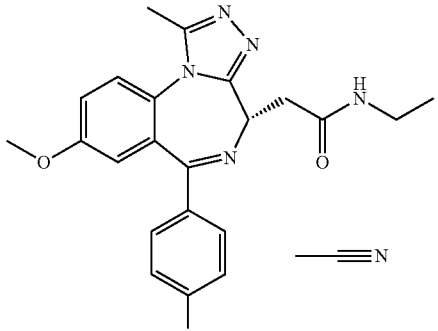 |

It will be understood that in the context of the examples used to illustrate the invention that information about how the compounds were prepared cannot be drawn from the format used to present the information, for example, the intermediates and final products may have been prepared by different individuals, and/or at different timepoints, employing various batches and appropriate techniques.

Experimental details of LC/MS methods D and F as referred to herein are as follows:

LC/MS (Method D) was conducted on a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% HCO$_2$H in water (solvent B), using the following elution gradient 0-0.7 minutes 0% B, 0.7-4.2 minutes 0→100% B, 4.2-5.3 minutes 100% B, 5.3-5.5 minutes 100∝30% B at a flow rate of 3 mL/minute. The mass spectra (MS) were recorded on a Fisons VG Platform mass spectrometer using electrospray positive ionisation [(ES+ve to give [M+H]$^+$ and [M+NH$_4$]$^+$ molecular ions] or electrospray negative ionisation [(ES–ve to give [M–H]– molecular ion] modes. Analytical data from this apparatus are given with the following format: [M+H]$^+$ or [M–H]$^-$.

LC/MS (Method F) was conducted on an Sunfire C18 column (30 mm×4.6 mm i.d. 3.5 μm packing diameter) at 30 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-0.1 min 3% B, 0.1-4.2min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 mL/minute. The mass spectra (MS) were recorded on a micromass LCT mass spectrometer using electrospray positive ionisation [ES+ve to give MH$^+$ molecular ions] or electrospray negative ionisation [ES–ve to give (M–H)– molecular ions] modes.

TLC (thin layer chromatography) refers to the use of TLC plates sold by Merck coated with silica gel 60 F254.

Silica chromatography techniques include either automated (Flashmaster or Biotage SP4) techniques or manual chromatography on pre-packed cartridges (SPE) or manually-packed flash columns.

When the name of a commercial supplier is given after the name of a compound or a reagent, for instance "compound X (Aldrich)" or "compound X/Aldrich", this means that compound X is obtainable from a commercial supplier, such as the commercial supplier named.

Reference compound A 2-methyl-6-(methyloxy)-4H-3,1-benzoxazin-4-one

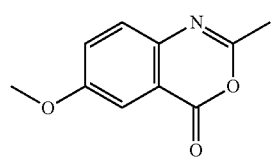

A solution of 5-methoxyanthranilic acid (Lancaster) (41.8 g, 0.25 mol) was refluxed in acetic anhydride (230 mL) for 3.5 h before being concentrated under reduced pressure. The crude compound was then concentrated twice in the presence of toluene before being filtered and washed twice with ether to yield to the title compound (33.7 g, 71% yield) as a brown solid; LC/MS (Method D): m/z 192 [M+H]$^+$, Rt 1.69 min.

Reference compound B

[2-amino-5-(methyloxy)phenyl](4-chlorophenyl)methanone

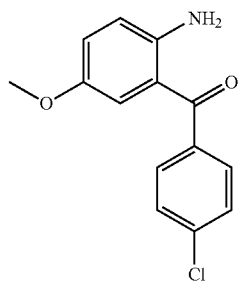 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 mL) at 0° C. was added dropwise a solution of 4-chlorophenylmagnesium bromide (170 mL, 1M in Et$_2$O, 0.17 mol). The reaction mixture was allowed to warm to room temperature and stirred for 1 h before being quenched with 1N HCl (200 mL). The aqueous layer was extracted with EtOAc (3×150 mL) and the combined organics were washed with brine (100 mL), dried over Na$_2$SO$_4$, filtered and concentrated under reduced pressure. The crude compound was then dissolved in EtOH (400 mL) and 6N HCl (160 mL) was added. The reaction mixture was refluxed for 2 h before being concentrated to one-third in volume. The resulting solid was filtered and washed twice with ether before being suspended in EtOAc and neutralised with 1N NaOH. The aqueous layer was extracted with EtOAc (3×150 mL) and the combined organics were washed with brine (150 mL), dried over Na$_2$SO$_4$, filtered and concentrated under reduced pressure. The title compound was obtained as a yellow solid (39 g, 88% yield); LC/MS (Method D): m/z 262 [M+H]+, Rt 2.57 min.

Reference Compound C

Methyl N$^1$-[2-[(4-chlorophenyl)carbonyl]-4-(methyloxy)phenyl]-N$^2$-{[(9H-fluoren-9-ylmethyl)oxy]carbonyl}-L-α-asparaginate

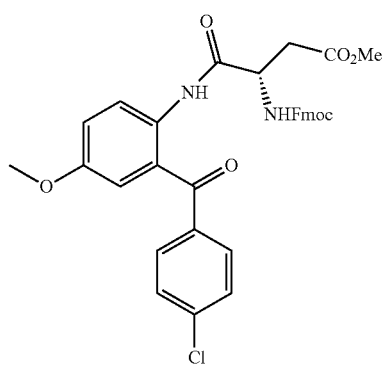

Methyl N-{[(9H-fluoren-9-ylmethyl)oxy]carbonyl}-L-α-aspartyl chloride (Int. J. Peptide Protein Res. 1992, 40, 13-18) (93 g, 0.24 mol) was dissolved in CHCl$_3$ (270 mL)

and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated at 60% in volume. Ether was added at 0° C. and the resulting precipitate was filtered and discarded. The filtrate was concentrated under reduced pressure and used without further purification.

Reference compound D

Methyl [(3S)-5-(4-chlorophenyl)-7-(methyloxy)-2-oxo-2,3-dihydro-1H-1,4-benzodiazepin-3-yl]acetate

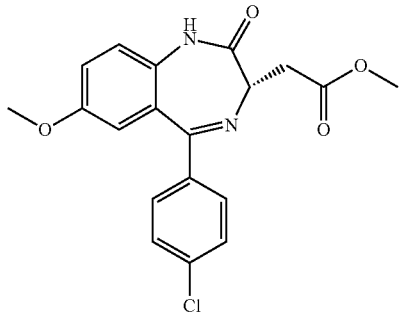

To a solution of Methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 mL) was added Et$_3$N (500 mL, 3.65 mol) and the resulting mixture was refluxed for 24h before being concentrated. The resulting crude amine was dissolved in 1,2-DCE (1.5 L) and AcOH (104 mL, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na$_2$SO$_4$, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product $R_f$=0.34 (DCM/MeOH: 95/5).

HRMS (M+H)$^+$ calculated for C$_{19}$H$_{18}$$^{35}$ClN$_2$O$_4$ 373.0955; found 373.0957.

Reference compound E

Methyl [(3S)-5-(4-chlorophenyl)-7-(methyloxy)-2-thioxo-2,3-dihydro-1H-1,4-benzodiazepin-3-yl]acetate

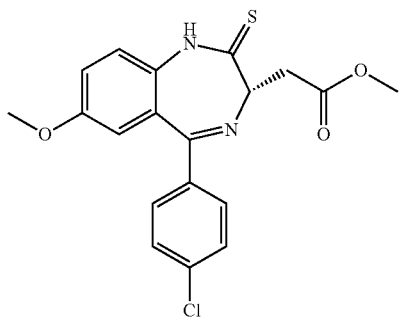

A suspension of P$_4$S$_{10}$ (36.1 g, 81.1 mmol) and Na$_2$CO$_3$ (8.6 g, 81.1 mmol) in 1,2-DCE (700 mL) at room temperature was stirred for 2 h before Methyl [(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. NaHCO$_3$ and brine. The organic layer was dried over Na$_2$SO$_4$, filtered and concentrated under reduced pressure. The crude product was purified by flash-chromatography on silica gel (DCM/MeOH: 99/1) to afford the title compound (17.2 g, 98% yield) as a yellowish solid. LC/MS (Method D): m/z 389 [M($^{35}$Cl)+H]$^+$, Rt 2.64 min HRMS (M+H)$^+$ calculated for C$_{19}$H$_{18}$$^{35}$ClN$_2$O$_3$S 389.0727; found 389.0714.

Reference compound F

Methyl [(3S)-2-[(1Z)-2-acetylhydrazino]-5-(4-chlorophenyl)-7-(methyloxy)-3H-1,4-benzodiazepin-3-yl]acetate

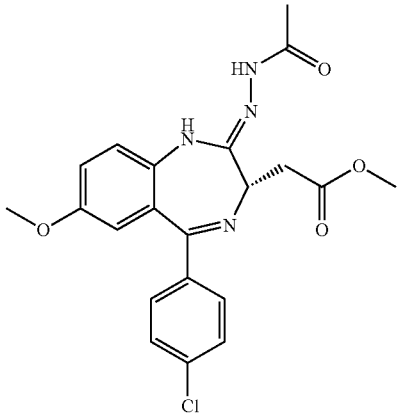

To a suspension of Methyl [(3S)-5-(4-chlorophenyl)-7-(methyloxy)-2-thioxo-2,3-dihydro-1H-1,4-benzodiazepin-3-yl]acetate (for a preparation see Reference compound E) (9.0 g, 23.2 mmol) in THF (300 mL) at 0° C. was added hydrazine monohydrate (3.4 mL, 69.6 mmol) dropwise. The reaction mixture was stirred for 5 h between 5° C. and 15° C. before being cooled at 0° C. Et$_3$N (9.7 mL, 69.6 mmol) was then added slowly and acetyl chloride (7.95 mL, 69.6 mmol) was added dropwise. The mixture was then allowed to warm to room temperature for 16 h before being concentrated under reduced pressure. The crude product was dissolved in DCM and washed with water. The organic layer was dried over Na$_2$SO$_4$, filtered and concentrated in vacuo to give the crude title compound (9.7 g, 98% yield) which was used without further purification. $R_f$=0.49 (DCM/MeOH: 90/10).

Reference compound G

Methyl [(4S)-6-(4-chlorophenyl)-1-methyl-8-(methyloxy)-4H-[1,2,4]triazolo[4,3-a][1,4]benzodiazepin-4-yl]acetate

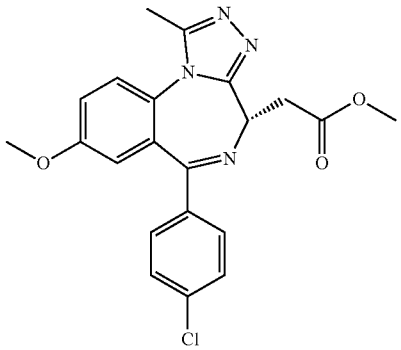

The crude Methyl [(3S)-2-[(1Z)-2-acetylhydrazino]-5-(4-chlorophenyl)-7-(methyloxy)-3H-1,4-benzodiazepin-3-yl]acetate (for a preparation see Reference compound F) (assumed 9.7 g) was suspended in THF (100 ml) and AcOH (60 mL) was added at room temperature. The reaction mixture was stirred at this temperature for 2 days before being concentrated under reduced pressure. The crude solid was triturated in i-Pr$_2$O and filtered to give the title compound (8.7 g, 91% over 3 steps) as an off-white solid. HRMS (M+H)$^+$ calculated for C$_{21}$H$_{20}$ClN$_4$O$_3$ 411.1229; found 411.1245.

Reference compound H

[(4S)-6-(4-Chlorophenyl)-1-methyl-8-(methyloxy)-4H-[1,2,4]triazolo[4,3-a][1,4]benzodiazepin-4-yl]acetic acid

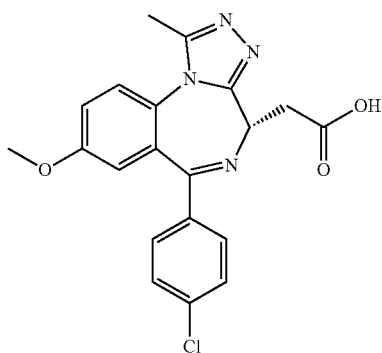 [SMILES: COc1ccc2c(c1)C(c1ccc(Cl)cc1)=N[C@@H](CC(=O)O)c1nnc(C)n1-2]

To a solution of Methyl [(4S)-6-(4-chlorophenyl)-1-methyl-8-(methyloxy)-4H-[1,2,4]triazolo[4,3-a][1,4]benzodiazepin-4-yl]acetate (for a preparation see Reference compound G)(7.4 g, 18.1 mmol) in THF (130 mL) at room temperature was added 1N NaOH (36.2 mL, 36.2 mmol). The reaction mixture was stirred at this temperature for 5 h before being quenched with 1N HCl (36.2 mL) and concentrated in vacuo. Water is then added and the aqueous layer was extracted with DCM (×3) and the combined organic layers were dried over Na$_2$SO$_4$, filtered and concentrated under reduced pressure to give the title compound (7 g, 98% yield) as a pale yellow solid.

Reference compound I 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

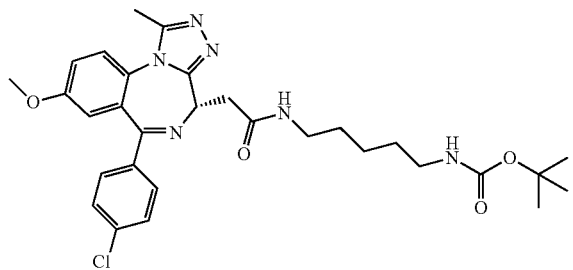 [SMILES: COc1ccc2c(c1)C(c1ccc(Cl)cc1)=N[C@@H](CC(=O)NCCCCCNC(=O)OC(C)(C)C)c1nnc(C)n1-2]

A mixture of [(4S)-6-(4-chlorophenyl)-1-methyl-8-(methyloxy)-4H-[1,2,4]triazolo[4,3-a][1,4]benzodiazepin-4-yl]acetic acid (for a preparation see Reference compound H) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference compound J

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate

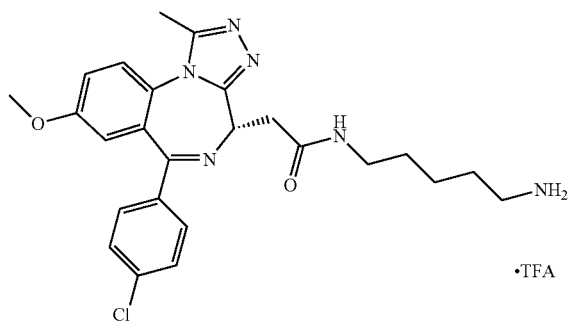 [SMILES: COc1ccc2c(c1)C(c1ccc(Cl)cc1)=N[C@@H](CC(=O)NCCCCCN)c1nnc(C)n1-2]

To a solution of 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound H) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg) LC/MS (Method D): rt=2.33 min.

HRMS (M+H)$^+$ calculated for C$_{25}$H$_{29}$ClN$_6$O$_2$ 481.2119; found 481.2162.

Reference compound K

Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide

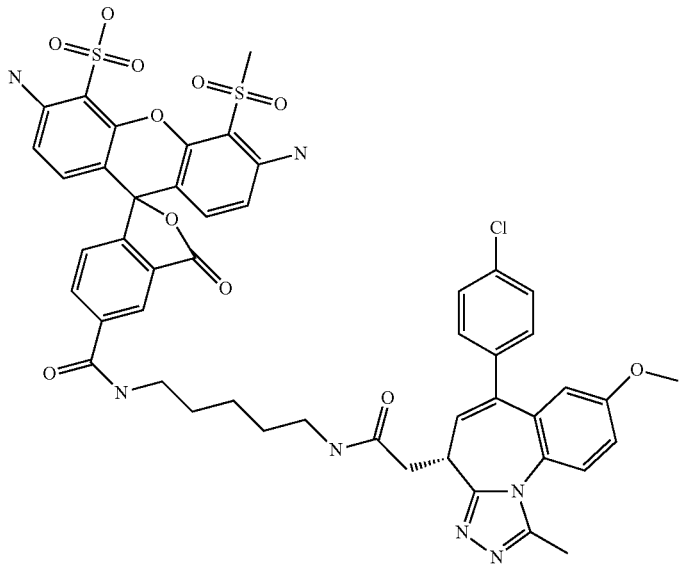

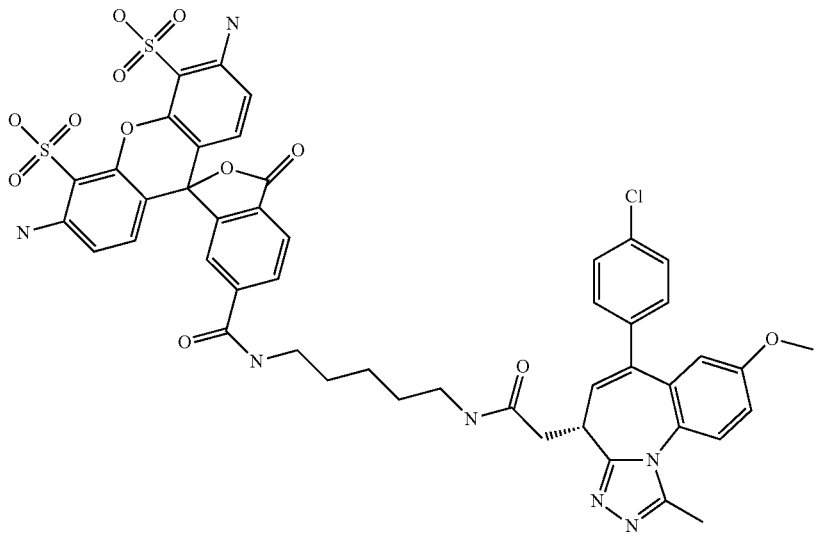

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J)(7.65 mg, 0.013 mmol) was dissolved in N,N-Dimethylformamide (DMF) (300 μl) and added to Alexa Fluor 488 carboxylic acid succinimidyl ester (5 mg, 7.77 μmol, mixture of 5 and 6 isomers, available from Invitrogen, product number A-20100) in an Eppendorf centrifuge tube. Hunig's base (7.0 μl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8 mg) as a mixture of the 2 regioisomers shown. LC/MS (Method F): MH+=999, rt=1.88 min.

Biological Test Methods

Fluorescence Anisotropy Binding Assay

The binding of the compounds of formula (I) to Bromodomain 2, 3 and 4 was assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$$y=a+((b-a)/(1+(10\char`\^x/10\char`\^c)\char`\^d)$$

Where 'a' is the minimum, 'b' is the Hill slope, 'c' is the pIC50 and 'd' is the maximum.

Recombinant Human Bromodomains (Bromodomain 2 (1-473), Bromodomain 3 (1-435) and Bromodomain 4 (1-477)) were expressed in *E.coli* cells (in pET15b vector) with a six-His tag at the N-terminal. The His-tagged Bromodomain was extracted from *E.coli* cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at −80° C. in 20 mM HEPES pH 7.5 and 100 mM NaCl.

Protocol for Bromodomain 2: All components were dissolved in buffer composition of 50 mM HEPES pH7.4, 150 mm NaCl and 0.5 mM CHAPS with final concentrations of Bromodomain 2, 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in the dark for 60 mins at room temperature. Fluorescence anisotropy was read in Envision ($\lambda$ex=485 nm, $\lambda$EM=530 nm; Dichroic—505 nM).

Protocol for Bromodoamin 3: All components were dissolved in buffer of composition 50 mM HEPES pH7.4, 150 mm NaCl and 0.5 mM CHAPS with final concentrations of Bromodomain 3, 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in the dark for 60 mins at room temperature. Fluorescence anisotropy was read in Envision ($\lambda$ex=485 nm, $\lambda$EM=530 nm; Dichroic—505 nM).

Protocol for Bromodomain 4: All components were dissolved in buffer of composition 50 mM HEPES pH7.4, 150 mm NaCl and 0.5 mM CHAPS with final concentrations of Bromodomain 4, 75 nM, fluorescent ligand 5 mM. 10 μl of this reaction mixture was added using a micro multidrop to wells containing 100 nl of various concentrations of test compound or DMSO vehicle (1% final) in Greiner 384 well Black low volume microtitre plate and equilibrated in the dark for 60 mins at room temperature. Fluorescence anisotropy was read in Envision ($\lambda$ex=485 nm, $\lambda$EM=530 nm; Dichroic—505 nM).

All examples (with the exception of examples 5-8, 18, 19, 30, 32, 33, 35, 49, 52, 53, 70-80 and 82) were tested in the assays described above. All tested compounds with the exception of Example 81 had a pIC50 5.0 in one or more of the BRD2, BRD3 and BRD4. Examples 1, 2, 4, 9-17, 22-24, 26, 34, 36-48, 50, 51, 54-56 and 58-65 had a pIC50 6.0 in one or more of the BRD2, BRD3 and BRD4 assays described above.

LPS Stimulated Whole Blood Measuring TNF$\alpha$ Levels Assay

Activation of monocytic cells by agonists of toll-like receptors such as bacterial lipopolysaccharide (LPS) results in production of key inflammatory mediators including TNF$\alpha$. Such pathways are widely considered to be central to the pathophysiology of a range of auto-immune and inflammatory disorders.

Compounds to be tested are diluted to give a range of appropriate concentrations and 1 ul of the dilution stocks is added to wells of a 96 plate. Following addition of whole blood (130 ul) the plates are incubated at 37 degrees (5% CO2) for 30 min before the addition of 10 ul of 2.8 ug/ml LPS, diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and TNF$\alpha$ levels assayed by immunoassay (typically by MesoScale Discovery technology) either immediately or following storage at −20 degrees. Dose response curves for each compound was generated from the data and an 1050 value was calculated.

Examples 1, 12, 14, 34, 36, 37 and 81 were tested in the above assay and were found to have a pIC50≥5.0. Examples 1, 12, 14, 34, 36 and 37 were tested in the above assay and were found to have a pIC50≥6.0.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 ul of the diluted stocks is added to a 96 well plate. Following addition of whole blood (130 ul) the plates are incubated at 37 degrees (5% CO2) for 30 min before the addition of 10 ul of 2.8ug/ml LPS, diluted in complete RPMI 1640 (final concentration =200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and IL-6 levels assayed by immunoassay (typically by MesoScale Discovery technology) either immediately or following storage at −20 degrees. Concentration response curves for each compound was generated from the data and an 1050 value was calculated.

Examples 1-4, 9-11, 13, 15, 17, 26, 31, 34, 38-48, 50, 51, 54, 55, 56, 58-64, 67, 69 and 81 were tested in the above assay and all, with the exception of Example 81, were found to have a pIC50≥5.0.

These data demonstrate that bromodomain inhibitors tested in the above two whole blood assays inhibited the production of the key inflammatory mediators TNF$\alpha$ and/or IL6. This suggests that such compounds have an anti-inflammatory profile.

In Vivo Mouse Endotoxemia Model

High doses of Endotoxin (bacterial lipopolysaccharide) administered to animals produce a profound shock syndrome including a strong inflammatory response, dysregulation of cardiovascular function, organ failure and ultimately mortality. This pattern of response is very similar to human sepsis and septic shock, where the body's response to a significant bacterial infection can be similarly life threatening.

To test the compounds of formula (I) and pharmaceutically acceptable salts thereof groups of eight Balb/c male mice were given a lethal dose of 15 mg/kg LPS by intraperitoneal injection. Ninety minutes later, animals were dosed intravenously with vehicle (20% cyclodextrin 1% ethanol in apyrogen water) or compound (10 mg/kg). The survival of animals was monitored at 4 days.

Numbers of animals surviving at 4 days (summed across multiple repeat experiments)

| Vehicle | 4/66 | (6%) |
|---|---|---|
| Compound of Example 1 | 24/56 | (52%) |

These data demonstrate that the bromodomain inhibitor tested in the above model gave rise to a significant animal survival effect following intravenous administration.

Cell Growth Assay

Human cell lines (n=33 comprising 15 heme cell lines, 14 breast cell lines and 4 other cell lines) were cultured in RPMI-1640 containing 10% fetal bovine serum, 1000 viable cells per well were plated in 384-well black flat bottom polystyrene plates (Greiner #781086) in 48 µl of culture media. All plates were placed at 5% $CO_2$, 37° C. overnight. The following day one plate was harvested with CellTiter-Glo (CTG, Promega #G7573) for a time equal to 0 (T0) measurement and compound (20 point titration from 14.7 uM to 7 pM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results were expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% ($gIC_{50}$) is the midpoint of the 'growth window' (between the T0 and DMSO control). The Ymin–T0 value is determined by subtracting the T0 value (100%) from the Ymin value (%) determined from the fit of the concentration response curve. Values from the wells with no cells were subtracted from all samples for background correction.

Example 1 was tested in accordance with the above assay and found to have a $gIC_{50}$ in the range 163-29300 nM across all cell lines, more specifically in the range 163-2480 nM for heme cell lines and 410-29300 nM for breast cell lines.

These data demonstrate that the bromodomain inhibitor tested in the above assay inhibited cell growth in a panel of oncology cell lines.

All publications, including but not limited to patents and patent applications, cited in this specification are herein incorporated by reference as if each individual publication were specifically and individually indicated to be incorporated by reference herein as though fully set forth.

The invention claimed is:

1. A compound of formula (I) or a pharmaceutically acceptable salt thereof:

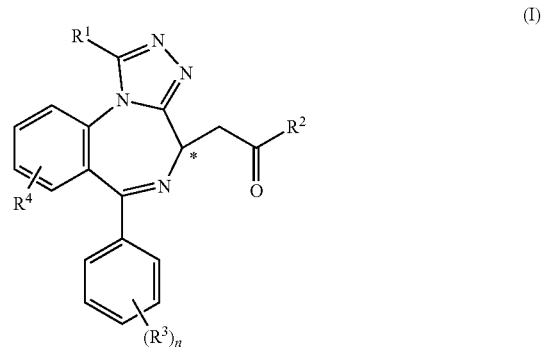

(I)

where
R$^1$ is $C_{1-3}$alkyl;
R$^2$ is —NR$^{2a}$R$^{2a'}$;
wherein R$^{2a}$ is hydrogen, and R$^{2a'}$ is heterocyclyl$C_{1-4}$alkyl,
wherein the heterocyclyl is optionally substituted once by amino, hydroxyl, or methyl;
each R$^3$ is independently selected from hydrogen, hydroxyl, halo, $C_{1-6}$alkyl, halo $C_{1-6}$alkyl, $C_{1-6}$alkoxy, halo $C_{1-6}$alkoxy, nitro, cyano, $CF_3$, —$OCF_3$, —COOR$^5$, and —$C_{1-4}$alkylOH;
R$^4$ is hydroxyl, halo, $C_{1-6}$alkyl, halo$C_{1-6}$alkyl, $C_{1-6}$alkoxy, halo$C_{1-6}$alkoxy, nitro, cyano, $CF_3$, —$OCF_3$, —COOR$^5$; or —$OS(O)_2C_{1-4}$alkyl;
R$^5$ is $C_{1-3}$alkyl; and
n is an integer 1 to 5.

2. The compound or salt according to claim 1, wherein R$^{2a'}$ is selected from heterocyclyl-CH$_2$—, heterocyclyl-CH$_2$CH$_2$—, heterocyclyl-CH$_2$CH$_2$CH$_2$— and heterocyclyl-CH$_2$CH$_2$CH$_2$CH$_2$—, wherein the heterocyclyl is optionally substituted once by amino, hydroxyl or methyl.

3. The compound or salt according to claim 2, wherein heterocyclyl is selected from tetrahydrofuranyl, pyrrolidinyl, piperidinyl, tetrahydropyranyl, piperazinyl, morpholino and thiomorpholinodioxide, wherein each group is optionally substituted once by amino, hydroxyl or methyl.

4. The compound or salt according to claim 3, wherein heterocyclyl is selected from:

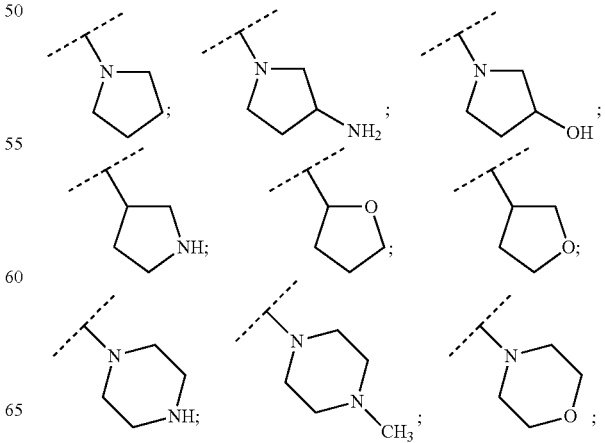

-continued

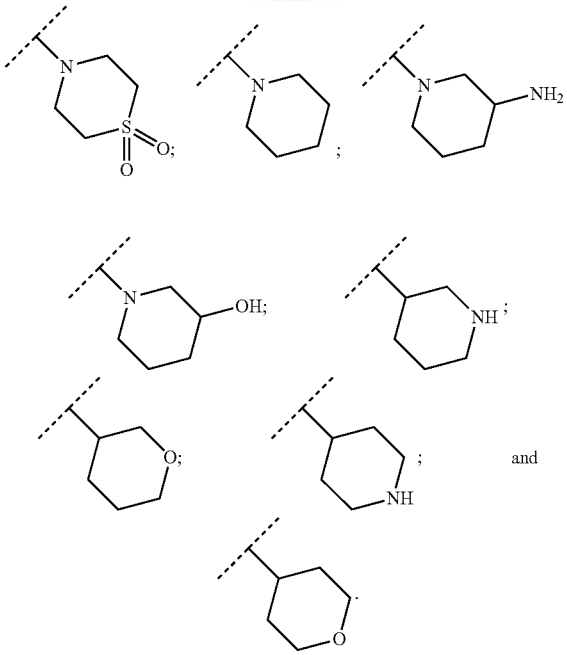

5. The compound or salt according to claim 1, wherein n is 1.

6. The compound or salt according to claim 5, wherein $R^3$ is 3-fluoro, 4- chloro, 4-fluoro, 4-methoxy or 4-$CF_3$.

7. The compound or salt according to claim 6, wherein $R^3$ is 4-chloro.

8. The compound or salt according to claim 1, wherein $R^4$ is MeO.

9. The compound or salt according to claim 8, wherein $R^4$ is 8-MeO.

10. The compound or salt according to claim 1 which is the S-enantiomer.

11. A compound which is:
2-[(4S)-6-(4-chlorophenyl)-1-methyl-8-(methyloxy)-4H-[1,2,4]triazolo [4,3-a][1,4]benzodiazepin-4-yl]-N-[2-(4-morpholinyl)ethyl]acetamide;

2-[(4S)-6-(4-chloropheny )-1-methyl-8-(methyloxy)-4H-[1,2,4]triazolo [4,3-a][1,4]benzodiazepin-4-yl]-N-[3-(4-morpholinyl)propyl]acetamide; or 2-[(4S)-6-(4-chlorophenyl)- 1 -methyl-8-(methyloxy)-4H- [1,2,4]triazolo [4,3-a][1,4]benzodiazepin-4-yl]-N-[2-(1,1-dioxido-4-thiomorpholinyl)ethyl]acetamide;
or a salt thereof.

12. A pharmaceutical composition which comprises the compound or salt according to claim 1 and one or more pharmaceutically acceptable carriers, diluents or excipients.

* * * * *